(12) United States Patent
Trenkle et al.

(10) Patent No.: US 7,569,734 B2
(45) Date of Patent: Aug. 4, 2009

(54) METHOD OF USING RHODIUM QUINONOID CATALYSTS

(75) Inventors: William C. Trenkle, Cranson, RI (US); Julia L. Barkin, Providence, RI (US); Seung Uk Son, Kyunggi-do (KR); Dwight A. Sweigart, Pawtucket, RI (US); Marcus D. Faust, Jr., Providence, RI (US)

(73) Assignee: Brown University, Providence, RI (US)

( * ) Notice: Subject to any disclaimer, the term of this patent is extended or adjusted under 35 U.S.C. 154(b) by 20 days.

(21) Appl. No.: 11/454,685

(22) Filed: Jun. 15, 2006

(65) Prior Publication Data

US 2007/0123715 A1     May 31, 2007

Related U.S. Application Data

(60) Provisional application No. 60/740,762, filed on Nov. 30, 2005.

(51) Int. Cl.
C07C 45/00 (2006.01)
C07C 303/00 (2006.01)
C07F 5/04 (2006.01)

(52) U.S. Cl. .......................... 568/401; 558/298; 558/40

(58) Field of Classification Search .......... 548/504; 568/343, 650, 401; 558/40, 298
See application file for complete search history.

(56) References Cited

U.S. PATENT DOCUMENTS 4,469,897 A   9/1984   Rivetti et al. ............... 568/650
5,278,305 A   1/1994   Kelsey ....................... 526/135

OTHER PUBLICATIONS

Xon et al. "An anionic Rhodium n4-Quinonoid Complex as a multifunctional Catalyst for the Arylation of Aldehydes with Arylboronic Acids" Aug. 2005, Journal of American Chemical Society, vol. 127, pp. 12238-12239.*
Hawley's Condensed Chemical Dictionary, Hydroquinone, 2002, John Wiley & Sons, Inc., pp. 1-3.*
Rouhi, A. Maureen, "Fine Chemicals", Sep. 6, 2004, pp. 1-11, Chemical & Engineering News, Internet Article: http://pubs.acs.org/cen/coverstory/8236/8236finechecmicals.html.
Moussa, J. et al., "$\eta^5$-Semiquinone Complexes and the Related $\eta^4$-Benzoquinone of (Pentamethycyclopentadienyl) rhodium and -iridium: Synthesis, Structures, Hydrogen Bonding, and Electrochemical Behavior", 2004, pp. 6231-6238, Organometallics, vol. 23, No. 26.
Moussa, J. et al., "Self-Assembly of 1-D Coordination Polymers Using Organometallic Linkers and Exhibiting Argentophilic Interations $AG^{I \cdots} AG^{I}$", 2005, pp. 3808-3810, Eur. J. Inorg. Chem.

(Continued)

Primary Examiner—Porfirio Nazario-Gonzalez
Assistant Examiner—Yate'k Cutliff
(74) Attorney, Agent, or Firm—Harrington & Smith, PC

(57) ABSTRACT

In accordance with aspects of the invention methods of using rhodium hydroquinone catalysts for the conjugate addition of boronic acids are disclosed.

23 Claims, 15 Drawing Sheets

OTHER PUBLICATIONS

Son, S. U. et al., "Organometallic crystal engineering of [(1,4- and 1,3-hydroquinone)Rh(P(OPh)$_3$)$_2$]BF$_4$ by charge assisted hydrogen bonding", 2005, pp. 708-710, Journal Royal Society of Chemistry.

Son, S. U. et al., "Organometallic crystal engineering of [(1,4- and 1,3-hydroquinone)Rh(P(OPh)$_3$)$_2$]BF$_4$ by charge assisted hydrogen bonding", 2005, 2 pages, Supplementary Material (ESI) for Chemical Communications.

Son, S. U. et al., "An Anionic Rhodium η$^4$-Quinonoid Complex as a Multifunctional Catalyst for the Arylation of Aldenhydes with Arylboronic Acids", 2005, vol. 127, No. 35, pp. 12238-12239, J. American Chemical Society.

Son, S. U. et al., "Lithium Alkoxide {Li$_4$O$_4$} Cubanes Bridged by Rhodium-Quinonoid Organometalloligands", 2005, pp. 7710-7715, Angew. Chem. Int. Ed.

Son, S. U. et al., "Rh$^-$Li$^+$", 2005, pp. SI 1-6, Angewandte Chemie, Supporting Information.

Son, S. U. et al., "An Anionic Rhodium η$^4$-Quinonoid Complex as a Multifunctional Catalyst for the Phenylation of Aldehydes with Phenylboronic Acid", 2005, pp. S1-S9, Angewandte Chemie, Supporting Information.

Carreira, Erick M., Abstract, "Axial-chiral 1-phthalazinylnaphthyl monophosphine ligands and their transition metal complexes as asymmetric addition, hydroboration, cyclization and substitution reaction catalysts for production of optically active compounds", Dec. 22, 2005, 2 pages.

Boaz, N. W., Abstract, "Preparation of phosphine aminophosphine cocatalysts", Jun. 14, 2005, 2 pages.

Boaz, N. W., Abstract, "Preparation of Phosphine-phosphoramidite compounds useful as cocatalysts", Jun. 14, 2005, 2 pages.

Batey, Robert A., Abstract, "Rhodium-catalyzed addition of alkenyl- and aryltrifluoroborates to aldehydes and enones", Apr. 7, 2001, 1 page.

Maeda, A., Abstract, "Preparation of branched polyenes as monomers for unsaturated polymers", Nov. 17, 1998, 2 pages.

Hara, Y. et al., Abstract, "The acyloxy conversion catalyst of the conjugated diene and the manufacturing method for the preparation of unsaturated glycol diester", Sep. 2, 1998, 2 pages.

Auvray, P., Abstract, "Rhodium-phosphine catalysts for hydrogenation and addition reactions", Mar. 18, 1992, 1 page.

Abstract, "Alkenyl malonic acid cyclic esters", (Mitsui Petrochemical Industries, Ltd., Japan), May 2, 1980, 1 page.

Pierpont, C. G. et al., "The Chemistry of Transition Metal Complexes Containing Catechol and Semiquinone Ligands", Prog. Inorg. Chem. 1994, vol. 41, pp. 331-443.

Ebadi, M. et al., "Ruthenium Complexes of Quinone Related Ligands: A Study of the Electrochemical Properties of 2-Aminothiophenolatobis (2,2'-Bipyridine) Ruthenium (II)", pp. 467-474.

Huang, Y. et al., "Reactions of Quinones and Quinoid Molecules with the Cp*Ru$^+$Fragment. Electron Redistribution and Transposition Reactions", Organometallics 1992, vol. 11, pp. 3031-3035.

Koelle, U. et al., "Complexation and aromatization of α, β-unsaturated cyclic ketones by Ru(H$_2$O)$^{2+}_6$ and (Bz)Ru(H$_2$0)$^{2+}_3$:molecular structure of (η$^6$-Tosylate) (η$^5$-hydroxycyclopentadienyl) Ru and of (η$^6$ -Tosylate) (η$^6$-1,4-dihydroxy-2,3,5,6-tetrametheylbenzene)Ru", Journal of Organometallic Chemistry 490 1995, pp. 101-109.

Schumann, H. et al., "Synthesis and Reactivity of 1,2- and 1,4-Dihydroxyarene Complexes of Chromium Tricarbonyl", Polyhedron 1999, vol. 9, No. 14, pp. 1677-1681.

Sun, S. et al., "η$^6$-Hydroquinone and catechol complexes of manganese tricarbonyl", Journal of Organometallic Chemistry 1996, vol. 512, pp. 257-259.

Le Bras, J. et al., "p-, o-η$^4$-Benzoquinone and the Related η$^6$-Hydroquinone, η$^6$-Catechol Complexes of Pentamethylcyclopentadienyliridium: Synthesis, Structures, and Reactivity", Organometallics 1998, vol. 17, pp. 1116-1121.

Oh, M. et al., "η$^5$-Semiquinone and η$^4$-Quinone Complexes of Manganese Tricarbonyl. Intermolecular Hydrogen Bonding in the Solid State and in Solution", Organometallics 2002, vol. 21, pp. 1290-1295.

Oh, M. et al., "Supramolecular Metal—Organometallic Coordination Networks Based on Quinonoid—Complexes", Accounts of Chemical Research 2004, vol. 37, No. 1, pp. 1-11.

Casey, C. P. et al., "Hydrogen Elimination from a Hydroxycyclopentadienyl Ruthenium (II) Hydride; Study of Hydrogen Activation in a Ligand-Metal Bifunctional Hydrogenation Catalyst", J. Am. Chem. Soc. 2005, vol. 127, pp. 3100-3109.

Mermerian, A. et al., "Catalytic Enantioselective Synthesis of Quaternary Stereocenters via Intermolecular C-Acylation of Silyl Ketene Acetals: Dual Activation of the Electrophile and the Nucleophile", J. Am. Chem. Soc. 2003, vol. 125, pp. 4050-4051.

Suzuki, A., "Organoborates in New Synthetic Reactions", Acc. Chem. Res. 1982, vol. 15, pp. 178-184.

Miyaura, N. et al., "Palladium-Catalyzed Cross-Coupling Reactions of Organoboron Compounds", Chem. Rev. 1995, vol. 95, pp. 2457-2483.

Sakai, M. et al., "Rhodium-Catalyzed Addition of Organoboronic Acids to Aldehydes", Angew. Chem. Int. Ed. 1998, vol. 37, No. 23, pp. 3279-3281.

Ueda, M. et al., "A Large Accelerating Effect of Tri(tert-butyl)phosphine in the Rhodium-Catalyzed Addition of Arylboronic Acids to Aldehydes", J. Org. Chem. 2000, vol. 65, pp. 4450-4452.

Furstner, A. et al., "Practical Method for the Rhodium-Catalyzed Addition of Aryl- and Alkenylboronic Acids to Aldehydes", Adv. Synth. Catal. 2001, vol. 343, No. 4, pp. 343-350.

Pucheault, M. et al., "Direct Access to Ketones from Aldehydes via Rhodium-Catalyzed Cross-Coupling Reaction with Potassium Trifluoro(organo)borates", J. Am. Chem. Soc. 2004, vol. 126, pp. 15356-13537.

Takaya, Y. et al., "Rhodium-Catalyzed Asymmetric 1,4-Addition of Aryl- and Alkenylboronic Acids to Enones", J. Am. Chem. Soc. 1998, vol. 120, pp. 5579-5580.

Batey, R. A. et al., "Potassium Alkenyl- and Aryltrifluoroborates: Stable and Efficient Agents for Rhodium-Catalyzed Addition to Aldehydes and Enones", Organic Letters 1999, vol. 1, No. 10, pp. 1683-1686.

Ramnauth, J. et al., "Stereoselective C-Glycoside Formation by a Rhodium(1)-Catalyzed 1,4-Addition of Arylboronic Acids to Acetylated Enones Derived from Glycals", Organic Letters 2001, vol. 3, No. 16, pp. 2571-2573.

Kuriyama, M. et al., "Hemilabile Amidomonophosphine Ligand-Rhodium(1) Complex-Catalyzed Asymmetric 1,4-Addition of Arylboronic Acids to Cycloalkenones", J. Am. Chem. Soc. 2002, vol. 124, pp. 8932-8939.

Hayashi, T. et al., "Catalytic Cycle of Rhodium-Catalyzed Asymmetric 1,4-Addition of Organoboronic Acids. Arylrhodium, Oxa—allylrhodium, and Hydroxorhodium Intermediates", J. Am. Chem. Soc. 2002, vol. 124, pp. 5052-5058.

Yoshida, K. et al., "A New Type of Catalytic Tandem 1,4-Addition-Aldol Reaction Which Proceeds through an (Oxa-π-allyl)rhodium Intermediate", J. Am. Chem. Soc. 2002, vol. 124, pp. 10984-10985.

Itooka, R. et al., "Rhodium-Catalyzed 1,4-Addition of Arylboronic Acids to α,β-Unsaturated Carbonyl Compounds; Large Accelerating Effects of Bases and Ligands", J. Org. Chem. 2003, vol. 68, pp. 6000-6004.

Duursma, A. et al., "Highly Enantioselective Conjugate Additions of Potassium Organotrifluoroborates to Enones by Use of Monodentate Phosphoramidite Ligands", J. Org. Chem. 2004, vol. 69, pp. 8045-8052.

Sammis, G. et al., "Cooperative Dual Catalysis: Application to the Highly Enantioselective ConjugateCyanation of Unsaturated Imides", J. Am. Chem. Soc. 2004, vol. 126, pp. 9928-9929.

Shibasaki. M. et al., "Lanthanide Complexes in Multifunctional Asymmetric Catalysis", Chem. Rev. 2002, vol. 102, pp. 2187-2209.

Yamagiwa, N. et al., "Heterobimetallic Catalysis in Asymmetric 1,4-Addition of O-Alkylhydroxylamine to Enones", J. Am. Chem. Soc. 2003, vol. 125, pp. 16178-16179.

Li, C. et al., "The Rh$_4$(CO)$_{12}$-Catalyzed Hydroformylation of 3,3-Dimethylbut-1-ene Promoted with HMn(CO)$_5$. Bimetallic Catalytic Binuclear Elimination as an Origin for Synergism in Homogenous Catalysis", J. Am. Chem. Soc. 2003, vol. 125, pp. 5540-5548.

Guo, N. et al., "Bimetallic Catalysis for Styrene Homopolymerization and Ethylene-Styrene Copolymerization. Exceptional Comonomer Selectivity and Insertion Regiochemistry", J. Am. Chem. Soc. 2004, vol. 126, pp. 6542-6543.

Comte, V. et al., "[TiPHOS(Rh)]+: A Fortuitous Coordination Mode and an Effective Hydrosilylation Bimetallic Catalyst", Organometallics 2005, vol. 24, pp. 1439-1444.

Braga, A. C. et al., "Computational Characterization of the Role of the Base in the Suzuki- Miyaura Cross-Coupling Reaction", J. Am. Chem. Soc. 2005, vol. 127, pp. 9298-9307.

Noyori, R. et al., "Asymmetric Transfer Hydrogenation Catalyzed by Chiral Ruthenium Complexes", Acc. Chem. Res. 1997, vol. 30, pp. 97-102.

Josephson, N. S. et al., "Mechanism of Enantioselective Ti-Catalyzed Strecker Reaction: Peptide-Based Metal Complexes as Bifunctional Catalysts", J. Am. Chem. Soc. 2001, vol. 123, pp. 11594-11599.

Sakai, M. et al., "Rhodium-Catalyzed Conjugate Addition of Aryl- or 1-Alkenylboronic Acids to Enones", Organometallics, vol. 16, No. 20, Sep. 30, 1997, pp. 4229-4231.

Fagnou, K. et al., "Rhodium-Catalyzed Carbon' Carbon Bond Forming Reactions of Organometallic Compounds", Chem. Rev. 2003, vol. 103, pp. 169-196.

Hayashi, T. et al., "Rhodium-Catalyzed Asymmetric 1,4-Addition and Its Related Asymmetric Reactions", Chem. Rev. 2003, vol. 103, pp. 2829-2844.

Hayashi, T., "Rhodium-Catalyzed Asymmetric Addition of Aryl- and Alkenylboron Reagents to Electron-Deficient Olefins", Pure Appl. Chem. 2004, vol. 76, No. 3, pp. 465-475.

Chapman, C. J. et al., "Synthesis of Functionalised Phenylalanines Using Rhodium Catalysis in Water", Adv. Synth. Catal. 2003, vol. 345, No. 3, pp. 353-355.

Moss, R. J. et al., "Rhodium Catalysed Tandem Conjugate Addition-Protonation: An Enantioselective Synthesis of 2-Substituted Succinic Esters", Chem. Commun., 2004, pp. 1984-1985.

Paquin, J. et al., "Asymmetric Synthesis of 3,3-Diarylpropanals with Chiral Diene-Rhodium Catalysts", J. Am. Chem. Soc. 2005, vol. 127, pp. 10850-10851.

Son, S. U. et al., "An Anionic Rhodim $\eta^4$-Quinonoid Complex as a Multifunctional Catalysts for the Arylation of Aldehydes with Arylboronic Acids", J. Am. Chem. Soc. 2005, vol. 127, pp. 12238-12239.

Zou, G. et al., "Rhodium-Catalyzed Heck-Type Reaction of Arylboronic Acids With $\alpha,\beta$-hydrogen Elimination vs. Hydrolysis of Alkylrhodium Species," Chem. Commun. 2003, pp. 2438-2439.

Mori, A. et al., "Hydroxorhodium Complex-Catalyzed Carbon-Carbon Bond-Forming Reactions of Silanediols with $\alpha,\beta$-Unsaturated Carbonyl Compounds. Mizoroki-Heck-Type Reaction vs Conjugate Addition", J. Am. Chem. Soc. 2001, vol. 123, pp. 10774-10775.

Braga, D. et al., "Crystal Engineering and Organometallic Architecture", Chem. Rev. 1998, vol. 98, pp. 1375-1405.

Sun, S. et al., "Self-Assembly Organometallic Squares With Terpyridyl Metal Complexes as Bridging Ligands", Inorg. Chem. 2001, vol. 40, pp. 3154-3160.

Kuehl, C. J. et al., "Self-Assembly of Molecular Prisms via an Organometallic 'Clip'", Organic Letters 2002, vol. 4, No. 6, pp. 913-915.

Shin, D. M. et al., "Self-Assembly of Discrete Organometallic-Organic Hybrid Supramolecular Arrays from Ferrocenyl Dipyridines and Terephthalic and Trimesic Acids", Crystal Growth & Design 2002, vol. 2, No. 6, pp. 493-496.

Kim, Y. et al., "Organic-Organometallic Crystal Engineering: Novel Formation of a Honeycomb Supramolecular Architecture of [Re$_2$($\mu$-OMe)$_3$(CO)$_6$] Anions Encapsulating a Linear H-Bonded Chain of [DABCO-H]+Cations", Inorganic Chemistry 2003, vol. 42, No. 14, pp. 4262-4264.

Hartnell, R. D. et al., "Peripherally $\eta^1$-Platinated Organometallic Porphyrins as Building Blocks for Multiporphyrin Arrays", Organometallics 2004, vol. 23, pp. 391-399.

Dong, Y. et al., "Organometallic Silver(I) Supramolecular Complexes Generated from Multidentate Furan-Containing Symmetric and Unsymmetric Fulvene Ligands and Silver(I) Salts", Inorg. Chem. 2005, vol. 44, pp. 1693-1703.

Eaton D. F. et al., "Control of Bulk Dipolar Alignment Using Guest-Host Inclusion Chemistry: New Materials for Second-Harmonic Generation", J. Am. Chem. Soc. 1987, vol. 109, pp. 1886-1888.

Lee, I. S. et al., "Organometallic-Organic Hybrid Crystals from Ferrocenyl Dipyridine and Binaphthol: Different Crystal Structures and Nonlinear Optical Properties Depending Upon the Reaction Medium and Optical Purity of Binaphthol", Organometallics 1999, vol. 18, pp. 5080-5085.

Barlow, S. et al., "Electronic and Optical Properties of Conjugated Group 8 Metallocene Derivatives", Chem. Commun., 2000, pp. 1555-1562.

Albrecht, M. et al., "Organoplatinum Crystals for Gas-Triggered Switches", Nature, Aug. 31, 2000, vol. 406, pp. 970-974.

Albrecht, M. et al., "Platinum Group Organometallics Based on 'Pincer' Complexes: Sensors, Switches, and Catalysts", Angew. Chem. Int. Ed. 2001, vol. 40, pp. 3750-3781.

Dinolfo, P. H. et al., "Supramolecular Coordination Chemistry and Functional Microporous Molecular Materials", Chem. Mater. 2001, vol. 13, pp. 3113-3125.

Lee, S. J. et al., "The First Chiral Organometallic Triangle for Asymmetric Catalysis", J. Am. Chem. Soc. 2002, vol. 124, pp. 12948-12949.

Resendiz, M. J. et al., "A Self-Assembled Supramolecular Optical Sensor for Ni(II), Cd(II), and Cr(III)", Organic Letters 2004, vol. 6, No. 5, pp. 651-653.

Braga, D. et al., "Novel Organometallic Building Blocks for Crystal Engineering. Synthesis and Structural Characterization of the Dicarboxylic Acid [Cr$^0$($\eta^6$-C$_6$H$_5$COOH)$_2$], of Two Polymorphs of Its Oxidation Derivative [Cr$^1$($\eta^6$-C$_6$H$_5$COOH)$_2$]+[PF$_6$]–, and of the Zwitterionic Form [Cr$^1$($\eta^6$-C$_6$H$_5$COOH)($\eta^6$-C$_6$H$_5$COO)]", Organometallics 2001, vol. 20, pp. 1875-1881.

Braga, D. et al., "Reversible Gas-Solid Reactions between the Organometallic Zwitterion [($\eta^5$-C$_5$H$_4$COOH) ($\eta^5$-C$_5$H$_4$COO)Co$^{III}$]and Vapors of Trifluoroacetic and Tetrafluoroboric Acids", Organometallics 2002, vol. 21, pp. 1315-1318.

Braga, D. et al., "Design, Synthesis, and Structural Characterization of Molecular and Supramolecular Heterobimetallic Metallamacrocycles Based on the 1,1-Bis(4-pyridyl)ferrocene (Fe($\eta^5$-C$_5$H$_4$-1-C$_5$H$_4$N)$_2$) Ligand" Organometallics 2003, vol. 22, pp. 4532-4538.

Braga, D. et al., "Novel Organometallic Building Blocks for Molecular Crystal Engineering. 2. Synthesis and Characterization of Pyridyl and Pyrimidyl Derivatives of Diboronic Acid, [Fe($\eta^5$-C$_5$H$_4$-B(OH)$_2$)$_2$], and of Pyridyl Boronic Acid, [Fe($\eta^5$-C$_5$H$_4$-4-C$_5$H$_4$N)($\eta^5$-C$_5$H$_4$-B(OH)$_2$)]", Organometallics 2003, vol. 22, pp. 2142-2150.

Braga, D. et al., "Novel Organometallic Building Blocks for Molecular Crystal Engineering. 3. Synthesis, Characterization and Hydrogen Bonding of the Crystalline Mono- and Bis-Amide Derivatives of [Co$^{III}$($\eta^5$-C$_5$H$_4$-COOH)$_2$]+and of the Cationic Zwitterion [Co$^{III}$($\eta^5$-C$_5$H$_4$CONHC$_5$H$_4$NH)($\eta^5$-C$_5$H$_4$COO)]+", Crystal Growth & Design 2004, vol. 4, No. 4, pp. 769-774.

Braga, D. et al., "Intermolecular Interactions In Nonorganic Crystal Engineering", Acc. Chem. Res. 2000, vol. 33, pp. 601-608.

Xu, X. et al., "A Nanoporous Metal-Organic Framework Based on Bulky Phosphane Ligands", Angew. Chem. Int. Ed. 2002, vol. 41, No. 5, pp. 764-767.

Pschirer, N. G. et al., "Noninterpenetrating Square-Grid Coordination Polymers With Dimensions of 25×25 Å$^2$Prepared by Using N$_2$N$^1$-Type Ligands: The First Chiral Square-Grid Coordination Polymer", Agnew. Chem. Int. Ed. 2002, vol. 41, No. 4, pp. 583-585.

Moulton, B. et al., "Coordination Polymers: Toward Functional Transition Metal Sustained Materials and Supermolecules", Current Opinion in Solid State & Materials Science 2002, vol. 6, pp. 117-123.

Kannan, S. et al., "Reaction chemistry of [Pd$_2$($\mu$-OH)$_2$L$_4$]$^{2+}$ with aryl amines. Structures of [Pd$_2$($\mu$-OH){$\mu$-NH($\rho$-tol)(PPh$_3$)$_4$](BF$_4$)$_2$, [Pd($\eta^3$-CH$_2$C(NH($\rho$-tol)CH$_2$)(PPh$_3$)](BF$_4$), and [Pd(PMe$_2$Ph)$_2$($\mu$-PF$_2$O$_2$)]$_2$(PF$_6$)$_2$", Inorganica Chimica Acta 2003, vol. 345, pp. 8-14.

Son, S. et al., "Charge-Assisted Hydrogen Bonding and Other Non-Covalent Interactions in the Self-Assembly of the Organometallic Building Block [($\eta^6$-Hydroquinone)Rh(P(OPh)$_3$)$_2$]+ with a Range of Counteranions", Organometallics 2006, pp. 1-27.

Kazarian, S. G. et al., "Is Intermolecular Hydrogen-Bonding to Uncharged Metal Centers of Organometallic Compounds Widespread in Solutions? A spectroscopic Investigation in Hydrocarbon, Noble Gas, and Supercritical Fluid Solutions of the Interaction between Fluoro Alcohols and $(\eta^5-C_5R_5)ML_2$ (R=H, Me; M=Co, Rh, Ir; L=CO, $C_2H_4$, $N_2$, $PMe_3$) and Its Relevance to Protonation", J. Am. Chem. Soc. 1993, vol. 115, pp. 9069-9079.

Iogansen, A. V. et al., "Hyrdogen Bond Energy and Proton-Donating Ability of Fluorinated Alcohols", Translated from Zhurnal Prikl. Spektrosk., 1980, vol. 33, pp. 460-466.

Kesanli, B. et al., "Highly Interpenetrated Metal-Organic Frameworks for Hydrogen Storage", Angew. Chem. Int. Ed. 2005, vol. 44, pp. 72-75.

Burrows, A.D. et al., "Multidimensional Crystal.Engineering of Bifunctional Metal Complexes Containing Complementary Triple Hydrogen Bonds", 1995, pp. 329-339, Chem. Soc. Ref.

Spartan '04, Version 1.0.3; pp. 215-224, Wavefunction, Inc., Irvine, CA, W.J.A. Guide to Molecular Mechanics and Quantum Chemical Calculations, Chapter 16.

Braga, D. et al., "Polymorphism of Molecular Organometallic Crystal. A Third Form of the Supramolecular Hydrogen-Bonded Dimer $\{[Fe^{II}(\eta^5-C_5H_4COOH)_2]\}_2$", 2004, pp. 1109-1112, Crystal Growth & Design, vol. 4, No. 6.

Lautens, Mark et al., "Rhodium-Catalyzed Heck-Type Coupling of Boronic Acids with Activated Alkenes in an Aqueous Emulsion", 2004, pp. 2006-2014, Synthesis 2004, No. 12.

Weiss, E., "Structures of Organo Alkali Metal Complexes and Related Compounds", Nov. 1993, pp. 1501-1670, Angew. Chem. Int. Ed. Engl. vol. 32, No. 11.

Beswick, M.A. et al., "Alkali Metals", 1994, pp. 1, Comprehensive Organometalic Chemistry II, vol. 1.

Williard, P. G. et al., "X-Ray Crystal Structure of a Lithium Aldolate-A Tetrameric Aggregate", 1985, pp. 3931-3934, Tetrahedron Letters, vol. 26, No. 33.

Gais, H. et al., "Isolation and X-ray Crystal Structure of the Tetrameric Lithium-Coordinated α-Sulfonimidoyl Carbanion $[Me_3Si)CH \{S(O)(NsiMe_3)\}Li]_4$: The First Structure of an α-SO Substituted Lithium Alkyl Having No External Donor Ligands", 1987, pp. 3775-3776, J. Am. Chem. Soc., vol. 109, No. 12.

Nichols, M.A. et al., "Chelation of-Substituted-1-lithoxides: Structural and Energetic Factors of Relevance to Synthetic Organic Chemistry", 1991, pp. 6222-6233, J. Am. Chem. Soc., vol. 113, No. 16.

Pospisil, P. J. et al., "A Substoichiometric Pyridine-Lithium Enolate Complex: Solution and X-ray Data and Implications for Catalysis in the Aldol Reaction", 1992, pp. 7585-7587, J. Am. Chem. Soc., vol. 114, No. 19.

Schutte, S. et al., "A stable aquo-complex of lithiated di-tert-butylfluorosilanol", 1993, pp. 45-49, Journal of Organometallic Chemistry, vol. 446.

Piarulli, U. et al., "Carbohydrate Metal Complexes as Ligands for Alkali Cations", 1994, pp. 1409-1410, J. Chem. Soc.

Apeloig, Y. et al., "Synthesis and the electronic spectra of the first β-ketoacylsilanes and their lithium enolates: new insights into hyperconjugation in acylsilanes and their enolates", 1995, pp. 73-82, Journal of Organometallic Chemistry, vol. 499.

Clegg, W. et al., "The synthesis and solid-state and solution structures of an unprecedented mixed chiral α-amino lithium alkoxide-lithium alkoxide aggregate", 1998, pp. 1323-1326, New J. Chem.

Armstrong, D. R. et al., "Dynamic process in organolithium chemistry: tetrameric and 'open' tetrameric chiral α-amino lithium alkoxides", 1999, 7 pgs., New J. Chem.

Hoskin, A. J. et al., "Decamethylzirconocene-Chalcogenide-Hydride Complexes", 1999, pp. 2479-2483, Organometallics, vol. 18.

Jones, C. et al., "Syntheses and structural studies of lithium complexes of 2-amino-6-methylpyridine", 2000, 5 pgs., J. Chem. Soc., Dalton Trans.

Strauch, J. et al., "Formation and Structural properties of salicylaldiminato complexes of zirconium and titanium", 2000, pp. 810-821, Inorganica Chimica Acta 300-302.

Lorenz, V. et al., "ƒ-Element Disiloxanediolates: Novel Si-O-based Inorganic Heterocycles", 2001, pp. 848-857, Chem. Eur. Journal, vol. 7, No. 4.

Boyle, T. J. et al., "Structural Diversity of Lithium Neopentoxide Compounds", 2001, pp. 6281-6286, Inorg. Chem., vol. 40.

Seebach, D. et al., "Sructures of Three Lithium Ester Enolates by X-ray Diffraction; Derivation of Reaction Path for Cleavage into Ketene and Alcoholat", 1985, pp. 5403-5409, J. Am Chem. Soc., vol. 107.

Jackman, L. M. et al., "Structural Factors Controlling the Aggregation of Lithium Phenolates in Weakly Polar Aprotic Solvents", 1988, pp. 3829-3825, J. Am. Chem. Soc., vol. 110.

Brehon, M. et al., "Structural studies of lithiated enaminones; the 1-oxa-5-azapenta-dienyllithium fluxional heterocubane $[(Pr^iNCMeCHCMeOLi)_4]$ and its dimeric hexamethylphophoric triamide complex $[\{Pr^iNCMeCHCMeOLi \cdot OP(Nme_2)_3\}_2]$", 1997, 5 pgs., J. Chem. Soc., Dalton Trans.

Clegg, W. et al., "Lithiated organophosphorus enamines: a new synthetic approach and the first crystal structures", 1999, 2 pgs., Chem. Comm.

Boyle, T. J. et al., "Structural Diversity in Solvated Lithium Aryloxides. Snytheses, Characterization, and Structures of $[Li(Oar)(THF)_x]_n$ and $[Li(Oar)(py)_x]_2$ Complexes Where $Oar=OC_6H_5$, $OC_6H_4(2-Me)$, $OC_6H_3(2,6-(Me))_2$, $OC_6H_4(2-Pr^i)$, $OC_6H_3(2,6-(Pr^i))_2$, $OC_6H_4(2-Bu^t)$, $OC_6H_3(2,6-(Bu^t))_2$", 2000, pp. 5133-5146, Inorg. Chem. vol. 39.

Maetzke, T. et al., "X-ray Crystal Structure Analysis of an Octameric Lithium N-Isopropylbenzamide Aza Enolate Complex", 1990, pp. 3032-3037, Organometallics, vol. 9.

Ball, S. C. et al., "Dilithiated salen Complexes Chiral $[(salen)Li2 \cdot hmpa]2$ and Deliberate Partial hydrolusis to give $[(salen)Li2]3 \cdot Li2O \cdot 2tmen \cdot H2O$ [H2salen=N,N'-ethylenebis (salicylideneimine); hmpa=hexamethylphosphoramide; tmen=tetramethylenediamine]", 1995, pp. 2147-2149, J. Chem. Soc., Chem. Comm.

Hyvärinen, K. et al., "Synthesis and Crystal Structure of a Novel Multiple Bridged Cubane Type (Li4O3Cl)3 Lithium Carbonato Chloro HMPA Siloxane Complex, $[[Li_4(\mu_3Cl(\mu_6-Osi(CH_3)_2O(CH_3)_2SiO)(\mu-OP(N(CH_3)_2)_3)(OP(N(CH_3)_2)_3)]3(\mu_3-Cl)(\mu_3-Cl)(\mu_9-CO_3)] \cdot 2C_4H_8O$", 1996, pp. 2171-2177, Polyhedron, vol. 15, No. 13.

Barnett, N. D. et al., "Butyllithium Cubane Tetramers Linked by Li-TMEDA-Li Bridges in an Infinite, Zig-Zag Chain Arrangement: First Crystallographic Study of a Simple Butyl Compound of an Early Main Group Element", 1993, pp. 1573-1574, J. Am. Chem. Soc., vol. 115.

Henderson, K. W. et al., "Rational Design of Molecular Sheets Composed of Interconnecting Eight- and Twenty-Four-Membered Rings: Use of Lithiated Aggregates to Control Network Assembly", 2003, pp. 2839-2841, Inorganic Chem. Comm., vol. 42.

MacDougall, D. J. et al., "Use of tetrameric cubane aggregates of lithium aryloxides as secondary building units in controlling network assembly", 2005, pp. 456-458, Chem. Commun.

Oh, M. et al., "Megal-Mediated Self-Assembly of π-Bonded Benzoquinone Complexes into Polymers with Tunable Geometries", 2001, pp. 3191-3194, Angew. Chem. Int. Ed., vol. 40, No. 17.

Oh, M. et al., "The $\eta^4$-o-Benzoquinone Manganes Tricarbonyl Anion (o-QMTC) as an Organometalloligand in the Formation of M(o-QMTC)$_2$(L-L) Complexes (M=Mn, Co, Cd; L-L=bipy, phen): Generation of Neutral 2-D Networks Containing Two Types of π-π Stacking", 2003, pp. 1437-1442, Organometallics, vol. 22.

Fairhurst, G. et al., "Cyclopentadienyl- or Pentamethylcyclopentadienyl-(arene)cobalt(III) Complexes: Arene—Indole, Benzene, Mesitylene, Hexamethylbenzene, 1,4-Dihydroxy- and 1-Hydroxy-4-methoxytetramethylbenzene", 1979, pp. 1531-1538, J. Chem. Soc.

Whittall, I.R. et al., "Organometallic Complexes in Nonlinear Optics II . . . ," pp. 349-405, Adv. Organomet. Chem, vol. 43 (1999).

Lenaz G., Ed., Coenzyme Q: Biochemistry, Bioenergetics and Clinical Applications of Ubiquinone, 6 pages including title and table of contents, New York (1985).

* cited by examiner

| PRODUCT | BENZYLPROTON(ppm) | OTHER(ppm) | ARENE(ppm) | REF. |
|---|---|---|---|---|
| Ph-CH(OH)-Ph | 5.85(1H) | 2.20(OH,1H) | 7.48–7.05(10H) | 1 |
| Ph-CH(OH)-C6H4-OMe | 5.73(1H) | 3.74(Ome,3H)<br>2.51(OH,1H) | 7.30(5H)<br>7.22(2H),6.82(2H) | 1 |
| Ph-CH(OH)-mesityl | 6.32(1H) | 2.52(OH,1H)<br>2.28(3H)<br>2.23(6H) | 7.27–7.15(5H)<br>6.85(2H) | 2 |
| Ph-CH(OH)-C6H4-Me | 5.85(1H) | 2.56(OH,1H)<br>2.40(Me,3H) | 7.47–7.18(9H) | 1 |
| Ph-CH(OH)-C6H4-Cl | 5.60(1H) | 2.56(OH,1H) | 7.40–7.12(9H) | 1 |
| Ph-CH(OH)-C6H4-C6H5 | 5.73(1H) | 2.42(OH,1H) | 7.39–7.10(14H) | 2 |
| Ph-CH(OH)-C6H4-NO2 | 5.85(1H) | 2.66(OH,1H) | 8.00(2H),7.59(2H)<br>7.40(5H) | 3 |

1. Chen, D.-W.; Ochiai, M. *J Org Chem.* 1999, *64*, 6804.
2. Rudolf, J.; Schmidt, F.; Bolm, C. *Adv. Synth. Catal.* 2004, *346*, 867.
3. Strazzolini, P.; Giumanini, A. G.; Verardo, G. *Tetrahedron* 1994, *50*, 217

METHOD OF USING RHODIUM QUINONOID CATALYSTS

PRIORITY CLAIM

This application claims priority from U.S. Provisional Patent Application No. 60/740,762 filed on Nov. 30, 2005, the contents of which are hereby incorporated by reference.

STATEMENT OF GOVERNMENT RIGHTS

The invention was made in part under U.S. Government contract number NSF CHE-0308640. Accordingly, the Government has certain rights in this invention.

RELATED APPLICATION

The subject application shares certain attributes with co-pending application Ser. No. 11/454,760, entitled, Rhodium Quinonoid Catalysts, filed on even date herewith, the contents of which are hereby incorporated by reference in its entirety.

TECHNICAL FIELD

The invention concerns the use of hydroquinone catalysts.

BACKGROUND

In fields such as the development of pharmaceuticals, agrochemicals and in medicinal discovery chemistry, there is an unmet need for conjugate additions with electron deficient boronic acids and esters. Some recent advances in the development of transition-metal-catalyzed carbon-carbon bond-forming chemistries are reviewed in Rouhi, "Fine Chemicals", *Chemical & Engineering News*, Sep. 6, 2004, pages 49-67.

Additionally, few π-bonded hydroquinones are known. See Moussa, et al., "η5-Semiquinone Complexes and the η4-Benzoquinone of (Pentamethylcyclopentadienyl) rhodium and -irridium: Synthesis, Structures, Hydrogen Bonding, and Electrochemical Behavior", *Organometallics* 23: 6231-38 (2004) and Amouri, *Eur. J. Inorg. Chem.*, page 3808 (2005). For example, complexes containing 1,4-hydroquinone ($H_2Q$) π-bonded to a transition metal are of substantial interest because of the importance of quinonoid molecules in mediating proton and electron transfer reactions. See: Pierpont, C. G.; Langi, C. W. *Prog. Inorg. Chem.* 1994, 41, 331. Ebadi, M.; Lever, A. B. P. *Inorg. Chem.* 1999, 38, 467. *Coenzyme Q: Biochemistry, Bioenergetics and Clinical Applications of Ubiquinone*; Lenaz, G., Ed.; Wiley: New York, 1985.

Those skilled in the art desire new uses of hydroquinone complexes. Embodiments of the subject invention satisfy this need and others.

SUMMARY OF THE INVENTION

In accordance with an aspect of the invention, disclosed is a method of making an acyclic or cyclic compound comprising combining in a reaction mixture an aryl or vinylic boronic compound, a conjugate acceptor and a rhodium hydroquinone catalyst under suitable reaction conditions, allowing the reaction to proceed to its end, and isolating the desired acylic or cyclic compound from the reaction mixture.

In accordance with another aspect, a method comprises using the rhodium hydroquinone catalyst for the conjugate addition of a boronic substrate of the boronic compound comprising transferring a carbon group from the boronic compound to the conjugate acceptor via the rhodium hydroquinone catalyst; and forming a product of conjugate addition.

In accordance with another aspect, a method comprises combining the boronic compound, rhodium hydroquinone catalyst, conjugate acceptor and a solvent, wherein the boronic compound is an aryl boronic acid, the conjugate acceptor is enone and the solvent is dimethoxyethane; adding an aqueous solution of LiOH base followed by deoxygenated $H_2O$ to obtain a mixture; stirring the mixture at about 50° C. for about 1 hour; then diluting the mixture with a solution of $NH_4Cl$, extracted with EtOAc/hexanes and dried $Na_2SO_4$; followed by filtering to obtain the desired compound.

In accordance with another aspect, the above catalyst comprises the formula formula (I)

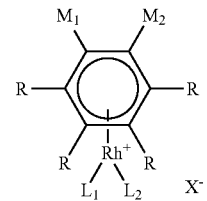

(I)

wherein $X^-$ is selected from the group consisting of $BF_4^-$, $SbF_6^-$, $PO_2F_2^-$, $PF_6^-$, $OTf^-$, $^-OTs$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$; $O_3SCF_2CF_2CF_2CF_3^-$;

wherein $OTf=O_3SCF_3^-$; $OTs=O_3SC_6H_4CH_3^-$; $R'CO_2^-$;

wherein R' is selected from the group consisting of hydrogen or an alkyl, aryl or carbon atom bearing three identical or non-identical substituents;

wherein $L_1$ and $L_2$ are each a ligand that donates electron density to rhodium to stabilize it;

wherein

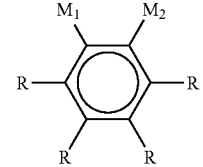

is either chiral or achiral and $M_1$ and $M_2$ comprise hydroxo (OH) groups in the ortho-, meta-, and para-positions and R is selected from the group consisting of H, C, O, N and S, with or without substituents, said substituents being identical or non-identical. $L_1$ and $L_2$ may also be identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

In accordance with a further aspect, the above catalyst comprises the formula

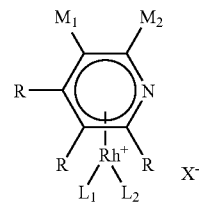

(II)

wherein $X^-$ is selected from the group consisting of $BF_4^-$, $SbF_6^-$, $PO_2F_2^-$, $PF_6^-$, $OTf^-$, $^-OTs$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$;

$O_3SCF_2CF_2CF_2CF_3^-$ wherein $OTf=O_3SCF_3^-$; $OTs=O_3SC_6H_4CH_3^-$; $R'CO_2^-$;

wherein R' is selected from the group consisting of hydrogen or an alkyl, aryl or carbon bearing three identical or non-identical substituents;

wherein $L_1$ and $L_2$ are each a ligand that donates electron density to rhodium to stabilize it;

wherein R is selected from the group consisting of H, C, O, N and S, with or without substituents, said substituents being identical or non-identical; and $L_1$ and $L_2$ may be identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

In accordance with a further aspect the catalyst comprises the formula

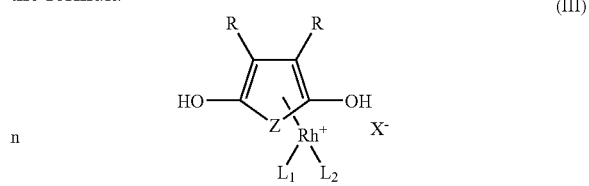

(III)

wherein Z is nitrogen, oxygen or sulfur;

wherein R is selected from the group consisting of H, C, O, N and S, with or without substituents, said substituents being identical or non-identical;

wherein $X^-$ is selected from the group consisting of $BF_4^-$, $SbF_6^-$, $PO_2F_2^-$, $PF_6^-$, $OTf^-$, $^-OTs$, $SO_4^{2-}$, $B(C_6F_5)_4^-$, $B(C_6H_5)_4^-$, $ClO_4^-$, $NO_3^-$, $NO_2^-$, $HOSO_3^-$, $CO_3^{2-}$, $O_3SCF_2CF_2CF_2CF_3^-$ wherein $OTf=O_3SCF_3^-$; $OTs=O_3SC_6H_4CH_3^-$; $R'CO_2^-$; and R' is selected from the group consisting of hydrogen or an alkyl, aryl or carbon bearing three identical or non-identical substituents;

wherein $L_1$ and $L_2$ are each a ligand that donates electron density to rhodium to stabilize it;

or formula (IV)

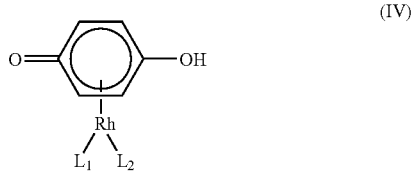

(IV)

wherein $L_1$ and $L_2$ are each a ligand that donates electron density to rhodium to stabilize it;

or formula (V)

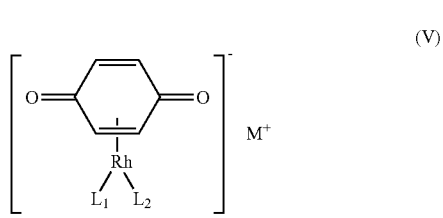

(V)

wherein $L_1$ and $L_2$ are each a ligand that donates electron density to rhodium to stabilize it;

wherein $M^+$ is a positively charged ion including any metal ion having an oxidation state at or higher than +1. $M^+$ is selected from the group consisting of cationic Li, K, Cs, Be, Sr, Ba, Al, Ti, Zr, B, Si, Cd, Ag, $Ph_3PNPPh_3$, Rb, $Mg^{2+}$, $Ca^{2+}$, Na, $R_4N^+$, $Zn^{2+}$, ammonium salts including tetraalkylammonium cations, tetraalkylarsonium cations, guanidinium salts, amidinium salts, and combinations thereof; and $L_1$ and $L_2$ are identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

In accordance with further aspects, the catalyst comprises 1,2-, 1,3- or 1,4-hydroquinone α-bonded to rhodium, and may further comprise $[1,4\text{-(hydroquine)Rh(COD)}]^+$ cation or $1,3\text{-(hydroquine)Rh(COD)}]^+$ cation, wherein COD is cyclooctadiene.

In accordance with further aspects, the catalyst comprises 1,2-hydroquinone, 1,3-hydroquinone or 1,4-hydroquinone π-bonded to $Rh(P(OPh)_3)_2^+$ cation.

In accordance with another aspect, the method comprises a reaction:

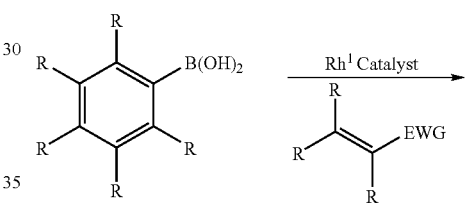

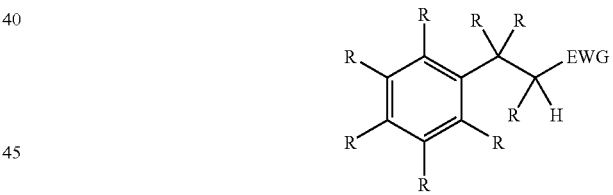

wherein the reaction comprises providing an active rhodium hydroquinone catalyst, $Rh^1$, and reacting the catalyst with the boronic compound comprising a sp2 hybridized carbon-center bearing a boron to transfer the sp2 hybridized carbon to rhodium and subsequently to the conjugate acceptor, which is an electron deficient olefin, an olefin bearing one or more electron withdrawing groups (EWG), through carbo-metallation followed by proto-demetallation in a presence of a base;

wherein EWG is selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; and R is selected from the group consisting of hydrogen, carbon, halide, oxygen, sulfur, nitrogen, silicon, phosphorus, sulfur, selenium, and combinations thereof.

In accordance with another aspect, a method comprises the reaction:

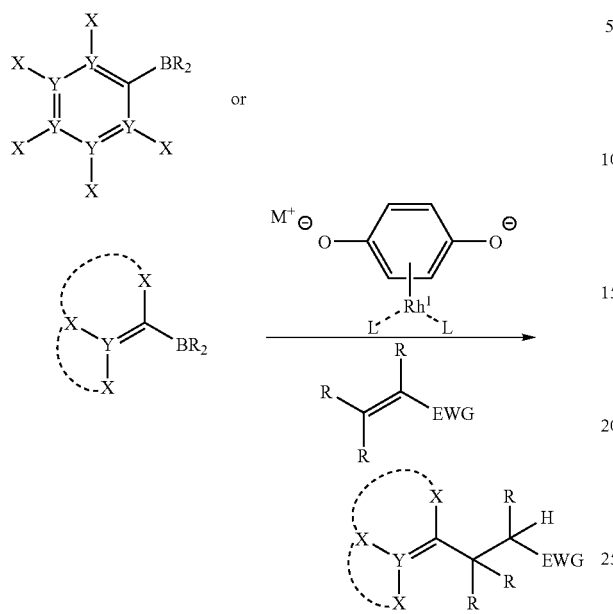

wherein the reaction comprises providing the boronic compound and the catalyst and reacting the compound and catalyst under conditions sufficient to cause the reaction, X is selected from the group consisting of hydrogen, carbon, halide, oxygen, sulfur, nitrogen, silicon, phosphorus, sulfur, selenium, and combinations thereof.

$M^+$ is a positively charged ion including any metal ion having an oxidation state at or higher than +1, and is selected from the group consisting of cationic Li, K, Cs, Be, Sr, Ba, Al, Ti, Zr, B, Si, Cd, Ag, $Ph_3PNPPh_3$, Rb, $Mg^{2+}$, $Ca^{2+}$, Na, $R_4N^+$, $Zn^{2+}$, ammonium salts including tetraalkylammonium cations, tetraalkylarsonium cations, guanidinium salts, amidinium salts, and combinations thereof;

Y is selected from the group consisting of hydrogen, carbon, halide, oxygen, sulfur, nitrogen, silicon, phosphorus, sulfur, selenium, and combinations thereof;

L is a ligand that donates electron density to the rhodium to stabilize it and each L is an identical or non-identical ligand that is either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitrites, and combinations thereof;

wherein EWG is selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; R is selected from the group consisting of hydrogen, carbon, halide, oxygen, sulfur, nitrogen, silicon, phosphorus, sulfur, selenium, and combinations thereof; and —$BR_2$ is any boronic containing species neutral or anionically charged where boron is bound to a transfer group.

In accordance with a further aspect, disclosed is a reagent for the conjugate addition of aryl or vinylic boronic acids wherein the reagent comprises a rhodium hydroquinone catalyst.

Another aspect comprises using the rhodium hydroquinone catalyst for the conjugate addition of boronic acid comprising a reaction:

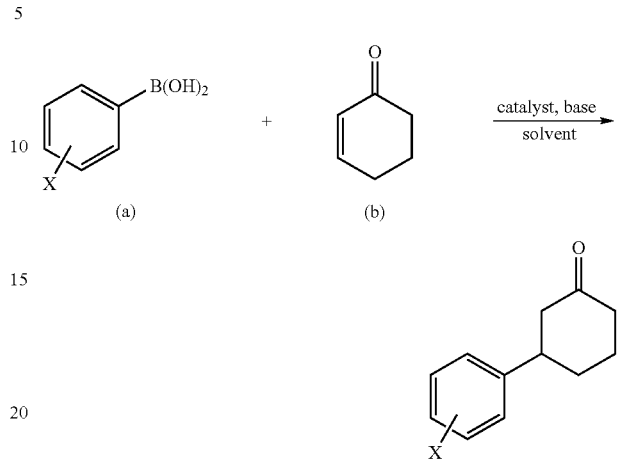

wherein the reaction comprises mixing reagents (a) and (b) and reacting the reagents and the rhodium hydroquinone catalyst under conditions sufficient to cause the reaction in the presence of a base and a solvent, wherein:

X is selected from the group consisting of p-Me, m-$NO_2$, H, o-Me, 4NH-Boc, p-OMe, p-Cl, p-F, 3Cl,4F, m-$NO_2$, 3,4,5 triF, 2,3,4-triF;

the solvent is selected from the group consisting of DME/$H_2O$, $H_2O$ and THF; and the base is LiOH or KOH.

A further aspect comprises using a rhodium hydroquinone catalyst for the conjugate addition of aryl boronic acid to 2-cyclohexen-1-one comprising a reaction

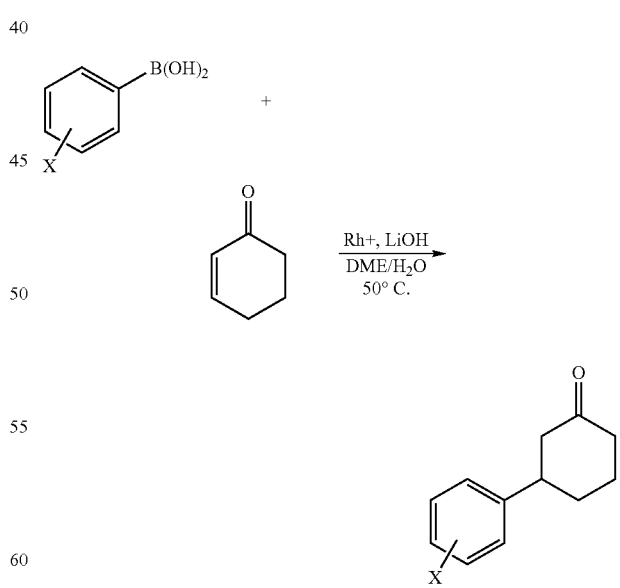

wherein:

Rh+ is the catalyst; and

X is selected from the group consisting of p-Me and m-$NO_2$.

In accordance with another aspect, a method comprising a reaction:

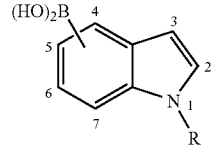

(a)

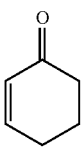

(b)

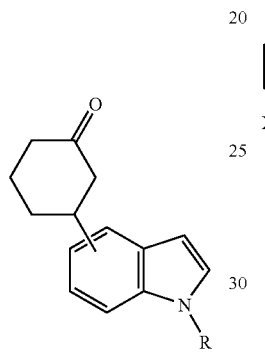

wherein the reaction comprises mixing reagents (a) and (b) and reacting the reagents with a catalyst in the presence of a base and a solvent under conditions sufficient to cause the reaction, wherein:

R is selected from the group consisting of H and Boc;

the catalyst is a rhodium quinone catalyst; the solvent is selected from the group consisting of DME/H$_2$O and THF; and the base is LiOH.

Also disclosed according to a further aspect is a method for double deprotonation of a rhodium hydroquinone catalyst to active quinone complex 3.K comprising a reaction:

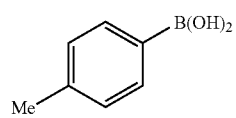

1.2 equiv.
(a)

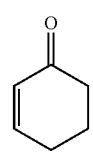

1.0 equiv.
(b)

2.5-3.0 mol% 3-k
H$_2$O/DME (1.5:1)
50° C.
91-94%

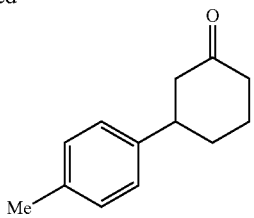

wherein the reaction comprises mixing reagents (a) and (b) and reacting the reagents and the catalyst in the presence of water and DME under conditions sufficient to cause the reaction.

Still further disclosed is a method comprising a reaction

Rh+, LiOH
DME/H$_2$O
50° C.

wherein:

Rh+ is a rhodium hydroquinone catalyst; and

X is selected from the group consisting of: H, p-Me, o-Me, 4NH-Boc, p-OMe, p-Cl, p-F, 3Cl,4F, m-NO$_2$, 3,4,5 triF, 2,3, 4-triF.

Also disclosed is a method of using a catalyst for the conjugate addition of aryl or vinyl boronic substrates comprising the steps of: a) providing a rhodium hydroquinone catalyst; b) transferring a sp2 hybridized carbon group from boron to a conjugate acceptor via the catalyst; and c) forming a product of conjugate addition.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein:

FIG. 5 shows $^1$H NMR data of diaryl alcohols obtained using the rhodium quinonoid catalyst;

DETAILED DESCRIPTION

Figures 1, 2:
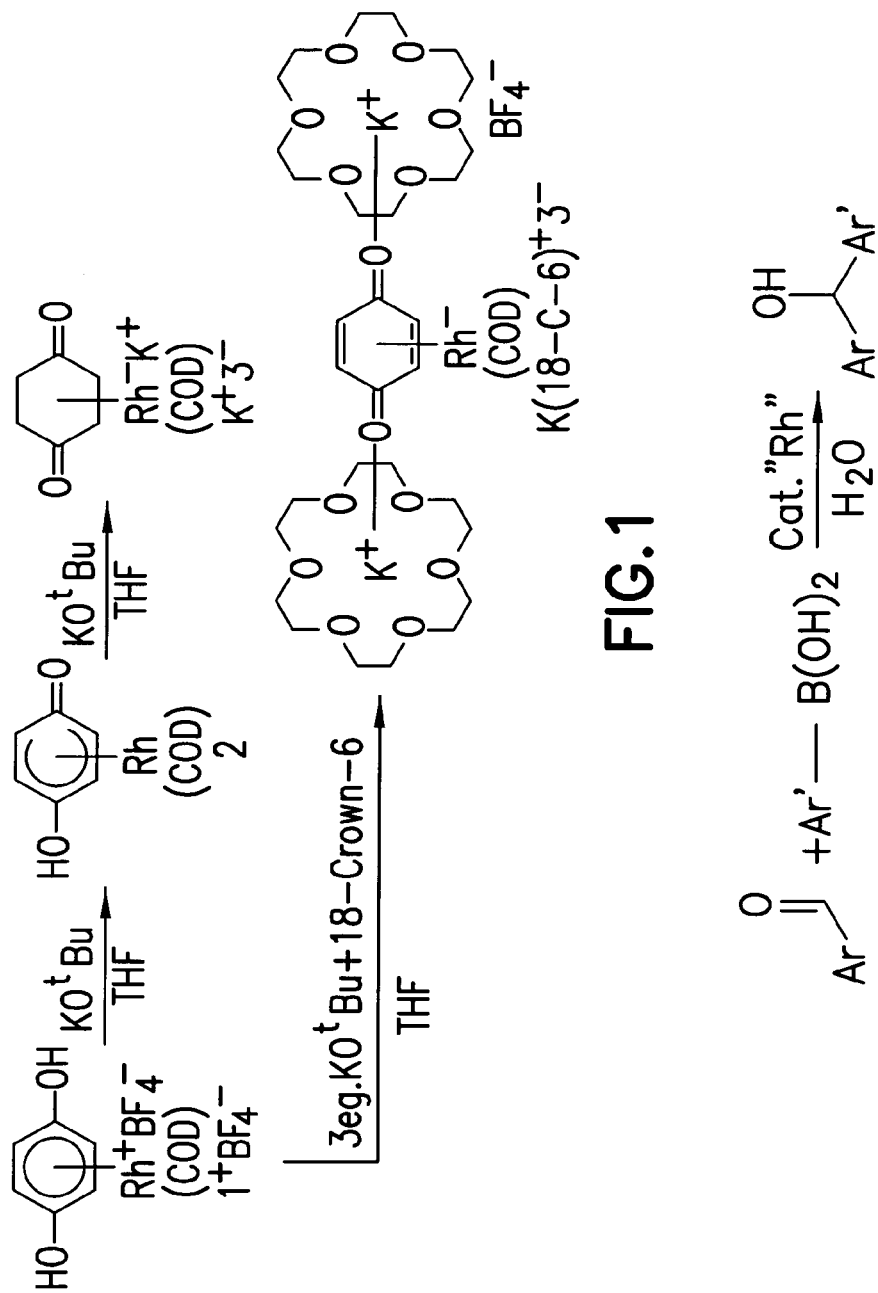
FIG. 1. shows deprotonation and concomitant oxidation of hydroquinonone to quinone with the 7r-bonded metal fragment acting as an internal electron acceptor.
FIG. 2. shows catalytic arylation of benzaldehydes.

Non-limiting embodiments of the invention are further described below. However, it should be appreciated that some of the features of embodiments of the invention could be used to advantage without the corresponding use of other features. As such, the foregoing description should be considered as merely illustrative of the principles of the invention, and not in limitation thereof. Further, one skilled in the art will appreciate that the invention can be practiced by other than the described embodiments; that these described embodiments are presented for the purposes of illustration and not of limitation. For example, while various substituents are noted herein, other substituents known to those of skill in the art may also be employed in the compounds and formulas referenced herein.

By way of introduction, there is a great need for efficient catalysts in carbon-carbon coupling reactions of boronic acid derivatives (in general synthesis, pharmaceuticals, etc.) and for coupling monomers to give polymers. Due to the unique mechanism provided by the synergistic action of the rhodium and quinone components described herein, the rhodium quinone catalysts promote reactions at a higher level of efficiency than previously available with non-quinone catalysts.

Advantageously, embodiments of the invention provide enhanced yields of conjugate addition products via the use of rhodium hydroquinone catalysts. Details of processing steps for the conjugate addition of aryl- and vinyl-boronic compounds to conjugate addition accepts are set forth in detail below. Examples of compounds and reactions are provided, along with reaction results.

Accordingly, embodiments of the invention are directed to uses and processes for the conjugate addition of aryl- and vinyl-boronic compounds (e.g. esters, boronic acids and boroxines) to cyclic and acyclic conjugate addition acceptors, including but not limited to, vinyl-nitro compounds; α,β-unsaturated amides, anhydrides, esters, thioesters, aldehydes and ketone; and vinyl-sulfones. It has been demonstrated that the use of the novel cationic hydroquinone-Rh complex set forth in the afore-reference application entitled "Rhodium Quinonoid Catalysts" and described herein provides a superior catalytic system than those believed to be currently reported in the literature.

Thus, an embodiment of the invention comprises the process:

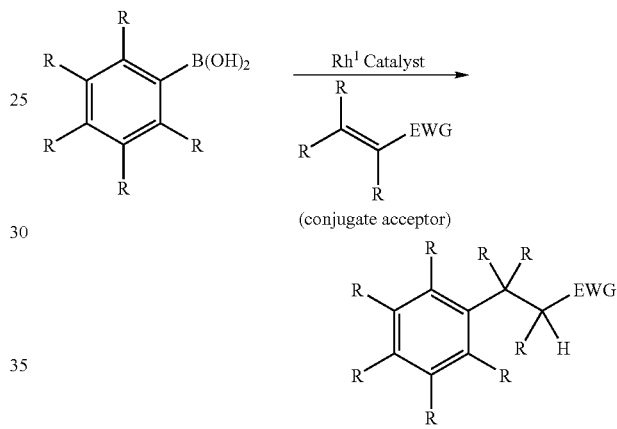

wherein EWG may be selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; and R may be selected from the group consisting of hydrogen, carbon, halide, oxygen, sulfur, nitrogen, silicon, phosphorus, sulfur, selenium or other suitable atom, and combinations thereof. These we term "conjugate acceptors" thus referring to an alkene or olefin with an electron withdrawing group (EWG).

A majority of experiments found in literature show that electron-deficient aryl boronic acids can provide poor yield of the desired addition product while requiring vast excess (3-10+ equiv) of the boronic acid for these results. Some other reports appear to give no results for electron poor systems and only report electron rich ones.

In contrast, the novel rhodium catalyst system has been demonstrated to be highly active and provide good amounts of the desired conjugate addition product with exceptionally low catalyst loadings (about 0.5-1.0 mol % Rh$^1$ catalyst) even with strongly electron withdrawing group present on the aromatic ring (3 fluorines meta, meta and para attempted and was successful).

Thus, in accordance with an embodiment of the invention, the process may comprise:

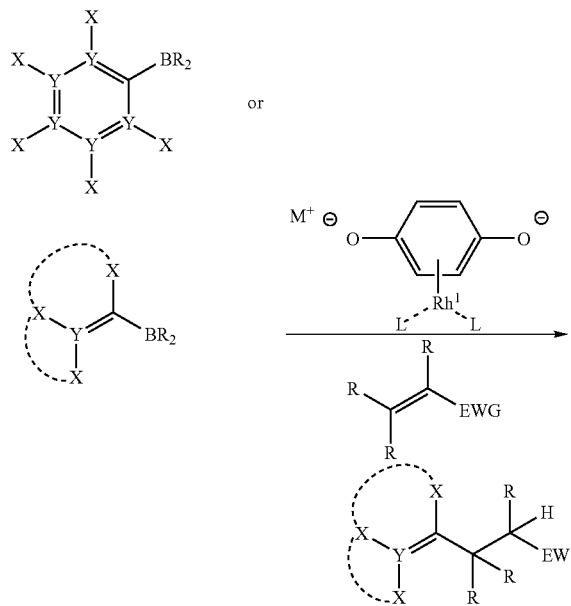

M = Li, K, Cs, Rb, Mg²⁺, Ca²⁺, Na, R₄N⁺, Zn²⁺

EWG = -NO₂, -SO₂R, -C(O)R, -C(O)NR₂, -C(O)OR, -C(O)SR

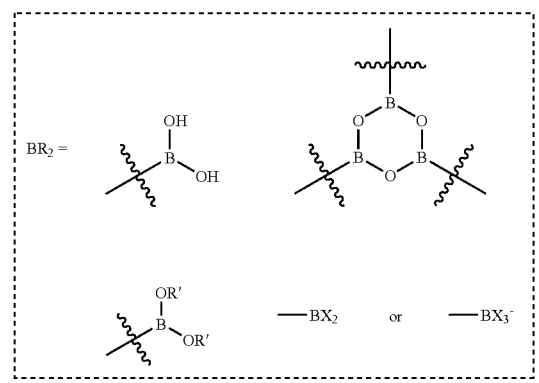

L = alkenes; phosphines and phosphites; sulfides, sulfoxides, sulfonates, sulfonamides and sulfones; ethers, amines, imines, amides, aldehydes, ketones, esters, and nitriles in any combination Accordingly, X may be selected from the group consisting of hydrogen, carbon, halide, oxygen, sulfur, nitrogen, silicon, phosphorus, sulfur, selenium or other suitable group, and combinations thereof.

M⁺ is a positively charged ion including any metal ion having an oxidation state at or higher than +1, and may also be selected from the group consisting of cationic Li, K, Cs, Be, Sr, Ba, Al, Ti, Zr, B, Si, Cd, Ag, Ph₃PNPPh₃, Rb, Mg²⁺, Ca²⁺, Na, R₄N⁺, Zn²⁺, ammonium salts including tetraalkylammonium cations, tetraalkylarsonium cations, guanidinium salts, amidinium salts, or other suitable counter-ions, and combinations thereof;

Y may be selected from the group consisting of hydrogen, carbon, halide, oxygen, sulfur, nitrogen, silicon, phosphorus, sulfur, selenium or other suitable group, and combinations thereof;

L is a ligand that donates electron density to the rhodium to stabilize it and each L shown above may be identical or non-identical ligands that are either chiral or achiral and may be selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles or other ligands, and combinations thereof;

wherein EWG may be selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; and R may be selected from the group consisting of hydrogen, carbon, halide, oxygen, sulfur, nitrogen, silicon, phosphorus, sulfur, selenium or other suitable atom, and combinations thereof; and —BR₂ may be any boronic containing species neutral or anionically charged where boron is bound to a transfer group, and includes for example boronic acid, boroxime, boronic ester, boron-ate complex or other suitable species, and combinations thereof.

As shown by the above reaction, the rhodium catalyst promotes the transfer of the substituent attached to the boron (—BR₂) to the electron deficient olefin to give the product of conjugate addition.

The above starting materials represent a class of boron containing substrates where the carbon that is transferred can be sp2. The carbon may be part of ring, e.g., a cyclic alkene, aromatic structure or heterocycle and may also be acyclic, e.g., an olefin or other suitable group.

Some representative examples of structures defining the conjugate acceptor include:

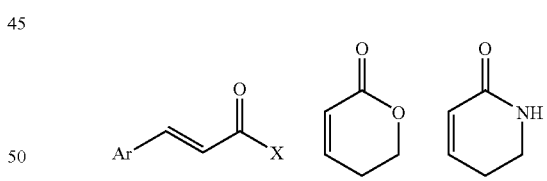

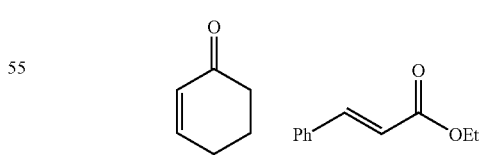

where X=H, O, N, C, S or other suitable group.

As a further specific example of an embodiment of the inventive process and as shown below, whereby an aryl boron species is added in a conjugate addition to an electron deficient olefin (in this depicted case: 2-cylcohexen-1-one).

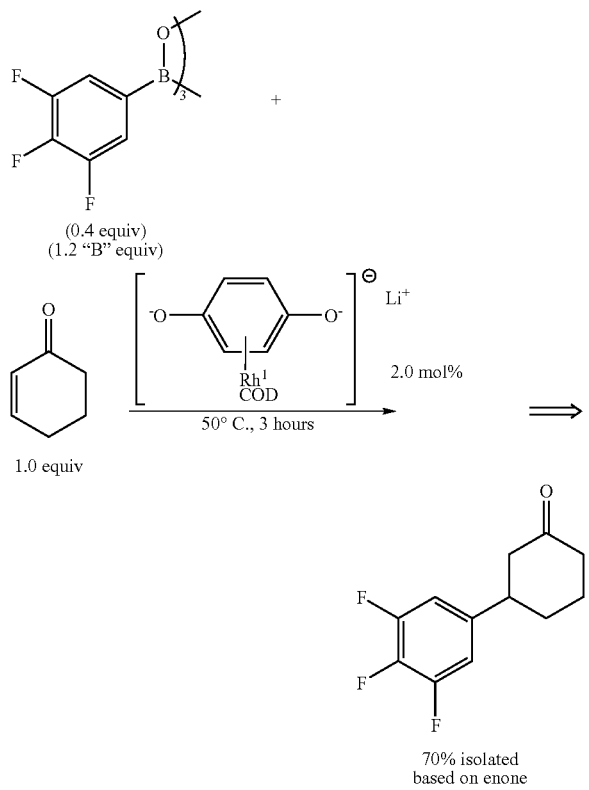

70% isolated based on enone

The enone, boron compound and Rh+ complex may be combined in DME, then LiOH (aq. 1 M) may be added. The reaction mixture may be diluted with DME and water and heated until the reaction is complete.

Improvements of the embodiments of the inventive process in comparison to the use of alternative catalyst systems include in situ generation of the active catalyst from a stable precursor, alternate solvent system and reduced temperature profile. Additional advantages include the high isolated yields of product employing extremely electron deficient aromatic boronic acids (such as tri-halogenated examples) while maintaining low catalyst loadings (0.5 mol % Rh), short reaction times and mild temperatures (50° C.).

Additional advantages include reduced catalyst loading, reduced boronic acid loading and increased scope of useful boronic acids, differing metal salt and alternative substrate scope.

Further details regarding the preferred, novel rhodium quinonoid complex and processing thereof are set forth below. For ease of reference, the following sections are set forth as I-III.

I. An Anionic Rhodium $\eta^4$-Quinonoid Complex as a Multifunctional Catalyst for the Arylation of Aldehydes with Arylboronic Acids Hydroquinone has been coordinated in a $\eta$-bonded $\eta^6$-manner to the metal fragments $Cr(CO)_3$, $Mn(CO)_3^+$, and $Cp^*M^{2+}$ (M=Rh, Ir). See: Huang, Y.-S.; Sabo-Etienne, S.; He, X.-D.; Chaudret, B. *Organometallics* 1992, 11, 303. Koelle, U.; Weisschädel, C.; Englert, U. *J. Organomet. Chem.* 1995, 490, 101. Schumann, H.; Arif, A. M.; Richmond, T. G. *Polyhedron* 1990, 9, 1677. Sun, S.; Carpenter, G. B.; Sweigart, D. A. *J. Organomet. Chem.* 1996, 512, 257. Le Bras, J.; Amouri, H.; Vaissermann, J. *Organometallics* 1998, 17, 1116. Oh, M.; Carpenter, G. B.; Sweigart, D. A. *Organometallics* 2002, 21, 1290. Moussa, J.; Guyard-Duhayon, C.; Herson, P.; Amouri, H.; Rager, M. N.; Jutand, A. *Organometallics* 2004, 23, 6231. Fairhurst, G.; White, C. *J. Chem. Soc., Dalton Trans.* 1979, 1531. An important chemical property displayed by some of these complexes is facile deprotonation of the —OH groups, which is accompanied by electron transfer to the metal and changes in the hapticity of the quinonoid ring. See, e.g., Sun et al., and Oh et al. above.

The foregoing is illustrated in FIG. 1 for the new $\eta^6$-$H_2Q$ complex [(1,4-hydroquinone)Rh(COD)]$BF_4$ ($1^+BF_4^-$), synthesized in 74% isolated yield by the reaction of [Rh(COD)Cl]$_2$ with AgBF$_4$ and H$_2$Q. $1^+BF_4^-$ cleanly undergoes deprotonation to afford stable neutral semiquinone (2) and anionic quinone ($3^-$) complexes.

With a catalytically-active metal such as rhodium, it was thought that the ability to alter the charge on the metal center by simple reversible deprotonation at the quinonoid center may constitute a powerful way to tune catalytic activity. In addition, the anionic doubly deprotonated $\eta^4$-quinone complex $3^-$ may be able to function as a ligand ("organometalloligand"), thereby offering the possibility of bifunctional activation of appropriate substrates by simultaneous interaction at the rhodium and quinonoid centers. The ability of a quinone complex to function as an organometalloligand has been demonstrated in the case of ($\eta^4$-benzoquinone)Mn(CO)$_3^-$. See: Oh, M.; Carpenter, G. B.; Sweigart, D. A., *Acc. Chem. Res.* 2004, 37, 1.

Catalysts able to operate in a bifunctional manner are of considerable current interest. See: Casey, C. P.; Johnson, J. B.; Singer, S. W.; Cui, Q. *J. Am. Chem. Soc.* 2001, 123, 11594. Mermerian, A. H.; Fu, G. C. *J. Am. Chem. Soc.* 2003, 125, 4050. Herein it is demonstrated that the hydroquinone complex $1^+BF_4^-$ is a convenient precursor to $M^+3^-$, where $M^+$ can be any of a variety of cations such as an alkali metal or tetraalkylammonium cation or other suitable cation known to those knowledgeable in the art, which serves as a catalyst for the coupling of arylboronic acids and benzaldehydes to produce diaryl alcohols (see FIG. 2). It is shown that $M^+3^-$ acts in a multifunctional manner by simultaneously activating both the boronic acid and the aldehyde, the former by coordination of a quinonoid oxygen in $3^-$ to the boron and the latter through a Lewis acid interaction among the aldehyde, the counterion $M^+$ and a quinonoid oxygen.

Figure 3:
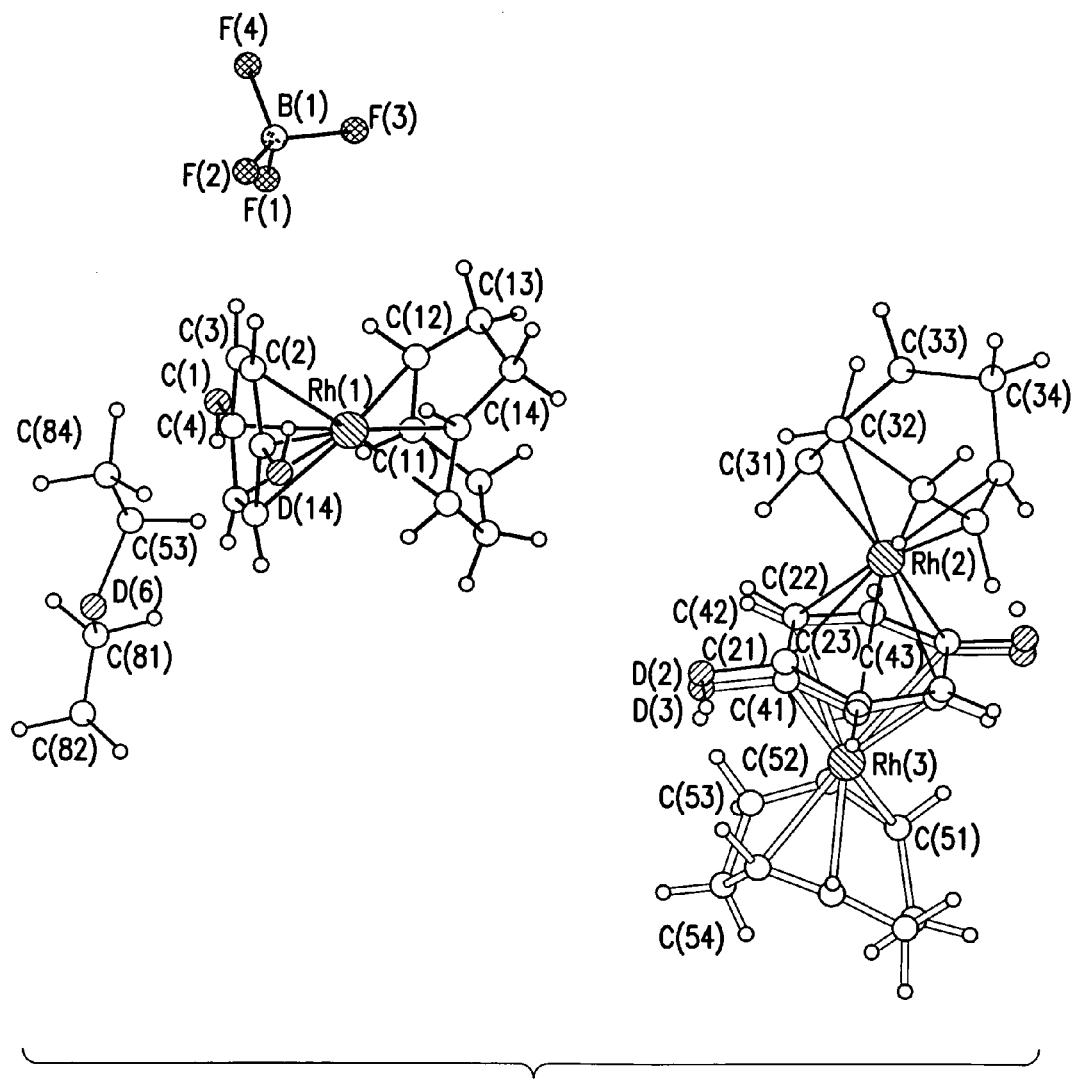
FIG. 3 is a photographic reproduction of an X-ray crystallography showing the structure of an embodiment of the rhodium species.

The X-ray structure of [(H$_2$Q)Rh(COD)]BF$_4$.Et$_2$O ($1^+BF_4^-$) established the anticipated $\eta^6$-bonding mode. The structure obtained from X-ray analysis is shown in FIG. 3. The solid state structure of $1^+BF_4^-$ displays several types of crystallographic disorder, but the connectivity and chemical structure indicated is certain; the structure was solved to a acceptable R1 factor of 8.9%.

Deprotonation of $1^+BF_4^-$ with KO$^t$Bu in THF (tetrahydrofuran) occurred readily to afford the semiquinone (2) and the quinone (K$^+3^-$) analogues (FIG. 1). X-ray quality crystals of K$^+3^-$ could not be grown, but the butylammonium salt was readily obtained by metathesis and its X-ray structure determined as Bu$_4$N$^+$[(1,4-Q)Rh(COD)]$^-$.3 Bu$_4$NBF$_4$. The Rh—C bond lengths clearly indicated an $\eta^4$-bonding mode, with the quinone Rh—C distances being ca. 0.2 Å greater for the C(O) carbons in comparison to the other four quinone carbons. Deprotonation of $1^+BF_4^-$ with KO$^t$Bu in the presence of 18-crown-6 produced the salt K(18-C-6)$^+$[(1,4-Q)Rh(COD)]$^-$. K(18-C-6)BF$_4$, in which each quinone oxygen is linked to a crown ether encapsulated potassium ion (FIG. 1). It is noted that X-ray data for this salt were of moderate quality, but sufficient to establish the connectivity shown and establish that the indicated structure is correct.

The cross-coupling of organoborates and organic electrophiles has become an important synthetic tool in organic chemistry. See: Suzuki, A. *Acc. Chem. Res.* 1982, 15, 178. Miyaura, N.; Suzuki, A. *Chem. Rev.* 1995, 95, 2457. While palladium is often used as the transition metal in the catalyst for this reaction, rhodium can also be effective. Especially noteworthy are the rhodium-catalyzed addition of arylboronic acids to aldehydes and the 1,4-addition of arylboronic acids to enones. See, respectively, (1) Sakai, M.; Ueda, M.; Miyaura, N. *Angew. Chem. Int. Ed.* 1998, 37, 3279. Ueda, M.; Miyaura, N. *J. Org. Chem.* 2000, 65, 4450. Fürstner, A.; Krause, H. *Adv. Synth. Catal.* 2001, 343. Pucheault, M.; Darses, S.; Genet, J. P. *J. Am. Chem. Soc.* 2004, 126, 15356; (2) Takaya, Y.; Ogasawara, M.; Hayashi, T. *J. Am. Chem. Soc.* 1998, 120, 5579. Batey, R. A.; Thadani, A. N.; Smil, D. V. *Org. Lett.* 1999, 1, 1683. Ramnauth, J.; Poulin, O.; Bratovanov, S. S.; Rakhit, S.; Maddaford, S. P. *Org. Lett.* 2001, 3, 2571. Kuriyama, M.; Nagai, K.; Yamada, K.; Miwa, Y.; Taga, T.; Tomioka, K. *J. Am. Chem. Soc.* 2002, 124, 8932. (e) Hayashi, T.; Takahashi, M.; Takaya, Y.; Ogasawara, M. *J. Am. Chem. Soc.* 2002, 124, 5052. Yoshida, K.; Ogasawara, M.; Hayashi, T. *J. Am. Chem. Soc.* 2002, 124, 10984. Itooka, R.; Iguchi, Y.; Miyaura, N. *J. Org. Chem.* 2003, 68, 6000. Duursma, A.; Boiteau, J.-G.; Kefort, L.; Boogers, J. A. F.; de Vries, A. H. M.; de Vries, J. G.; Minnaard, A. J.; Fering a, B. L. *J. Org. Chem.* 2004, 69, 8045. The results obtained for arylboronic acid addition to benzaldehydes as catalyzed by rhodium quinone complexes are given in Table 1.

An inspection of the data in Table 1 shows some remarkable behavior. From entries 1-6 it is shown that the cationic rhodium hydroquinone complex $1^+BF_4^-$ had catalytic activity when a base (KOH) is present. Addition of the neutral salt $1^+BF_4^-$ had no effect (entry 5). It is concluded that the base likely functions to deprotonate the—quinonoid —OH groups. In agreement with this, the anionic quinone complex $K^+3^-$ was found to be a very effective catalyst, giving high yields at 75° C. or higher temperatures. Interestingly, the yield drops dramatically when a crown ether is added to the reaction mixture or when $K(18-C-6)^+3^-$ is used as the catalyst in place of $K^+3^-$ (entries 13, 15). In a similar vein, the activity is reduced by the inclusion of n-$Bu_4N^+BF_4^-$ (entries 14, 16). Likely related to this is the observation that $Li^+3^-$ is a more effective catalyst than $K^+3^-$, as indicated by entries 10 and 12 compared to 17 and 18. This behavior clearly signals heterobimetallic or dual function catalysis in which the alkali metal $Li^+$ or $K^+$ enhances the electrophilic activation of the aldehyde carbon by interacting with the carbonyl oxygen, thus facilitating aryl transfer from the rhodium catalyst. See: Sammis, G. M.; Danjo, H.; Jacobsen, E. N. *J. Am. Chem. Soc.* 2004, 126, 9928. Shibasaki, M.; Yoshikawa, N. *Chem. Rev.* 2002, 102, 2187. Yamagiwa, N.; Matsunaga, S.; Shibasaki, M. *J. Am. Chem. Soc.* 2003, 125, 16178. Li, C.; Eidjaja, E.; Garland, M. *J. Am. Chem. Soc.* 2003, 125, 5540. Guo, N.; Li, L.; Marks, T. J. *J. Am. Chem. Soc.* 2004, 126, 6542. Comte, V.; Le Gendre, P.; Richard, P.; Moïse, C. *Organometallics* 2005, 24, 1439. This hypothesis is in accord with the reduced reactivity that is found when the alkali metal is chelated with a crown ether or replaced with the much larger n-$Bu_4N^+$ ion.

See Table 1 below setting forth results of the rhodium-catalyzed arylation of ArCHO with Ar'B(OH)$_2$ in water solvent.

TABLE 1

Results for Rhodium-Catalyzed Arylation of Aldehydes

| entry | aldehyde | catalyst | additives (eq) | T/° C. | time (h) | yield (%)[b] |
|---|---|---|---|---|---|---|
| 1 | $C_6H_5CHO$ | $1^+BF_4^-$ | none | 95 | 3 | NR[c] |
| 2[d] | $C_6H_5CHO$ | $1^+BF_4^-$ | none | 95 | 3 | NR |
| 3 | $C_6H_5CHO$ | $1^+BF_4^-$ | none | 75 | 3 | NR |
| 4 | $C_6H_5CHO$ | $1^+BF_4^-$ | KOH (1.2) | 75 | 3 | 97 |
| 5 | $C_6H_5CHO$ | $1^+BF_4^-$ | $K^+BF_4^-$ (1.2) | 75 | 3 | NR |
| 6 | $C_6H_5CHO$ | $1^+BF_4^-$ | none | 50 | 16 | NR |
| 7 | $C_6H_5CHO$ | $K^+3^-$ | none | 95 | 3 | 96 |
| 8 | $C_6H_5CHO$ | $K^+3^-$ | none | 75 | 3 | 93 (90) |
| 9 | $C_6H_5CHO$ | $K^+3^-$ | none | 60 | 3 | 81 |
| 10 | $C_6H_5CHO$ | $K^+3^-$ | none | 50 | 3 | 48 |
| 11 | $C_6H_5CHO$ | $K^+3^-$ | none | 50 | 16 | 84 |
| 12 | $C_6H_5CHO$ | $K^+3^-$ | none | 25 | 16 | 19 |
| 13 | $C_6H_5CHO$ | $K^+3^-$ | 18-C-6 (0.075) | 75 | 3 | 14 |
| 14 | $C_6H_5CHO$ | $K^+3^-$ | n-$Bu_4N^+BF_4^-$ (0.075) | 75 | 3 | 24 |
| 15 | $C_6H_5CHO$ | $K^+(18-C-6)3^-$ | none | 75 | 3 | 13 |
| 16 | $C_6H_5CHO$ | n-$Nu_4N^+3^-$ | none | 75 | 3 | 2 |
| 17 | $C_6H_5CHO$ | $Li^+3^-$ | none | 50 | 3 | 96 (91) |
| 18 | $C_6H_5CHO$ | $Li^+3^-$ | none | 25 | 16 | 40 |
| 19 | $C_6H_5CHO$ | $[Rh(COD)Cl]_2$ | none | 75 | 3 | NR |
| 20 | $C_6H_5CHO$ | $[Rh(COD)_2]^+BF_4^-$ | none | 75 | 3 | NR |
| 21 | $C_6H_5CHO$ | $[Rh(COD)_2]^+BF_4^-$ | KOH (0.025) | 75 | 3 | 1 |
| 22 | $C_6H_5CHO$ | $[Rh(COD)_2]^+BF_4^-$ | KOH (1.2) | 75 | 3 | 99 |
| 23 | $C_6H_5CHO$ | none | KOH (1.2) | 75 | 3 | NR |
| 24 | 4-$MeOC_6H_4CHO$ | $K^+3^-$ | none | 75 | 3 | 81 (78) |
| 25 | 2,4,6-$Me_3C_6H_2CHO$ | $K^+3^-$ | none | 75 | 3 | 69 (68) |
| 26 | 4-$MeC_6H_4CHO$ | $K^+3^-$ | none | 75 | 3 | 99 (97) |
| 27 | 4-$ClC_6H_4CHO$ | $K^+3^-$ | none | 75 | 3 | 99 (97) |
| 28 | 4-$PhC_6H_4CHO$ | $K^+3^-$ | none | 75 | 3 | 98 (93) |
| 29 | 4-$O_2NC_6H_4CHO$ | $K^+3^-$ | none | 75 | 3 | 99 (92) |
| 30[e] | $C_6H_5CHO$ | $K^+3^-$ | none | 75 | 3 | 96 (91) |
| 31[f] | $C_6H_5CHO$ | $K^+3^-$ | none | 75 | 3 | 94 (90) |
| 32[g] | $C_6H_5CHO$ | $K^+3^-$ | none | 75 | 3 | 20 |
| 33[h] | $C_6H_5CHO$ | $K^+3^-$ | none | 75 | 3 | 2 |

Figure 4:
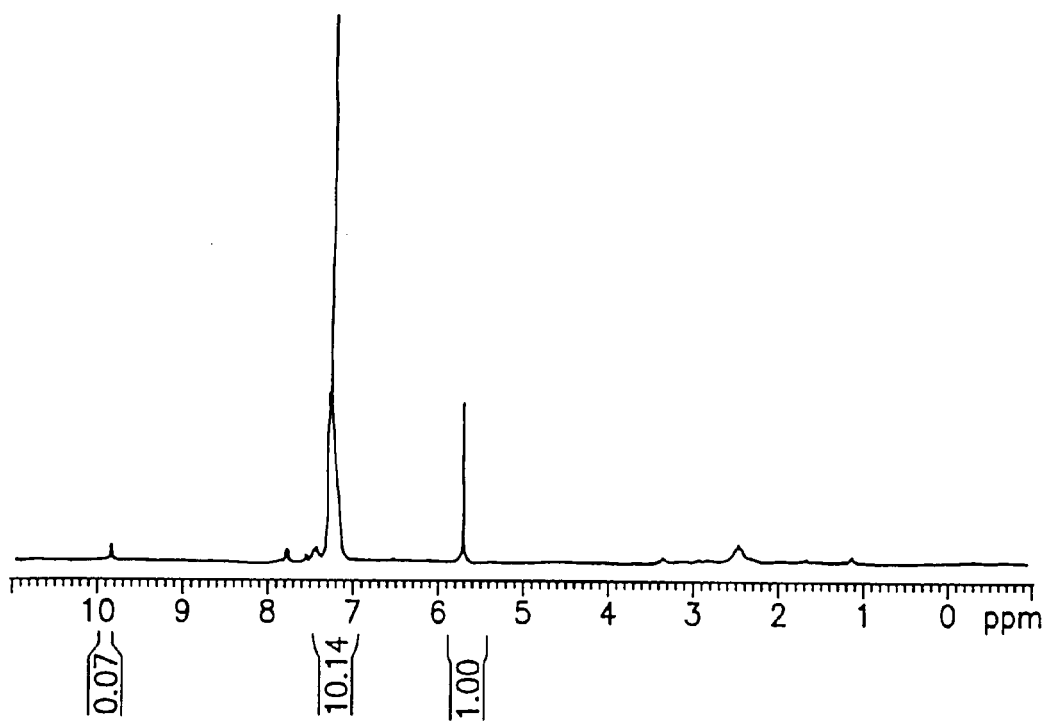
FIG. 4 shows the $^1$H NMR spectrum of diphenyl alcohol, the product of the rhodium-quinonoid catalyzed addition of phenyl boronic acid to benzaldahyde.

Entries 7 and 30-33 show that electron-withdrawing para-substituents on the aryl group in Ar'B(OH)$_2$ hinder the reaction, as has been found with other catalyst systems. See: Sakai, M.; Ueda, M.; Miyaura, N. *Angew. Chem. Int. Ed.* 1998, 37, 3279. Table 1 also indicates that the catalytic conditions are tolerant of a wide range of aryl substituents in the aldehyde reactant (entries 8 and 24-29). See also FIGS. 4 and 5, which present typical proton NMR data for the products of the arylation reactions.

Suzuki-Miyaura and Miyaura-Hiyashi type coupling reactions involving boronic acids are usually facilitated by the presence of stoichiometric external base (e.g., compare entries 20 and 22). It has been debated whether the base serves to increase the rate of transmetallation from boron to the transition metal catalyst by binding to the former or by binding to the latter. Recent theoretical studies suggest that the hard base OH$^-$ functions by binding to the electrophilic boron, and that this increases the rate of subsequent transmetallation. See: Braga, A. A. C.; Morgon, N. H.; Ujaque, G.; Maseras, F. *J. Am. Chem. Soc.* 2005, 127, 9298.

The data in Table 1 show that K$^+$3$^-$ and Li$^+$3$^-$ are effective catalysts without the necessity of adding an external base. From this we conclude that the 3$^-$ complex itself can function as the base by binding to the boron via the quinonoid oxygens. In the present case, the binding of 3$^-$ to the boronic acid assists the transmetallation step by decreasing the electrophilicity of the boron and by placing the transition metal in the vicinity of the transferring group (Ar'). $^1$H NMR spectra of PhB(OH)$_2$ in D$_2$O with and without K$^+$3$^-$ present indicate that an interaction occurs.

The ability of the quinone ring system to undergo facile hapticity changes ($\zeta^4 \rightarrow \eta^5$, etc.) may play a role in the ability of 3$^-$ to function as an organometalloligand in this manner. It is concluded that catalyst 3$^-$ is able to act in a bifunctional (and cooperative) manner, as has recently been suggested for other types of catalytic reactions. See: Casey, C. P.; Johnson, J. B.; Singer, S. W.; Cui, Q. *J. Am. Chem. Soc.* 2005, 127, 3100. (b) Noyori, R.; Hashiguchi, S. *Acc. Chem. Res.* 1997, 30, 97. (c) Josephsohn, N. S.; Kuntz, K. W.; Snapper, M. L.; Hoveyda, A. H. *J. Am. Chem. Soc.* 2001, 123, 11594. (d) Mermerian, A. H.; Fu, G. C. *J. Am. Chem. Soc.* 2003, 125, 4050.

In summarizing the above, Applicants have characterized a π-bonded rhodium quinonoid complex that functions as a good catalyst for the coupling of arylboronic acids and aldehydes. The catalysis is heterobimetallic in that both the transition metal and concomitant alkali metal counterion play an integral part in the reaction. In addition, the anionic quinonoid catalyst itself plays a bifunctional role by acting as a ligand to the boronic acid and as a Lewis acid receptor site for the aryl group in the requisite transmetallation. In the reaction with aldehydes, the anionic rhodium catalyst appears to operate in an intriguing multifunctional manner with one quinone oxygen acting as a ligand by binding to the boron center, thus facilitating transmetallation, while the other quinone oxygen binds to the alkali metal counterion of the catalyst and indirectly activates the aldehyde electrophile (rate: M$^+$=Li$^+$ > K$^+$>>Bu$_4$N$^+$). These interactions from the quinone oxygen atoms imply a supramolecular assembly of the boronic acid donor, the catalyst and the organic acceptor, as illustrated in Scheme 1. Such a preorganization is unprecedented and offers opportunities to significantly improve product yields and stereoselectivities in comparison to standard catalytic systems.

Scheme 1. Rhodium quinonoid catalyst is multifunctional by pre-assembling the reactants prior to formation of product.

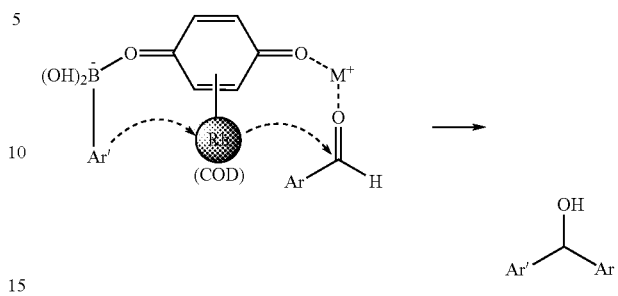

Thus, it can be seen that Applicants have successfully synthesized an anionic rhodium quinone complex that can function as a catalyst for Miyaura-Hiyashi coupling of arylboronic acids and aldehydes. Advantageously, the catalytic reactivity can be adjusted/tuned by protonation/deprotonation of the quinone complex. The catalyst as a potassium salt also functions in a heterobimetallic manner in that both the rhodium and the alkali metal play an integral role in the reaction. Moreover, the anionic rhodium complex is itself bifunctional in that it acts as a ligand in activating the boronic acid towards transmetallation of the rhodium center. The determination of a heterobimetallic catalyst that is also bifunctional (cooperative) and pH-tunable for an important class of reactions is believed to be unique.

Synthetic Procedure and Characterization of the New Materials

General: All reactions were carried out under N$_2$ in flame-dried glassware. HPLC grade THF and Diethyl Ether solvents were used as received. [Rh(COD)Cl]$_2$ was provided by Strem Chemicals. The $^1$H NMR spectra were recorded by Bruker (300 MHz) spectrometers. Elementary analyses were performed by Quantitative Technologies Inc.

Synthesis of 1$^+$BF$_4^-$: After flame drying the glassware, [Rh(COD)Cl]$_2$ (0.20 g, 0.41 mmol) and AgBF$_4$ (0.19 g, 0.97 mmol) were mixed for 1 h at room temperature in a mixed solution of methylene chloride (4 mL) and acetone (1 mL). While stirring, a white precipitate formed on the bottom of the glassware. 1,4-hydroquinone (0.18 g, 1.63 mmol) was dissolved in acetone (2 mL) and added to the reaction mixture. After stirring for 2 h at r.t., the solvent was removed via rotary evaporation. The residue was taken up in methylene chloride (3 mL) and slowly added dropwise to ether through a glass filter. The yellow precipitate was filtered and washed three times with 10 mL aliquots of diethyl ether. The isolated yield was 72% (0.24 g, 0.59 mmol). To get the single crystals: 1$^+$BF$_4^-$ (25 mg) was dissolved in a mixture of acetone (0.1 mL) and methylene chloride (1.5 mL) in a 5 mL-vial. Diethyl ether (3 mL) was carefully added to the upper layer. The solution was placed in a refrigerator for 3 days. Yellow crystals formed on the wall of vial.

$^1$H NMR (CD$_2$Cl$_2$): δ 7.64 (brs, OH, 2H), 6.53 (s, hydroquinone ring, 4H), 4.41 (br, COD, 4H), 2.40 (m, COD, 4H), 2.12 (m, COD, 4H) ppm. Elemental Anal. Calcd for C$_{14}$O$_2$H$_{18}$Rh$_1$B$_1$F$_4$: C, 41.21; H, 4.45. Found: C, 41.44; H, 4.31.

Synthesis of 2: 1+BF$_4^-$ (0.1 g, 0.24 mmol) was dissolved in THF (5 mL) in a 20 mL-one neck Schlenk flask and the solution was mixed with 1 eq. K$^t$BuO (0.027 g, 0.25 mmol) and stirred at r.t. for 2 h. While, stirring the solution became turbid and a yellow precipitate formed. The precipitate was filtered under N$_2$ and the collected solid was washed three times with THF and dried in vacuum. The isolated yield was 83% (0.065 g, 0.20 mmol).

$^1$H NMR (DMSO-d$^6$): δ 5.94 (d, J=6.3 Hz, arene ring, 2H), 5.51 (br, OH, 1H) 5.20 (d, J=6.3 Hz, arene ring, 2H), 3.83 (br, COD, 4H), 2.20 (m, COD, 4H), 1.97 m, COD, 4H) ppm. Elemental Anal. Calcd for C$_{14}$O$_2$H$_{17}$Rh$_1$: C, 52.52; H, 5.35. Found: C, 50.82; H, 5.33.

Synthesis of K$^+$3$^-$: 1 (0.1 g, 0.24 mmol) was dissolved in THF (5 mL) in 20 mL-one neck Schlenk flask and the solution was mixed with 3 eq. K$^t$BuO (0.082 g, 0.74 mmol) and stirred at r.t. for 2 h. While stirring, the solution became turbid and a yellow precipitate formed. The precipitate was filtered under N$_2$ and the collected solid was washed five times with THF and dried in vacuum. The isolated yield was 50% (0.074 g, 0.12 mmol).

$^1$H NMR (DMSO-d$^6$): δ 4.89 (s, benzoquinone ring, 4H), 3.47 (br, COD, 4H), 2.18 (m, COD, 4H), 1.96 (m, COD, 4H) ppm. $^1$H NMR (D$_2$O): δ 5.67(s, benzoquinone ring, 4H), 4.01 (br, COD, 4H), 2.35 (m, COD, 4H), 2.13 (m, COD, 4H) ppm. Elemental Anal. Calcd for C$_{14}$O$_2$H$_{16}$Rh$_1$K$_3$B2F$_8$: C, 27.56; H, 2.64. Found: C, 27.20; H, 2.59.

Synthesis of K(18-crown-6)$^+$3$^-$: 18-crown-6 (0.19 g, 0.74 mmol) was dissolved in THF (5 mL) in 20 mL-one neck Schlenk flask and K$^t$BuO solution (0.082 g, 0.74 mmol) in 5 mL was added to this solution. The solution was stirred for 30 minutes. To this solution, a THF (5 mL) solution of 1$^+$BF$_4^-$ (0.1 g, 0.24 mmol) was added. The solution was stirred for 5 hours at room temperature. Compared to the synthetic procedure of K$^+$3$^-$, no precipitate formed. The solvent was evaporated and the resulting yellow solid was washed five times with diethyl ether (15 mL, five times). After drying in vacuum, the solid was dissolved in THF and diethyl ether was added carefully on the layer of THF. After a few days yellow crystals were collected and the isolated yield was 79% (0.20 g, 0.19 mmol).

$^1$H NMR (DMSO-d$^6$): δ 4.88(s, benzoquinone ring, 4H), 3.54 (s, crown ether, 48H), 3.47 (br, COD, 4H), 2.19 (m, COD, 4H), 1.96 (m, COD, 4H) ppm. $^1$H NMR (CD$_2$Cl$_2$): δ 5.24 (s, benzoquinone ring, 4H), 3.69 (br, COD, 4H), 3.60 (s, crown ether, 48H), 2.26 (m, COD, 4H), 2.03 (m, COD, 4H) ppm. $^1$H NMR (D$_2$O): δ 5.68(s, benzoquinone ring, 4H), 4.02 (br, COD, 4H), 3.72 (s, crown ether, 48H), 2.35 (m, COD, 4H), 2.14 (m, COD, 4H) ppm. Elemental Anal. Calcd. for C$_{38}$O$_{15}$H$_{66}$Rh$_1$K$_2$B$_1$F$_4$: C, 44.28; H, 6.45. Found: C, 44.48; H, 6.61.

Synthesis of Li$^+$3$^-$: 1$^+$BF$_4^-$: (0.1 g, 0.24 mmol) was dissolved in THF (5 mL) in a 20 mL-one neck Schlenk flask and the solution was mixed with 3 eq. Li$^t$BuO (0.060 g, 0.75 mmol) and stirred at r.t. for 5 h. The solvent was evaporated and the resulting yellow solid was washed five times with mixture of THF and diethyl ether (v/v=1:5, 15 mL, five times). The precipitate was filtered under N$_2$ and the collected solid was washed five times with THF and dried in vacuum. The isolated yield was 56% (0.057 g, 0.14 mmol)

$^1$H NMR (DMSO-d$^6$): δ 4.96(s, benzoquinone ring, 4H), 3.51 (br, COD, 4H), 2.20 (m, COD, 4H), 1.98 (m, COD, 4H) ppm. Elemental Anal. Calcd. for C$_{14}$O$_2$H$_{16}$Rh$_1$Li$_2$B$_1$F$_4$: C, 40.05; H, 3.84. Found; C, 40.04; H, 4.17.

Synthesis of n-Bu$_4$N$^+$3$^-$: 1$^+$BF$_4^-$ (0.1 g, 0.24 mmol) and Bu$_4^{N+BF}{_4^-}$(0.21 g, 0.75 mmol) were dissolved in THF (5 mL) in a 20 mL-one neck Schlenk flask and the solution was mixed with 3 eq. K$^t$BuO (0.082 g, 0.74 mmol) and stirred at r.t. for 4 h. After reaction, in comparison to the synthetic procedure for K$^+$3$^-$, there was no precipitate. The solvent was evaporated and the resulting yellow solid was washed five times with diethyl ether (15 mL, five times). After drying in vacuum, the solid was dissolved in THF and the diethyl ether was added carefully on the layer of THF. After a few days yellow crystals were collected and the isolated yield was 61% (0.23 g, 0.15 mmol).

$^1$H NMR (DMSO-d$^6$): δ 4.90(s, benzoquinone ring, 4H), 3.48 (br, COD, 4H), 3.17 (t, J=7.8 Hz, Bu, 32H), 2.19 (m, COD, 4H), 1.97 (m, COD, 4H), 1.57 (brm, Bu, 32H), 1.32 (m, Bu, 32H), 0.94 (t, J=7.2 Hz, Bu, 48H) ppm. Elemental Anal. Calcd. for C$_{78}$H$_{160}$O$_2$N$_4$Rh$_1$B$_3$F$_{12}$: C, 60.46; H, 10.41; N, 3.62. Found; C, 59.23; H, 10.52; N, 3.52.

General Procedure of Catalytic Reaction

Distilled water (2 mL) was added to an elongated 15 mL-Schlenk flask. The water was bubbled for 5 minutes with nitrogen gas. After bubbling, the catalyst K$^+$3$^-$ (15 mg, 0.024 mmol), phenylboronic acid (0.15 g, 1.23 mmol) and benzaldehyde (0.1 ml, 0.98 mmol) were added. The mixture solution was heated at 75° C. for 3 hours. After reaction, the solution was cooled to room temperature and CDCl$_3$ (3.5 mL) was added. The solution was shaken for 1 minute and the CDCl$_3$ part was directly analyzed by $^1$H NMR. The yield was calculated by the comparison of peak area of aldehyde reactant and the benzyl proton of the product alcohol.

Crystallography. X-ray data collection was carried out using a Bruker single-crystal diffractometer equipped with an APEX CCD area detector and controlled by SMART version 5.0. Collection was done either at room temperature or 100 K. Data reduction was performed by SAINT version 6.0 and absorption corrections were applied by SADABS version 2.0. The structures were typically determined by direct methods and refined on F squared by use of programs in SHELXTL version 5.0. Most hydrogen atoms appeared in a difference map, or they were generally inserted in ideal positions, riding on the atoms to which they are attached.

The X-ray structure of [(H$_2$Q)Rh(COD)]BF$_4$.Et$_2$O established the anticipated η$^6$-bonding mode. The solved structure contained two independent complexes of rhodium with hydroquinone (HQ) and (COD) ligands, a BF$_4$ counterion and a diethyl ether molecule filling the void. Each HQ-Rh—COD complex is positioned on a two-fold axis, Rh(1) along an axis parallel to b, Rh(2) along one parallel to a (the asymmetric unit is charge-balanced, +1 for the two half complexes, and −1 for the BF$_4$). Notable features remained, particularly a "ghost" atom, and the R value remained high—around 13%. Rechecking by different methods showed that orthorhombic symmetry (mmm) produced R(int) and R(symm) convincingly below 5%. Cell_now ranked the original cell first (C-centered). The space group was uniquely determined to be C222(1) by the systematic absences. Solving by use of the Patterson method yielded the same solution for the heavy atoms as found earlier. However, some original difficulties were highlighted: three independent heavy atoms found, with estimated atomic numbers 48, 39, and 24—although the only heavy atom is believed to be rhodium. The third heavy atom had been tentatively treated as carbon, but it may be something bigger, and its position mirrored the second rhodium atom on the other side of the HQ ligand. This suggested that the atom might be a fractional part of a disordered rhodium atom. When its identification as Rh(3) was tested, the R values dropped and the bonds to the expected ligands became apparent. Rh(3) occupied a position between the HQ coordinated to Rh(2) and the COD coordinated to the Rh(2) in the adjacent cell. Since neither ligand can bond to two rhodium atoms, disorder of the whole Rh(2) complex is believed to be present. The HQ ligand on Rh(2) is approximately overlapped by another on Rh(3), and the COD on the adjacent Rh(2) is approximately overlapped by another on Rh(3). This "whole molecule disorder" is difficult to model accurately, so an approximate model was constructed by restraining the ligands on Rh(2) and Rh(3) to be similar to the better-defined ligands on Rh(1), by treating all atoms except rhodium in the Rh(3) complex as isotropic, and by ignoring the likely disorder in the diethyl ether. With this model, the occupancy of the Rh(2) complex was about 68%, the Rh(3) complex about 32%; hence the electron counts on the three rhodium atoms are roughly consistent with the Patterson results. That is not the end of the disorder besetting this crystal; it is also a racemic twin, with enantiomers in a 55:45 ratio. Some complications in the analysis may preclude placing much weight on bond lengths and angles, but the connectivity is certainly determined (R1=0.089%).

X-ray quality crystals of $K^+3^-$ could not be grown, but the butylammonium salt was readily obtained by metathesis and its X-ray structure determined as $Bu_4N^+[(1,4-Q)Rh(COD)]^-.3 Bu_4NBF_4$ (R1=0.076%). The Rh—C bond lengths clearly indicated an $\eta^4$-bonding mode, with the quinone Rh—C distances being ca. 0.2 Å greater for the C(O) carbons in comparison to the other four quinone carbons. Deprotonation of $1^+BF_4^-$ with KO$^t$Bu in the presence of 18-crown-6 produced the salt $K(18-C-6)^+[(1,4-Q)Rh(COD)]^-.K(18-C-6)BF_4$, in which each quinone oxygen is linked to a crown ether encapsulated potassium ion. X-ray data for this salt were only moderate in quality (R1=12.8%), but sufficient to establish connectivity.

II. Highly Efficient 1,4-Additions of Electron Deficient Aryl Boronic Acids with a Novel Rhodium(I) Quinonoid Catalyst As noted above, rhodium(I) quinonoid catalysts are a remarkably efficient new class of reagents for the conjugate addition of aryl boronic acids. In this section, the use of these reagents in catalyzing the highly efficient 1,4-additions of a broad range of boronic acids, including heteroaromatic and an example of trihalogenated aryl boronic acids is described. The rhodium(I) catalyzed conjugate addition of aryl boronic acids to electron deficient olefins is a mild approach to carbon-carbon bond formation. See Sakai, M.; Hayashi, H.; Miyaura, N. *Organometallics*, 1997, 16, 4229-4231; Fagnou, K.; Lautens, M. *Chem. Rev.* 2003, 103, 169-196; Hayashi, T.; Yamasaki, K. *Chem. Rev.* 2003, 103, 2829-2844.d) Hayashi, T. *Pure Appl. Chem.* 2004, 76, 465-475. This approach has been shown to be more chemoselective and widely applicable for molecules with reactive functionality than traditional cuprate or grignard chemistry. See Chapman, C. J.; Frost, C. G. *Adv. Synth. Catal.* 2002, 345, 353-355; Moss, R. J.; Wadsworth, K. J.; Chapman, C. J.; Frost, C. G. *Chem. Commun.* 2004, 1984-1985; Paquin, J.; Defieber, C.; Stephenson, C. R. J.; Carreira, E. M. *J. Am. Chem. Soc.* 2005, 127, 10850-10851. In addition, the enantioselective rhodium catalyzed conjugate addition reaction with chiral ligands, as shown by Hayashi and others, demonstrates the application of this methodology toward asymmetric synthesis. See Chapman, C. J.; Frost, C. G. *Adv. Synth. Catal.* 2002, 345, 353-355; Moss, R. J.; Wadsworth, K. J.; Chapman, C. J.; Frost, C. G. *Chem. Commun.* 2004, 1984-1985; Paquin, J.; Defieber, C.; Stephenson, C. R. J.; Carreira, E. M. *J. Am. Chem. Soc.* 2005, 127, 10850-10851. While this methodology is mild and highly effective for most substrates, aryl boronic acids with electron withdrawing substituents undergo competitive proto-deborylation. Attempts to favor 1,4-addition have included increasing aryl boronic acid equivalents, increasing catalyst loading, altering the aqueous/organic solvent ratio, decreasing temperature and in situ generation of aryl boronate reactants. The highest reported yields are afforded with 2-10 equivalents of aryl boronic acid, $\geq 3$ mol % catalyst loading and prolonged reaction at 90-100° C. In this section, it is reported that the use of a new rhodium quinone catalyst provides a mild, highly effective and operationally facile procedure for conjugate addition of aryl boronic acids to 1-cyclohexen-2-one.

As noted in the previous sections, the development of the anionic rhodium $\eta^4$-quinonoid complex $K^+3^-$ (or "3.K") is described and it was found that it efficiently catalyzes the 1,2-addition of aryl boronates to aldehydes according to Eq. 1 below. See, Son, S. U.; Kim, S. B.; Reingold, J. A.; Carpenter, G. B.; Sweigart, D. A. *J. Am. Chem. Soc.* 2005, 127, 12238-12239. The oxygen sensitive 3.K was synthesized and isolated by double deprotonation of the hydroquinone precursor complex 1 in THF, via the neutral semiquinone 2.

In this section it is reported that preformed catalyst 3.K is also effective in conjugate 1,4-addition reactions, as described below. The air-sensitivity of anionic catalyst 3.K may be a drawback in this procedure, potentially necessitating greater catalyst loadings than may otherwise be required. In addressing this problem, it was found that the operational ease of the catalyzed conjugate additions of aryl boronic acids can be greatly facilitated by the in situ generation of catalyst 3.M (M=Li, Na, K, Cs) from the air stable rhodium hydroquinone salt 1. The conjugate addition reactions in DME/$H_2O$ with catalyst 3.Li, which is generated in situ from 1 and LiOH, are highly efficient and afford excellent yields with negligible side products in short reaction times at 50° C. (Table 2).

Scheme 2. Double deprotonation of rhodium hydroquinone 1 to afford the active quinonoid complex 3.K.

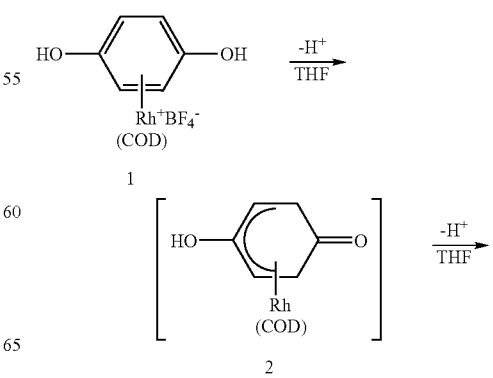

A significant aspect of the new procedure is the low catalyst loading (0.5 mol % reduced

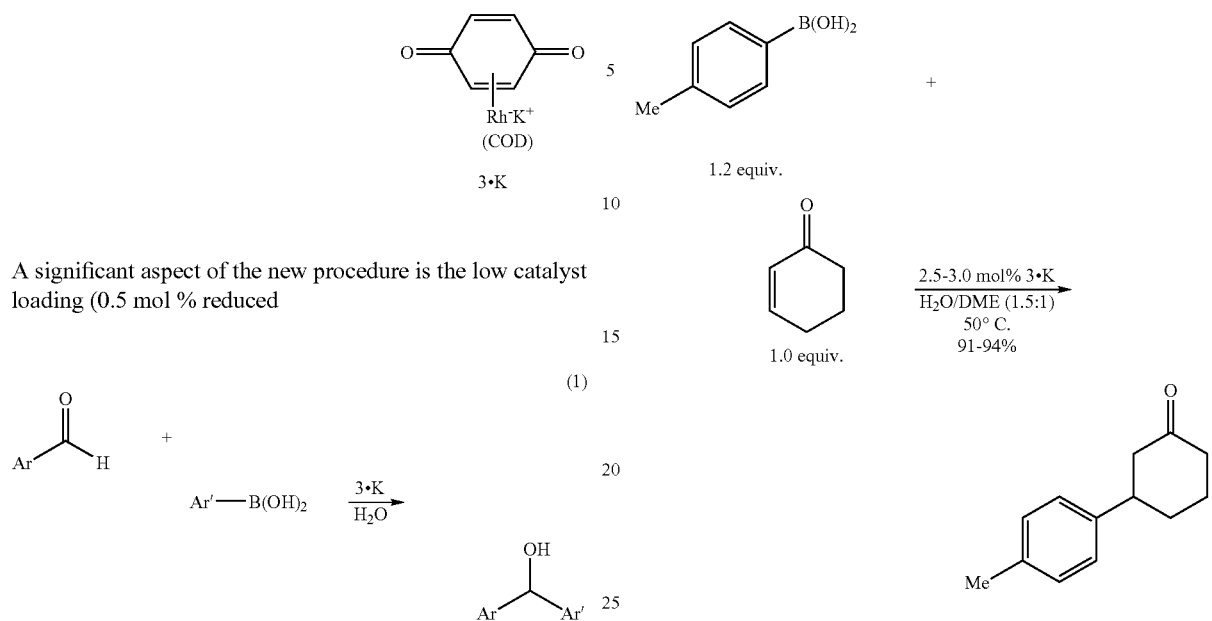

from 2.5 mol % in Scheme 3) and low boronic acid equivalency (1.2 equiv) relative to the conjugate acceptor as compared to the conditions reported in the literature. An evaluation of counter ions indicates that 3.Li is more efficacious than the corresponding potassium salt 3.K (Table 2, entries 4-6). This counter ion effect was also evident in catalyzed 1,2-additions and may be ascribed to general acid activation of the organic electrophile (vide infra).

Scheme 3. An example of conjugate addition with an aryl boronic acid using preformed quinonoid catalyst 3.K.

Preliminary results showed that the reaction exhibited a marked dependence on base equivalency, which was studied through systematic variation (Table 2). The role of base in the conjugate addition of aryl boronic acids to electron deficient olefins is not well understood. For the conjugate addition of p-tolyl boronic acid to 2-cyclohexen-1-one, stoichiometric LiOH (1.2 eq) affords excellent yield of desired ketone 6b (99%, entry 7, Table 2), although the reaction is equally productive with 2.0 mol % of base (96%, entry 6). The most dramatic change in yield was seen upon increasing base from 0.75 mol % (63%) to 1.0 mol % (90%) (entries 45). This behavior is consistent with complete activation of hydroquinone 1 into the active quinonoid catalyst 3.Li where 1 mol % of LiOH is required for complete double deprotonation of the precatalyst. In contrast, the m-nitrophenyl boronic acid analogue affords the highest yield of desired ketone 6e (87%) with 2.0 mol % of LiOH. Increasing the base quantity to 120 mol % results in reduced yield (19%, entry 7) and a prevalent side product, nitrobenzene, resulting from protodeborylation. This study demonstrates that base is required for the reaction and 2.0 mol % provides optimal yield of the desired conjugate addition product. During further studies to optimize the reaction conditions, a series of additives and bases were examined. Catalytic amounts of carbonate bases, $Na_2CO_3$ (2.0 mol %) or $Cs_2CO_3$ (2.0 mol %), are effective at producing high yielding conjugate additions with boronic acid 4a (Table 3, entries 6 & 8), while stoichiometric amounts (120 mol %) of carbonate bases (entries 7 & 9) attenuated reactivity. Pyridine, either catalytic or quantitative, arrests all reactivity and consistent with this observation is the lack of product with pyridine boronic acids. Additional hydroquinone shows no detectable effect upon reaction outcome while lithium salts, such as LiCl or $LiBF_4$, either diminish the amount of product or completely arrest the reaction. The addition reaction can be run in the absence of organic solvent, however, stoichiometric base (120 mol %) is required for efficient reaction (entry 10 versus 11). This result is presumably due to the solubilization of the boronic acid into the aqueous phase by formation of the corresponding—ate complex. Preferred reaction conditions, outlined as a general procedure in the experimental section, are highly effective and facile for a range of boronic acid substrates. Using 2-cyclohexen-1-one as our conjugate acceptor, a number of different aryl boronic acids were studied with our optimized reaction conditions (Table 4). Ketone products 6a-g (entries 1-7) are afforded in high yields, with low catalyst loading (0.5 mol %) and low boronic acid equivalency (1.2 eq). Electron deficient boronic acids (entries 5-9) are afforded in excellent yields (94-99%) without any procedural modification from the earlier analogues. Improved yields (92-93%) of meta-nitro analogue 6l were achieved either by increasing the catalyst loading (2.0 mol %, entry 12) or increasing equivalencies of boronic acid (1.5 equiv, entry 13). Tri-fluoro analogues 6j and 6k (entry 14,15) were afforded in good to moderate yields (70% and 30% respectively). This is believed to be the first report of conjugate addition of a tri-halogenated aryl boronic acid. Efforts are underway to further optimize the additions of tri-fluorophenyl boronic acids 4j and 4k. Both 2,4-bis(trifluoromethyl)phenyl boronic acid and ortho-nitro phenyl boronic acid failed to produce the desired addition products under our standard conditions. The 4-, 5- or 6-indoloboronic acids (Table 5) undergo conjugate addition while N-Boc-2-indoloboronic acid (entry 1) does not afford any product. The additions of 4-indoloboronic acid (entry 2, Table 4) and o-tolyl boronic acid (entry 3, Table 4) show that ortho substitution can be tolerated, despite the attenuated reactivity observed for o-substituted boronic acids and documented difficulties of reactions with N-Boc protected pyrrole-2-boronic acids. See Lautens, M.; Mancuso, J.; Grover, H. *Synthesis* 2004, 12, 2006-2014.

TABLE 3

The role of additives and alternate bases upon conjugate addition reaction.

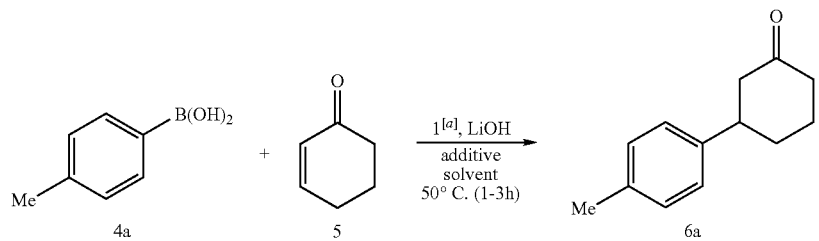

| entry | LiOH (mol %) | additive (mol %) | solvent | 6a yield[b] (%) |
|---|---|---|---|---|
| 1 | 0.5 | hydroquinone (2.0) | DME/$H_2O$ | 31[c] |
| 2 | 0.5 | $LiBF_4$ (120) | DME/$H_2O$ | — |
| 3 | 0.5 | LiCl (120) | DME/$H_2O$ | 20 |
| 4 | — | pyridine (2.0) | DME/$H_2O$ | — |
| 5 | — | pyridine (120) | DME/$H_2O$ | — |
| 6 | — | $Cs_2CO_3$ (2.0) | DME/$H_2O$ | 97 |
| 7 | — | $Cs_2CO_3$ (120) | DME/$H_2O$ | 68 |
| 8 | — | $Na_2CO_3$ (2.0) | DME/$H_2O$ | 93 |
| 9 | — | $Na_2CO_3$ (120) | DME/$H_2O$ | 74 |
| 10 | 2.0 | — | $H_2O$ | — |
| 11 | 120 | — | $H_2O$ | 99 |

[a]0.5 mol %
[b]Isolated yield after silica gel chromatography.
[c]Compare to Table 1 entry 3.

TABLE 4

Conjugate addition of a variety of boronic acids to 2-cyclohexen-1-one.

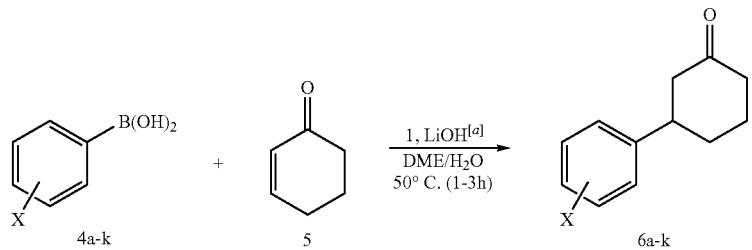

| entry | boronic acid[b] (4) | 1 (mol %) | product | yield[c] (%) |
|---|---|---|---|---|
| 1 | a. X = H | 0.5 | 6a | 98 |
| 2 | b. X = p-Me | 0.5 | 6b | 97 |
| 3 | c. X = o-Me | 0.5 | 6c | 99 |
| 4 | d. X = 4-NH-Boc | 0.5 | 6d | 99 |
| 5 | e. X = p-OMe | 0.5 | 6e | 97 |
| 6 | f. X = p-Cl | 0.5 | 6f | 99 |
| 7 | g. X = p-F | 0.5 | 6g | 94 |
| 8 | g. X = p-F[d] | 0.5 | 6g | 99 |
| 9 | h. X = 3-Cl,4-F | 0.5 | 6h | 96 |
| 10 | i. X = m-NO$_2$ | 0.5 | 6i | 85 |
| 12 | i. X = m-NO$_2$ | 2.0 | 6i | 93 |
| 13 | i. X = m-NO$_2$[e] | 0.5 | 6i | 92 |
| 14 | j. X = 3,4,5-tri-F[d] | 2.0 | 6j | 70 |
| 15 | k. X = 2,3,4-tri-F | 2.0 | 6k | 30 |

[a]2.0 mol %
[b]1.2 equiv. relative to 1-cyclohexen-2-one
[c]Isolated yield after silica gel chromatography.
[d]fromboroxime
[e]1.5 eq of boronic acid

TABLE 5

Indole boronic acid conjugate addition to 1-cyclohexene-2-one.

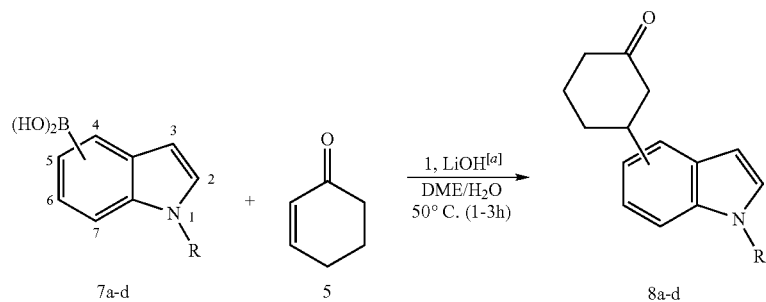

| entry | boronic acid(7) | 1 (mol %) | product | yield[b] (%) |
|---|---|---|---|---|
| 1 | a, 2-B(OH)$_2$ R = Boc | 0.5 | 8a | — |
| 2 | b, 4-B(OH)$_2$ R = H | 0.5 | 8b | 80 |
| 3 | c, 5-B(OH)$_2$ R = H | 0.5 | 8c | 63 |
| 4 | d, 6-B(OH)$_2$ R = H | 0.5 | 8d | 86 |

[a]2.0 mol %
[b]Isolated yield after silica gel chromatography.

The catalytic system presented is similarly efficient with a range of substrates (Table 6). The conjugate addition of p-tolyl boronic acid (4b) was studied with a selection of conjugate acceptors. The addition to cinnamaldehyde (9a) and ethyl cinnamate (9b) were highly efficient providing the products in 96% and 95% isolated yields, respectively (Table 6, entries 1 & 2). The β,β-disubstituted olefins are a problem for many catalytic systems providing no observed conjugate additions, but our preliminary studies have found that 4b can be added to ethyl 3,3-dimethyl-acrylate (9c) in modest yield (Table 6, entry 3). Reactions with α,β-unsaturated secondary amide 9d failed to provide any of the desired conjugate addition (Table 6, entry 4), however, cyclic imide 9e produced the corresponding product 10e in 97% isolated yield (Table 6, entry 5). Further studies are underway to determine the scope of substrates and to improve addition to highly hindered systems.

TABLE 6

Conjugate addition to a variety of conjugate acceptors.

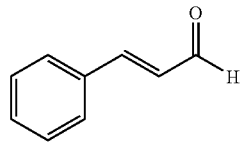

| entry | substrate | product | yield[c](%) |
|---|---|---|---|
| 1 | 9a | 10a | 96[d] |
| 2 | 9b | 10b | 95[d] |
| 3 | 9c | 10c | 14[e] |
| 4 | 9d | 10d | 97 |

[a]0.5 mol%
[b]2.0 mol%
[c]Isolated yield after silica gel chromatography based on 9.
[d]1 mol% 1 and 4.0 mol% LiOH.
[e]1.5 equiv of 4b and 150 mol% LiOH.

We hypothesize that the reactivity observed for quinone complex 3-Li is due to bifunctional activation in catalyzing the reaction of boronic acids and electron deficient olefins. In the activation of the boronic acid, the alkoxide of the hydroquinone ligand can act as a nucleophile to activate the boronic acid directly for transmetallation to the rhodium center (Scheme 4). After formation of the rhodium aryl species, the lithium counter-ion can act as a general acid to pre-organize and activate the conjugate acceptor for carbo-metallation. This pre-organization acts to accelerate the rate of conjugate addition in relation to the rate of proto-deborylation, thereby allowing the use of extremely electron deficient aryl boronic acids. Mechanistic studies are underway to elucidate the details of this new class of $Rh^1$ catalysts.

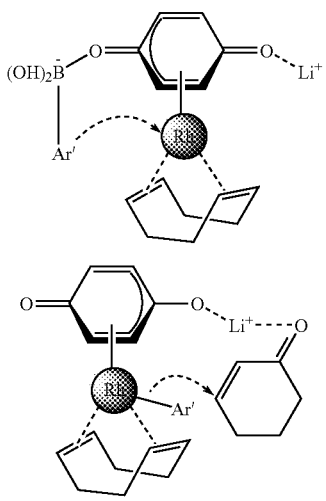

Scheme 4. [a]General base activation of the boronic acid to the -ate complex. [b] General acid activation of the electron deficient olefin.

Thus, Applicants have developed and disclose an efficient procedure for the conjugate addition of electron deficient aryl boronic acids to 2-cyclohexen-1-one and other activated conjugate acceptors (Table 6). Accordingly, examples of conjugate acceptors also include those of Table 6 above.

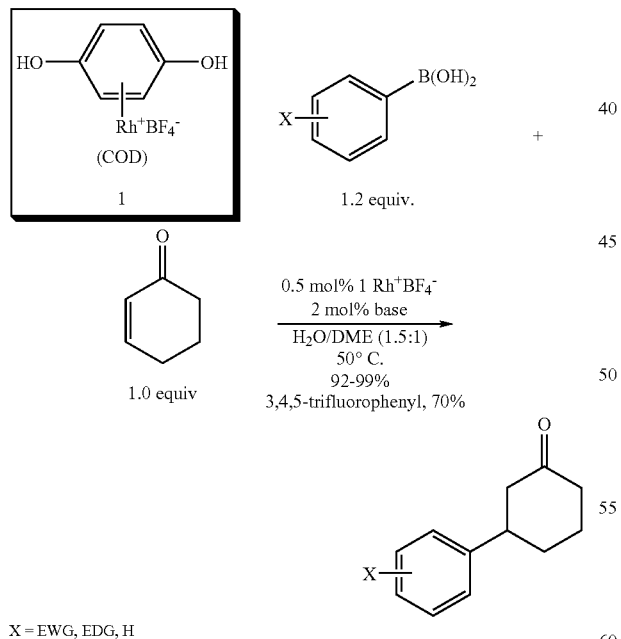

X = EWG, EDG, H

Scheme 5 provides a summary of conditions and reaction scope. This catalyst system is noteworthy due to the operational ease of use and high isolated yields with low levels of catalyst and boronic acid loading in an aqueous solution. The yields of addition products, using extremely electron deficient aryl boronic acids including the first report of trihalogenated aryl boronic acids, are excellent with minimal protodeborylation and a complete absence of Heck type products. See Zou, G.; Wang, Z.; Zhu, J.; Tang, J. *Chem. Commun.* 2003, 2438-2439; Mori, A.; Danda, Y.; Fujii, T.; Hirabayashi, K.; Osakada, K. *J. Am. Chem. Soc.* 2001, 123, 10774-10775.

In summary, disclosed is a new and highly efficient catalytic system using a rhodium quinonoid complex to catalyze the conjugate addition of aryl boronic acids. The process is characterized by high isolated yields of product using extremely electron deficient aromatic boronic acids while maintaining low catalyst loadings in short reaction times at about 50° C. Additionally, examples of trifluoronated aryl additions are presented above which may be of interest to the biomedical and pharmaceutical communities.

Experimental Section—The rhodium(I) hydroquinone catalyst was synthesized as described above. Also see, for customary synthetic procedures, e.g. Y.-S. Huang, S. Sabo-Etienne, X.-D. He, B. Chaudret, *Organometallic* 1992, 11, 303; S. Sun, G. B. Carpenter, D. A. Sweigart, *J. Organomet. Chem.* 1996, 512, 257; J. Le Bras, H. Amouri, J. Vaissermann, *Organometallics* 1998, 17, 1116; M. Oh, G. B. Carpenter, D. A. Sweigart, *Organometallics* 2002, 21, 1290; J. Moussa, C. Guyard-Duhayon, P. Herson, H. Amouri, M. N. Ragwr, A. Jutand, *Organometallics* 2004, 23, 6231.

General Procedure: A 1-dram vial fitted with a Teflon cap was charged with aryl boronic acid (1.2 mmol) and enone (1.0 mmol) and dimethoxyethane (DME, 1.0 mL). A solution of 1 (0.02 M DME, 0.250 mL, 0.005 mmol, 0.5 mol %) followed by an aqueous LiOH solution (1.0 M, 0.020 mL, 0.020 mmol, 2.0 mol %). The headspace of the vial was flushed with $N_2$ and deoxygenated $H_2O$ (1.5 mL) was added. The vial was capped and the resulting mixture was stirred at 50° C. for 1 h. The reaction mixture was diluted with a saturated solution of $NH_4Cl$ (5 mL), extracted with 25% EtOAc/hexanes (2×5 mL), dried ($Na_2SO_4$), filtered through a silica plug, and concentrated to afford pure product as characterized by $^1H$ and $^{13}C$ NMR and high resolution mass spectrometry.

Note, it was also found that diethyl ether and THF can be used in place of DME, however no reaction is observed in toluene as solvent.

An alternate procedure was found to be efficacious for the conjugate addition to hindered poly-substituted electron deficient olefins such as tri-substituted olefin, acetyl-cyclohexene (Scheme 7). These conditions provide conjugate addition to hindered systems in the presence of minute amounts of organic solvent.

Scheme 7. Conjugate addition to tri-substituted olefins.

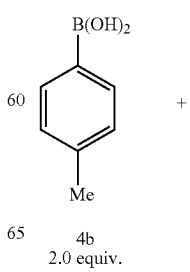

4b
2.0 equiv.

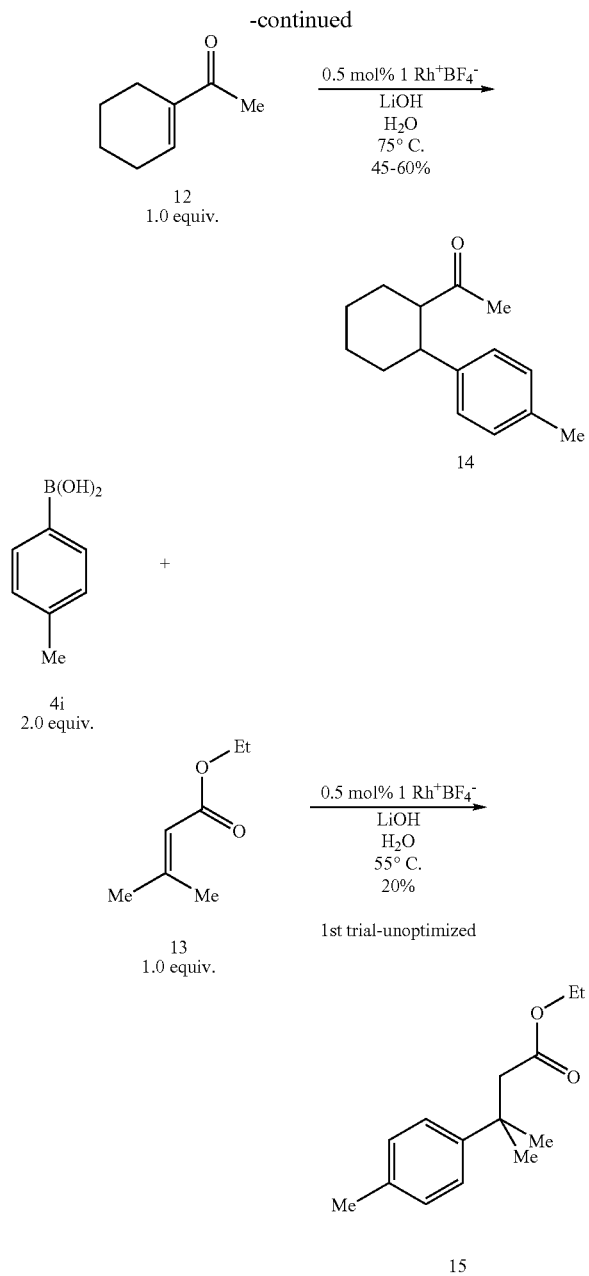

Alternate Reaction Conditions: General Procedure: In a one-dram vial, p-tolyl boronic acid (410 mg, 3.0 mmol, 3.0 equiv.) was combined with 1-acetylcyclohexene (124.1 mg, 1.0 mmol, 1.0 equiv.) before addition of a solution of Rh catalyst (500 µL, 0.02 M in DME, 1.0 mole %), LiOH (2.85 mL, 1.0 M in water, 2.85 equiv.), and deionized water (1.0 ml, deoxygenated by sparging with nitrogen gas for 30-60 minutes). The headspace of the vial was flushed with nitrogen before sealing the vessel with a teflon cap. The reaction mixture was vigorously stirred to induce phase mixing for 19 hours at 75° C. The reaction mixture was quenched with ammonium chloride (3.0 mL) and extracted with ethyl acetate/hexanes (1:3, 2×2 mL). The combined organic layers were washed sequentially with NaOH (2 ml, 1 N) and brine (2.0 ml), dried (sodium sulfate) and filtered through a short plug of silica gel, using 25% ethyl acetate/hexanes as the eluent. The desire product was obtained in 60% yield (128.7 mg) after concentration and removal of residual 1-acetylcyclohexene under reduced pressure (250 mTorr, rt, 12 h).

Rhodium quinonoid catalysts, arising from precatalyst 1, are believed to be a remarkably efficient new class of reagents for the conjugate addition of aryl boronic acids. Thus, as explained above, herein Applicants describe the use of these reagents in catalyzing the highly efficient addition of a broad range of boronic acids, including heteroaromatic and the first believed example of trihalogenated-aryl boronic acids.

III. Organometallic Crystal Engineering of [1,4- and 1,3-hydroquinone)Rh(P(OPh$_3$)$_2$]$^+$ Salts by Charge Assisted Hydrogen Bonding Organometallic crystal engineering has attracted significant recent attention due to potential catalytic and materials applications. See: D. Braga, F. Grepioni and G. R. Desiraju, Chem. Rev., 1998, 98, 1375; A. D. Burrows, C.-W. Chan, M. M. Chowdhry, J. E. McGrady and D. M. P. Mingos, Chem. Soc. Rev., 1995, 24, 329; S.-S. Sun and A. J. Lees, Inorg. Chem., 2001, 40, 3154; C. J. Kuehl, T. Yamamoto, S. R. Seidel and P. J. Stang, Org. Lett., 4, 913; D. M. Shin, Y. K. Chung and I. S. Lee, Cryst. Growth Des., 2002, 2, 493; Y. Kim and J. G. Verkade, Inorg. Chem., 2003, 42, 4262; R. D. Hartnell and D. P. Arnold, Organometallics, 2004, 23, 391; Y.-B. Dong, Y. Geng, J.-P. Ma and R.-Q. Huang, Inorg. Chem., 2005, 44, 1693. D. F. Eaton, A. G. Anderson, W. Tam and W. Wang, J. Am. Chem. Soc., 1987, 109, 1886; I. S. Lee, Y. K. Chung, J. Mun and C. S. Yoon, Organometallics, 1999, 18, 5080; I. R. Whittall, A. M. McDonagh, M. G. Humphrey and M. Sanoc, Adv. Organomet. Chem., 1999, 43, 349; S. Barlow and S. R. Marder, Chem. Commun., 2000, 1555; M. Albrecht, M. Lutz, A. L. Spek and G. van Koten, Nature, 2000, 406, 970; M. Albrecht and G. van Koten, Angew. Chem., Int. Ed., 2001, 40, 3750; P. H. Dinolfo, J. T. Hupp, Chem. Mater., 2001, 13, 3113; S. J. Lee, A. Hu and W. Lin, J. Am. Chem. Soc., 2002, 124, 12948; M. J. E. Resendiz, J. C. Noveron, H. Disteldorf, S. Fischer and P. J. Stang, Org. Lett., 2004, 6, 651.

A variety of inorganic-organometallic coordination polymers using [η$^4$-benzoquinone)Mn(CO)$_3$]$^-$ as the fundamental building block connected to metallic nodes via the quinone oxygen atoms have been reported. See: M. Oh, G. B. Carpenter and D. A. Sweigart, Acc. Chem. Res., 2004, 37, 1; S. U. Son, S. B. Kim, J. A. Reingold, G. B. Carpenter and D. A. Sweigart, J. Am. Chem. Soc., 2005, 127, 12238. Braga and coworkers have reported the syntheses of hydrogen-bond directed organometallic and organic-organometallic supramolecules based on ferrocene, cobaltocene and bis-benzene chromium units. See: D. Braga, L. Maini and F. Grepioni, Organometallics, 2001, 20, 1875; D. Braga, G. Cojazzi, D. Emiliani, L. Maini and F. Grepioni, Organometallics, 2002, 21, 1315; D. Braga, M. Polito, D. D' Addario, E. Tagliavini, D. M. Proserpio, F. Grepioni and J. W. Steed, Organometallics, 2003, 22, 4532; D. Braga, M. Polito, M. Bracaccini, D. D' Addario, E. Tagliavini and L. Sturba, Organometallics, 2003, 22, 2142; D. Braga, M. Polito, D. D' Addario and F. Grepioni, Cryst. Growth Des., 2004, 4, 1109; D. Braga, M. Polito and F. Grepioni, Cryst. Growth Des., 2004, 4, 769. In the latter studies it was suggested that charge assisted hydrogen bonding, which can occur in ionic or zwitterionic systems and refers to hydrogen bonding accompanied by coulombic interactions resulting from the inherent electronic charges, can be an effective strategy for fully utilizing the directional properties of hydrogen-bonding mediated assembly. See: D. Braga and F. Grepioni, Acc. Chem. Res., 2000, 33, 601.

The self-assembly of molecules or molecular units into supramolecular arrays can be driven by covalent bond formation and/or can be driven by noncovalent interactions such as π-π stacking, hydrogen bonding and van der Waals forces. Hydrogen bonding has been recognized as a particularly powerful tool in this regard because of its unique directionality and specificity. Supramolecular assemblies predicated on hydrogen bonding can be reinforced by the cooperative action of multi-point H-bonds, or additional cooperative interactions between the modular components of the assembly. An important example of this is so-called charge-assisted hydrogen bonding. This can lead to an exceptionally strong interaction between the oppositely charged components.

Recently, it has been recognized that the structural and chemical versatility of organometallic building blocks can be utilized to prepare supramolecular assemblies with distinct physical and chemical properties that cannot be replicated in purely organic systems. For example, self-assembled coordination networks that feature transition metal nodes and the anionic complex $[(\eta^4\text{-quinone})Mn(CO)_3]^-$ as organometalloligand spacers have been extensively reported by us. See Sweigart, et al., *Accounts of Chemical Research*, 2004, 37, 1. In addition to coordination mediated self-assembly, there has been a considerable interest in supramolecular organometallic assemblies formed via non-covalent interactions. Braga and coworkers, referenced above, for example, have described the self-assembly of a variety of organometallic sandwich compounds through charge-assisted hydrogen bonding.

In this section, Applicants present the structural consequences of hydrogen bonding within the ionic organometallic complexes of the type $[(\eta^6\text{-hydroquinone})Rh(P(OPh)_3)_2]^+$ $X^-$ ($14^+$; $X=BF_4$, $ClO_4$, $SbF_6$, OTf, OTs, OPf), $[(\eta^6\text{-resorcinol})Rh(P(OPh)_3)_2]^+BF_4^-$ ($15^+BF_4$) and $[(\eta^6\text{-4,4'-biphenol})Rh(P(OPh)_3)_2]BF_4(16^+BF_4^-)$. FIG. 5 illustrates the complexes. In these complexes, the —OH groups are activated by the electrophilic rhodium moiety to participate in charge-assisted hydrogen bonding to the anionic counterion. The crystal structures feature three kinds of non-covalent interactions: hydrogen bonding, coulombic attraction and π-π stacking, which result in an intriguing array of architectures: dimeric, 1-D chain, $C_2$-helical, and $C_3$-helical. The nature of the charge-assisted hydrogen bonding and the resulting 3-D structure in these systems is remarkably dependent on the identity of the anion. Robust porous networks are formed rapidly (minutes or less) with $[(\eta^6\text{-hydroquinone})Rh(P(OPh)_3)_2]^+X^-$ ($X=BF_4$, $ClO_4$) and $[(\eta^6\text{-resorcinol})Rh(P(OPh)_3)_2]^+BF_4^-$. The hydrophobic pores in $[(\eta^6\text{-hydroquinone})Rh(P(OPh)_3)_2]ClO_4$ bind toluene reversibly. This work demonstrates that self-assembly of well-designed organometallic building blocks via charge-assisted hydrogen bonding is an effective strategy for the construction of robust porous networks. With counterions containing both oxygen and fluorine, it was found that the former is invariably the hydrogen bond acceptor, a result in agreement with atomic charge calculations. It is anticipated that self-assembly via charge-assisted hydrogen bonding is an approach applicable to many organometallic systems.

Complexes $15^+BF_4$ and $16^+BF_4$ were synthesized in good yields by treatment of the precursor $[Rh(P(OPh)_3)_2Cl]_2$ with $AgBF_4$ in methylene chloride to generate $[Rh(P(OPh)_3)_2]^+$ in situ, which was then reacted with resorcinol and 4,4'-biphenol, respectively. The 1,4-hydroquinone salts $14^+X$ ($X^-=BF_4^-$, $SbF_6^-$, $PF_6^-$, $ClO_4^-$, $OTs^-$, $OTf^-$) were synthesized in a similar manner, with the anion $X^-$ deriving from the silver salt (AgX) utilized. The bulky phosphite ligands were introduced to minimize the probability of interpenetration in the solid state. Examples of the utilization of bulky groups to get non-interpenetrated porous structures include X. Xu, M. Nieuwenhuyzen and S. L. James, *Angew. Chem. Int. Ed.*, 2002, 41, 764; N. G. Pschirer, D. M. Ciurtin, M. D. Smith, U. H. F, Bunz and H. C. Zur Loye, *Angew. Chem. Int. Ed.*, 2002, 41, 583; B. Moulton and M. J. Zaworotko, *Curr. Opin. Sol. State Mat. Sci.*, 2002, 6, 117.

Figure 6:
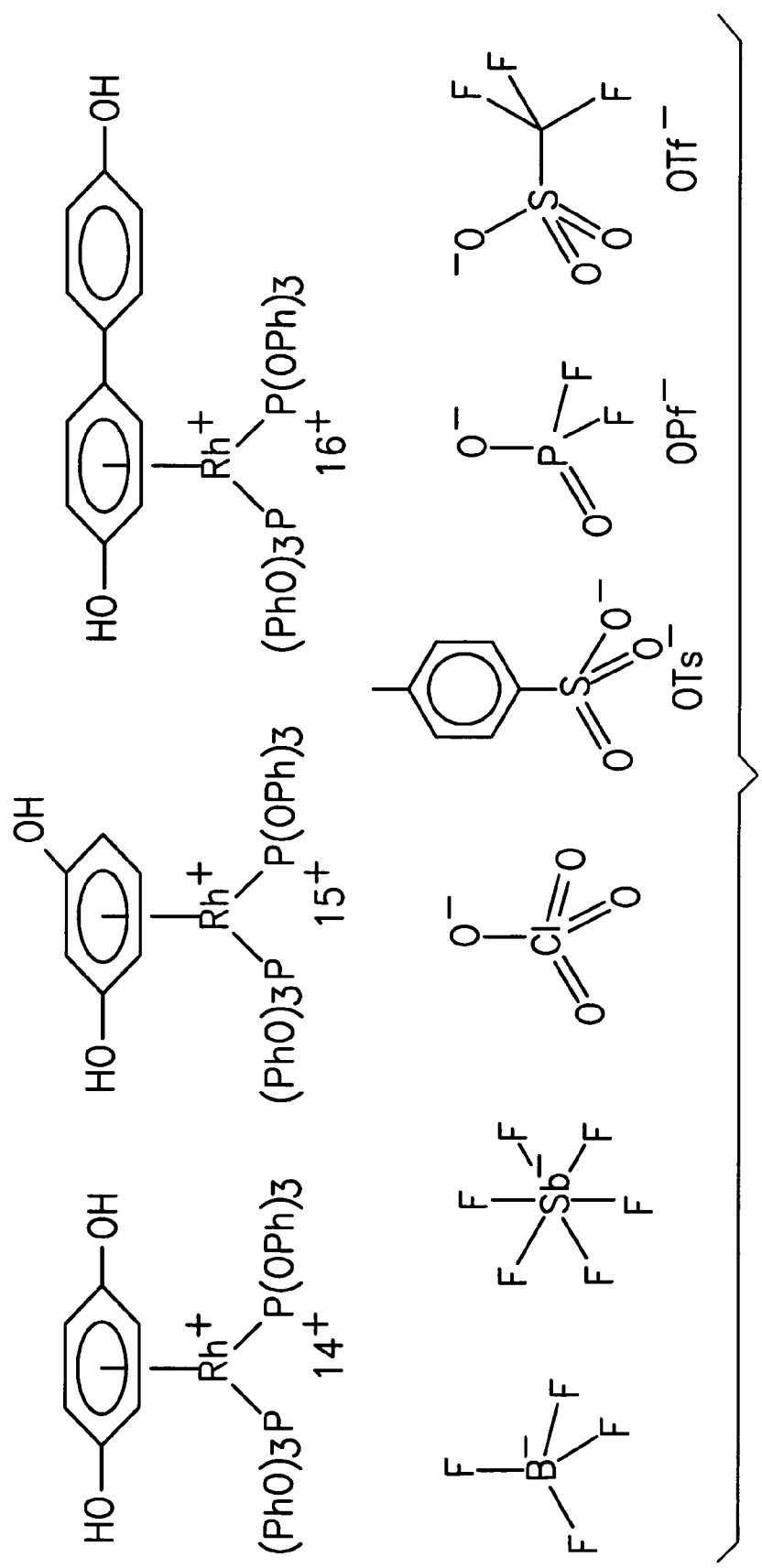
FIG. 6 shows cationic complexes and associated anions used to study the structural consequences charge assisted hydrogen bonding.

Cartoon diagrams of the different types of solid state structural patterns found are shown in FIG. 6. The cationic hydroxybenzene complexes ($14^+$-$16^+$) and the anionic companion ($X^-$) can assemble to generate dimeric, 1-D chain, $C_2$-helical or $C_3$-helical motifs, most of which feature charge-assisted hydrogen bonding. Relevant sample X-ray crystallographic data are summarized in Table 7.

Figure 13:
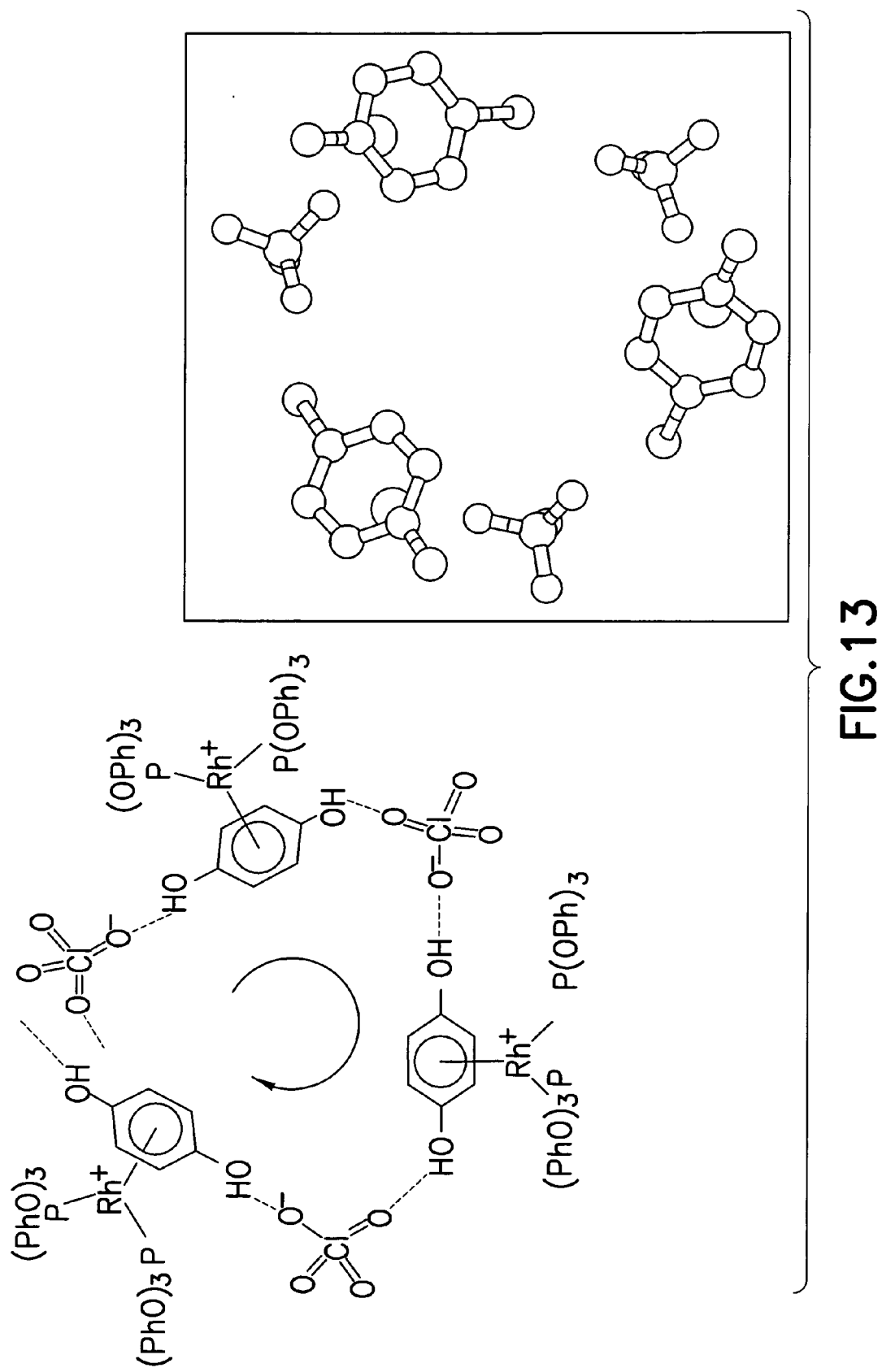
FIG. 13 shows the $C_3$ helical hydrogen bonded structure found in 14$^+$ClO$_4^-$ and 14+BF$_4^-$.

Crystals of $[(\eta^6\text{-1,4-hydroquinone})Rh(P(OPh)_3)_2]^+SbF_6^-$ ($14^+SbF_6^-$) suitable for the single crystal X-ray analysis were prepared by layering a methylene chloride solution at $-20°$ C. with diethyl ether or hexane. Cubic-shaped orange crystals and plate-shaped yellow crystals were obtained with diethyl ether and hexane co-solvents, respectively. The X-ray structure of the orange crystals revealed that the hydroquinone —OH groups are hydrogen bonded to diethyl ether present in the crystal lattice (O••••O=2.6 Å), as shown in FIG. 13 (left). The hydroquinone rings are arranged in pairs due to an edge-to-edge π-π stacking interaction involving two carbon atoms of each ring. The average C••••C contact between the edges of adjacent rings is 3.3 Å. After drying under vacuum for one day, the XRPD (X-ray powder diffraction) pattern of $14^+SbF_6^-$ changed significantly, from which it is inferred that the solid remains crystalline but undergoes a substantial structural change upon solvent loss. It proved possible to ascertain the nature of this change because the simulated XRPD obtained from single crystal data for $14^+SbF_6^-$ grown with hexane co-solvent matched that obtained after drying $14^+SbF_6^-$.2 $Et_2O$, suggesting that they have the same structure. The structure of the former, reveals a π-π stacked dimeric aggregate with nearly eclipsed hydroquinone rings that are separated by an average of 3.4 Å. It is concluded that, upon drying, $14^+SbF_6^-$.2 $Et_2O$ undergoes a remarkable concerted hydroquinone ring slippage of ca. 3 Å with concomitant loss of hydrogen bonding to the ether and gain of π-π stacking interactions, all without the loss of crystallinity.

TABLE 7

| | 14+SbF6− | 14+SbF6−(hex) | 14+OTf− | 14+OPf− |
|---|---|---|---|---|
| formula | $C_{50}H_{56}F_6O_{10}P_2RhSb$ | $C_{42}H_{36}F_6O_8P_2RhSb$ | $C_{44}H_{38}Cl_2F_3O_{11}P_2RhS$ | $C_{42}H_{36}F_2O_{10}P_3Rh$ |
| fw | 1217.55 | 1069.31 | 1067.55 | 934.53 |
| T, K | 100(2) | 100(2) | 100(2) | 100(2) |
| cryst syst | Triclinic | Triclinic | Triclinic | Triclinic |
| space group | P-1 | P-1 | P1 | P1 |

Crystallographic Data

TABLE 7-continued

Crystallographic Data

| | | | | |
|---|---|---|---|---|
| a, Å | 12.834(1) | 10.669(2) | 10.597(1) | 10.843(1) |
| b, Å | 13.259(1) | 14.186(3) | 13.952(1) | 11.245(1) |
| c, Å | 17.158(1) | 16.884(3) | 16.587(1) | 17.908(1) |
| α, deg | 94.600(1) | 65.795(4) | 74.722(1) | 105.394(1) |
| β, deg | 99.863(1) | 85.774(4) | 84.604(2) | 90.398(1) |
| γ, deg | 116.234(1) | 70.863(4) | 70.769(1) | 107.279(1) |
| V, Å$^3$ | 2540(1) | 2196(1) | 2233(1) | 2001(1) |
| Z | 2 | 2 | 2 | 2 |
| $D_{calcd}$, g/cm$^3$ | 1.592 | 1.617 | 1.587 | 1.551 |
| F(000) | 1232 | 1064 | 1079 | 952 |
| cryst size, mm | 0.17 × 0.16 × 0.15 | 0.15 × 0.11 × 0.05 | 0.10 × 0.09 × 0.05 | 0.07 × 0.05 × 0.05 |
| θ range, deg | 1.74 to 28.42 | 1.65 to 26.47 | 1.60 to 26.45 | 1.98 to 26.55 |
| no. of rflns collected | 30290 | 23725 | 24103 | 21442 |
| no. of data/restraints/paramns | 12161/6/635 | 8995/0/541 | 17842/657/1123 | 16047/603/1020 |
| Goodness-of-fit on F$^2$ | 1.026 | 1.074 | 1.023 | 1.033 |
| final R indices [I > 2σ(1)] | R1 = 0.0377 | R1 = 0.1121 | R1 = 0.0758 | R1 = 0.0688 |
| | wR2 = 0.0808 | wR2 = 0.3021 | wR2 = 0.1221 | wR2 = 0.1385 |

| | 16+BF4− | 14+OTs− | 14+ClO4− |
|---|---|---|---|
| formula | $C_{48}H_{40}BF_4O_8P_2Rh$ | $C_{50}H_{45}Cl_2O_{11}P_2RhS$ | $C_{42}H_{36}ClO_{12}P_2Rh$ |
| fw | 996.46 | 1089.67 | 933.01 |
| T, K | 100(2) | 293(2) | 100(2) |
| cryst syst | Monoclinic | Orthorombic | Rhombohedral |
| space group | P2/c | P2$_1$2$_1$2$_1$ | R-3 |
| a, Å | 17.960(5) | 11.947(6) | 38.625(1) |
| b, Å | 11.306(3) | 17.660(8) | 38.625(1) |
| c, Å | 23.267(7) | 24.201(11) | 15.096(1) |
| α, deg | 90 | 90 | 90 |
| β, deg | 105.502(5) | 90 | 90 |
| γ, deg | 90 | 90 | 120 |
| V, Å$^3$ | 4553(2) | 5106(4) | 19505(2) |
| Z | 4 | 4 | 18 |
| $D_{calcd}$, g/cm$^3$ | 1.454 | 1.417 | 1.43 |
| F(000) | 2032 | 2232 | 8568 |
| cryst size, mm | 0.14 × 0.14 × 0.10 | 0.135 × 0.11 × 0.038 | 0.12 × 0.114 × 0.096 |
| θ range, deg | 1.82 to 23.25 | 1.43 to 28.79 | 1.48 to 28.38 |
| no. of rflns collected | 35882 | 57426 | 77869 |
| no. of data/restraints/paramns | 6529/730/618 | 12656/6/606 | 10732/0/523 |
| Goodness-of-fit on F$^2$ | 1.067 | 0.735 | 0.930 |
| final R indices [I > 2σ(1)] | R1 = 0.1212 | R1 = 0.0705 | R1 = 0.0762 |
| | wR2 = 0.2917 | wR2 = 0.1151 | wR2 = 0.2386 |

Figure 9:
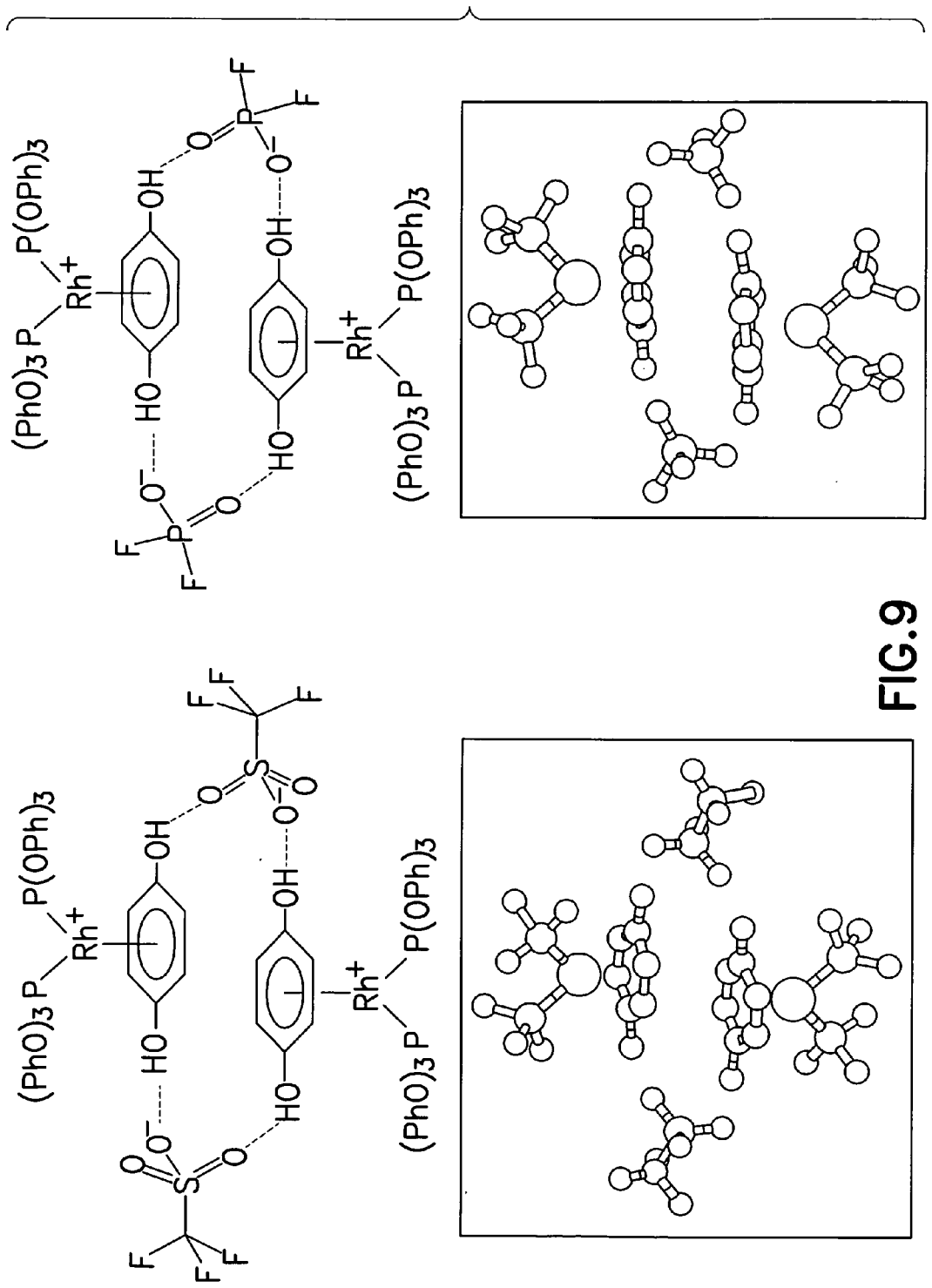
FIG. 9 shows dimeric structures of 14$^+$OTf$^-$ (left) and 14$^+$OPf$^-$, (right), both of which features charge assisted hydrogen bonding and π-π stacking interactions.

Crystals of the triflate salt 14$^+$OTf$^−$ were grown by layering hexane on a methylene chloride solution at −20° C. The solid state structure consists of the dimeric unit illustrated in FIG. 9 and follows the general pattern depicted in FIG. 7$a$. The two hydroquinone rings are π-π stacked (3.6 Å) and the —OH groups are hydrogen bonded to the sulfonate oxygens of the triflate anion (average O····O=2.65 Å). Since the sulfonate end of the triflate anion contains most of the net negative charge (vide infra), the hydrogen bonding would be expected to involve the oxygens rather than the fluorines, and may be classified as charge assisted.

The synthesis of 14$^+$PF$_6^−$, with AgPF$_6$ as the anion source, proceeded smoothly and gave a product with a satisfactory elemental analysis. After slow recrystallization from methylene chloride, however, it became evident from subsequent single crystal X-ray analysis and altered bulk elemental analysis that hydrolysis of the anion to PF$_2$O$_2^−$(OPf) had occurred during the recrystallization process. The hydrolysis reaction probably stems from trace water and may have been accelerated by the acidic nature of the coordinated hydroquinone. Hydrolysis of PF$_6^−$ in this manner has been observed previously. See Kannan, S.; James, A. J.; Sharp, P. R., *Inorg. Chim. Acta,* 2003, 345, 8. The X-ray structure of 14$^+$OPf$^−$ (FIG. 14) is very similar to that found for 14+OTf$^−$. Charge-assisted hydrogen bonding and π-π stacking (3.4 Å) interactions dominate the observed dimeric units. Careful analysis of the X-ray data confirmed that the hydrogen bonding from the hydroquinone —OH groups is to oxygen and not fluorine acceptors on the OPf$^−$ anion (average O····O=2.65 Å).

Figure 10:
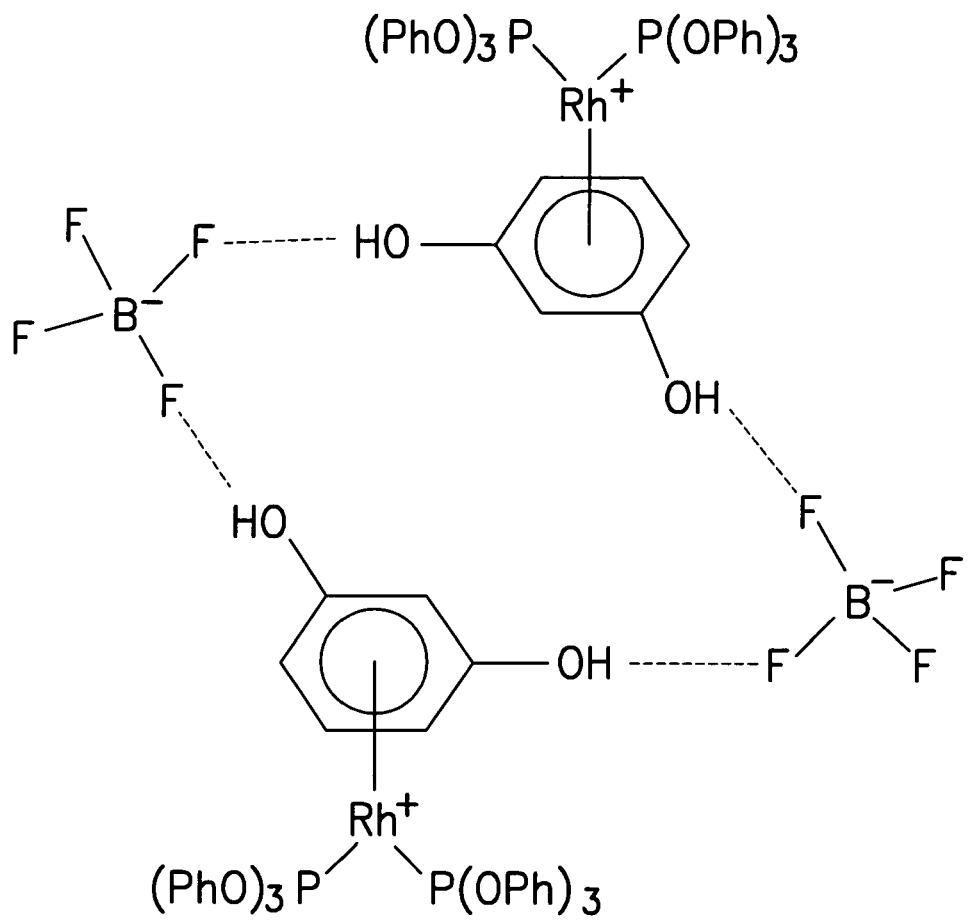
FIG. 10 shows the dimeric structure of 15$^+$BF$_4^-$.

The dimeric structure found for 14$^+$OPf$^−$ and 14$^+$OTf$^−$ combines in a cooperative manner three types of non-covalent interactions: charge-pairing, hydrogen bonding and π-π stacking. A different type of dimeric assembly was found for [(η$^6$-1,3-hydroquinone)Rh(P(OPh)$_3$)$_2$]$^+$BF$_4^−$ (15$^+$BF$_4^−$). In this case, the dimer is held together by charge-assisted hydrogen bonding but geometric restrictions prevent π-π stacking between the 1,3-hydroquinone rings (FIG. 10). The hydrogen bond distances in 15$^+$BF$_4^−$ average O····F=2.8 Å.

Figure 11:
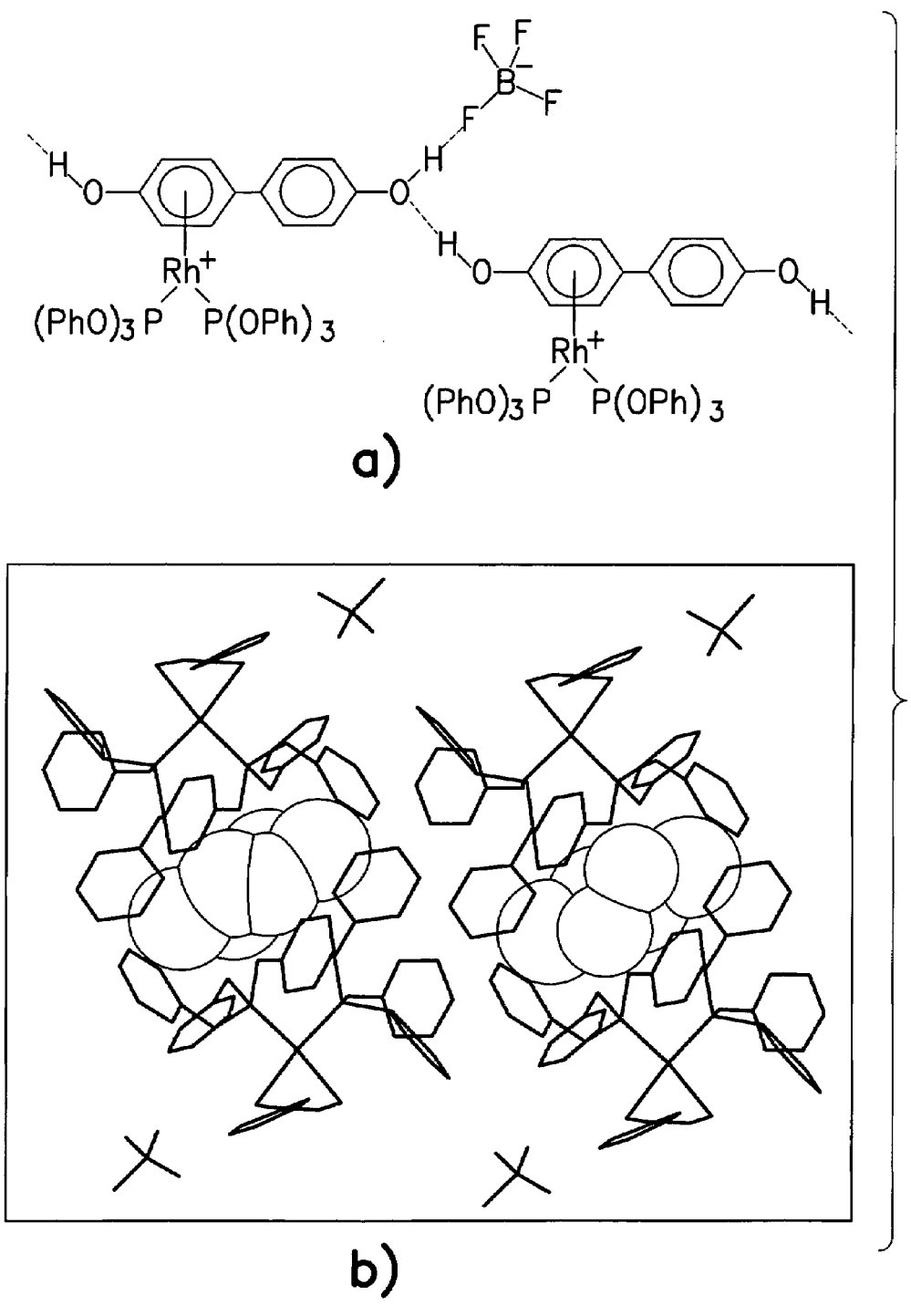
FIG. 11 shows (a) 1-D hydrogen bonded chain structure in 16$^+$BF$_4^-$ with (b) disordered solvent (violet) in channels that are lined with phenyl rings.
Figure 12:
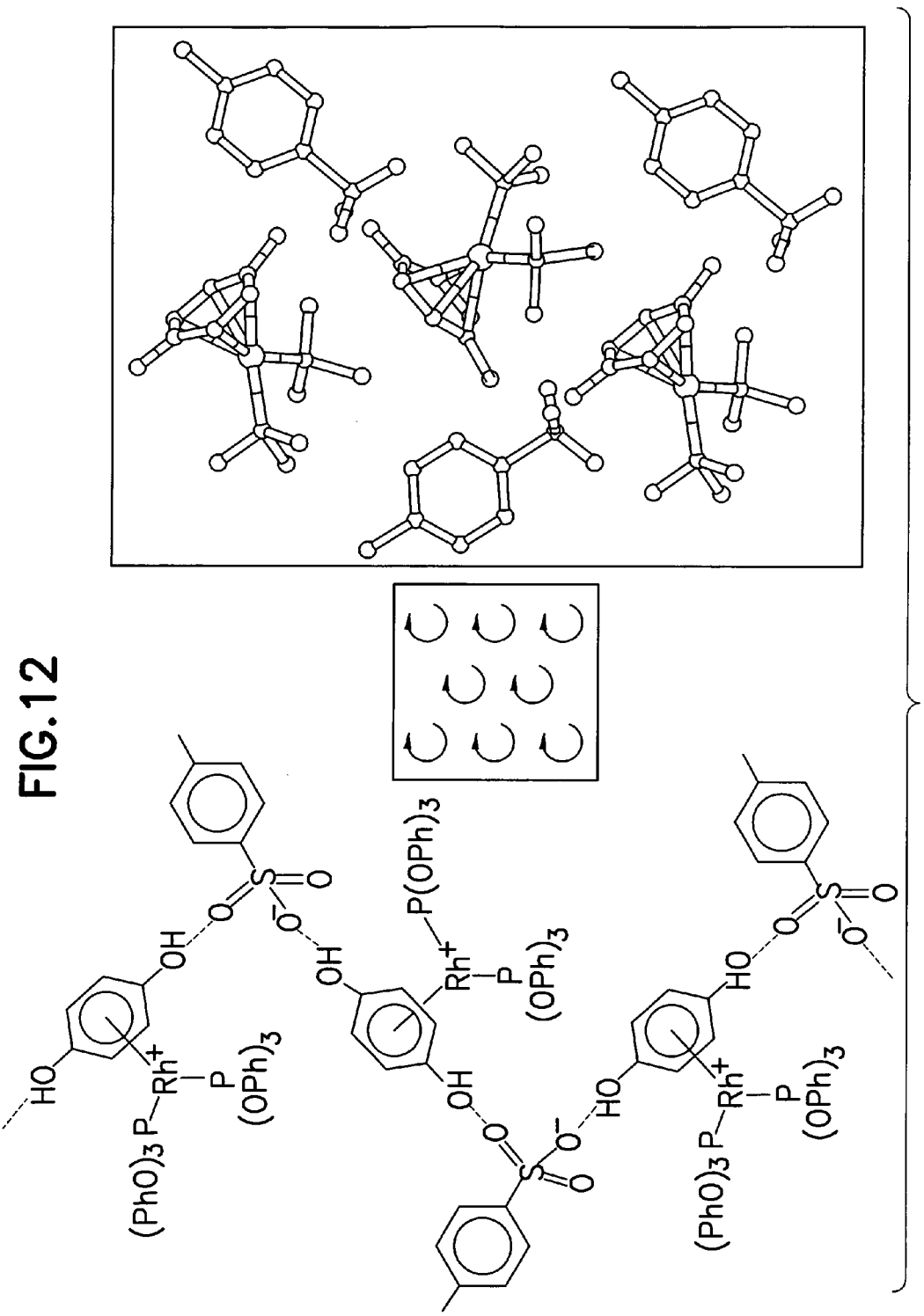
FIG. 12 showing the $C_2$ helical hydrogen bonded structure found in 14$^+$OTs$^-$. The helices all pack with the same twist direction, resulting in a chiral crystal.

[(η$^6$-4,4'-Biphenol)Rh(P(OPh)$_3$)$_2$]$^+$BF$_4^−$ (16$^+$BF$_4^−$) forms the hydrogen bonding network depicted in FIG. 12. Only one F atom in the BF$_4^−$ anion participates in hydrogen bond formation with the phenolic —OH groups. A 1-D polymeric chain structure results, shown in FIG. 11$a$, with the hydrogen bond distances O····F=2.6 Å and O····O=2.8 Å. The 3-D crystal structure features small channels which are lined with phenyl groups from the triphenyl phosphite ligands that undergo π-π stacking. The channels were found to be filled with unidentified disordered solvent molecules, (FIG. 11$b$).

Figure 7:
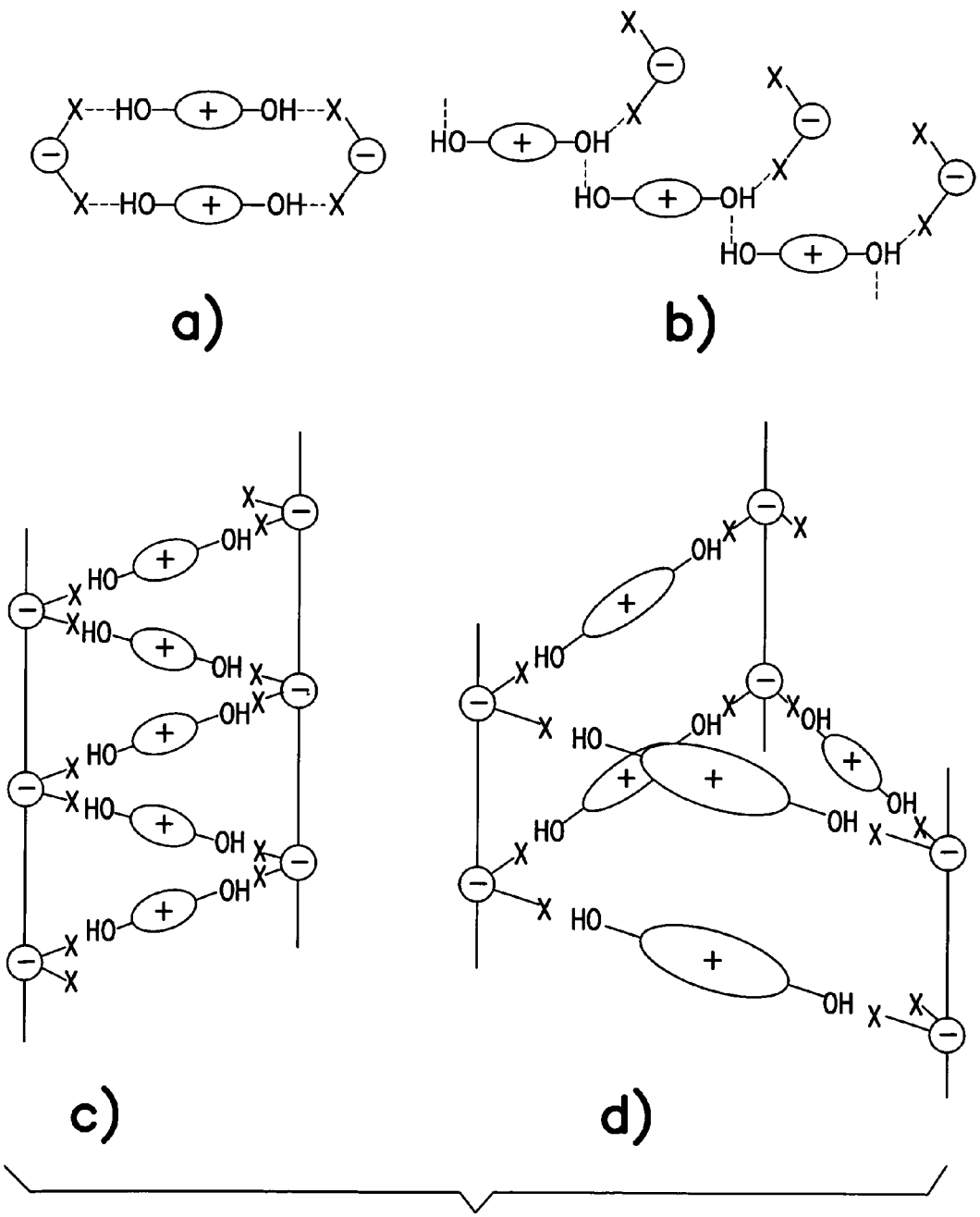
FIG. 7 shows hydrogen bonded structural patterns found in the solid state for [14$^+$-16$^+$]X$^-$ can be (a) dimeric, (b) 1-D chain, (c) $C_2$-helical, (d) $C_3$-helical.
Figure 8:
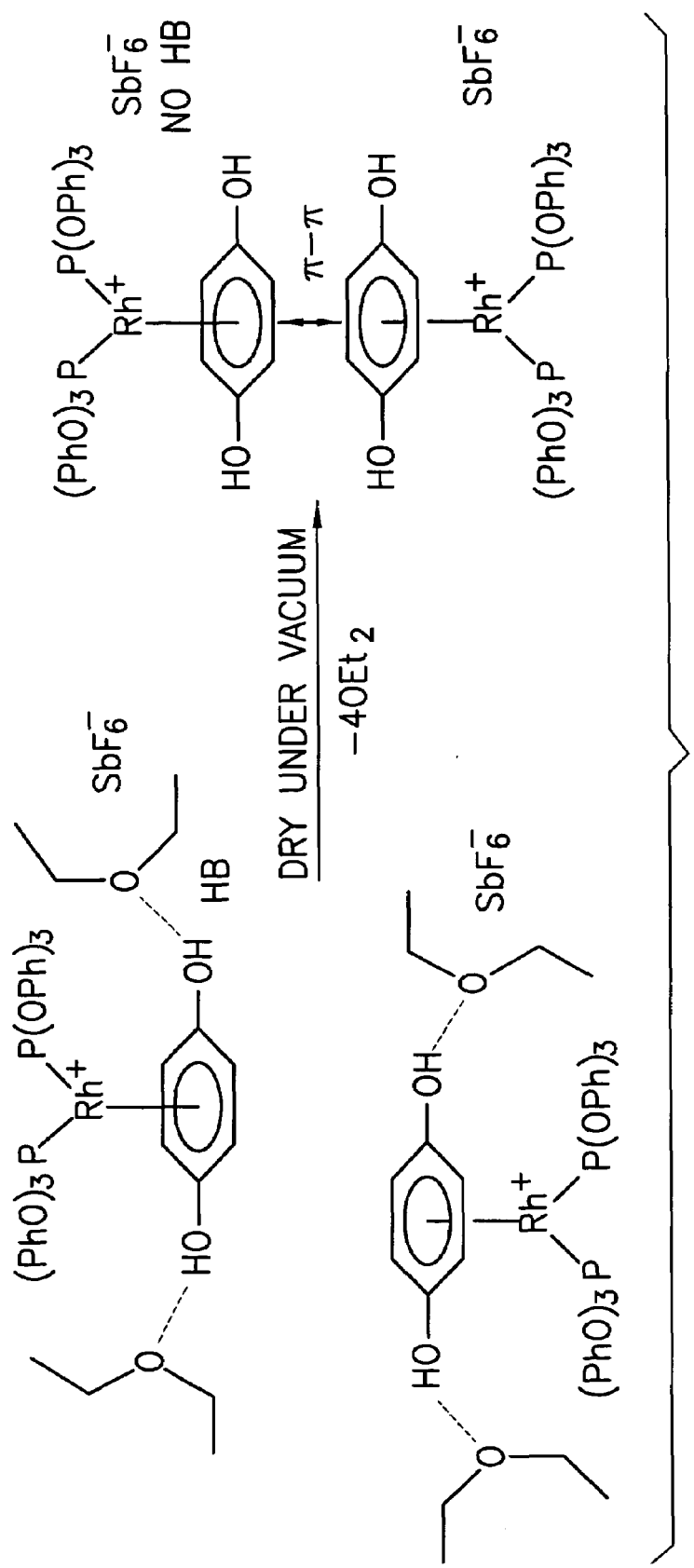
FIG. 8 shows hydrogen bonded structure of crystalline 14$^+$SbF$_6^-$ as a diethyl ether solvate (left) and slippage to a π-π stacked structure upon drying (right)

The C$_2$-helical chain motif shown in FIG. 7$c$ was found for the tosylate salt of [(η$^6$-1,4-hydroquinone)Rh(P(OPh)$_3$)$_2$]$^+$ (14$^+$OTs$^−$). Long rod-shaped single crystals of 14$^+$OTs$^−$ were grown by layering a methylene chloride solution with hexane at 0° C. The helical hydrogen bonding network has $C_2$ projection symmetry (FIG. 12). The space group ($P2_12_12_1$) implies the generation of chirality during the crystallization process, which means that the helices pack such that all possess the same direction of rotation (CW or CCW). The two independent hydrogen bonds in $14^+OTs^-$ have O••••O=2.43 and 2.67 Å.

Figure 14:
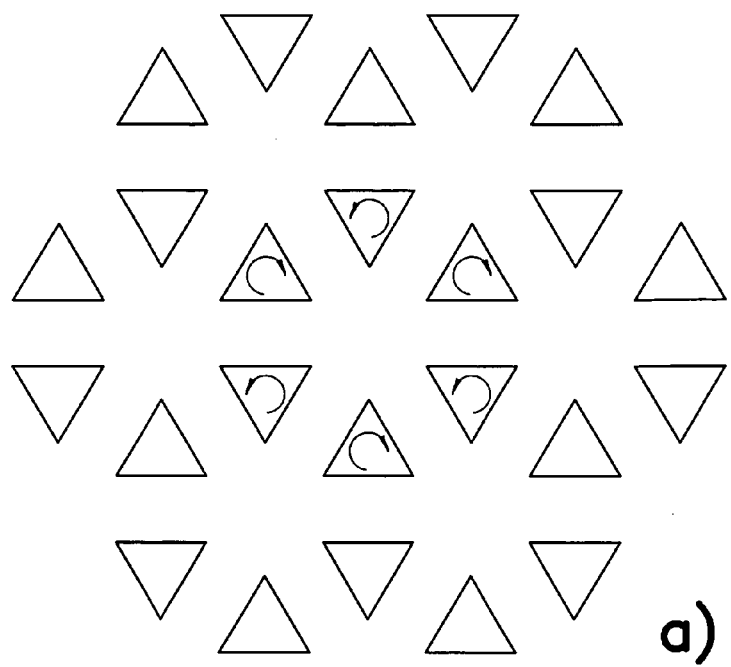
FIG. 14 shows (a) 3-D packing of the $C_3$ helices in 14$^+$ClO$_4^-$ and 14$^+$BF$_4^-$, and (b) a depiction of the resultant hydrophobic channels.
Figure 14:
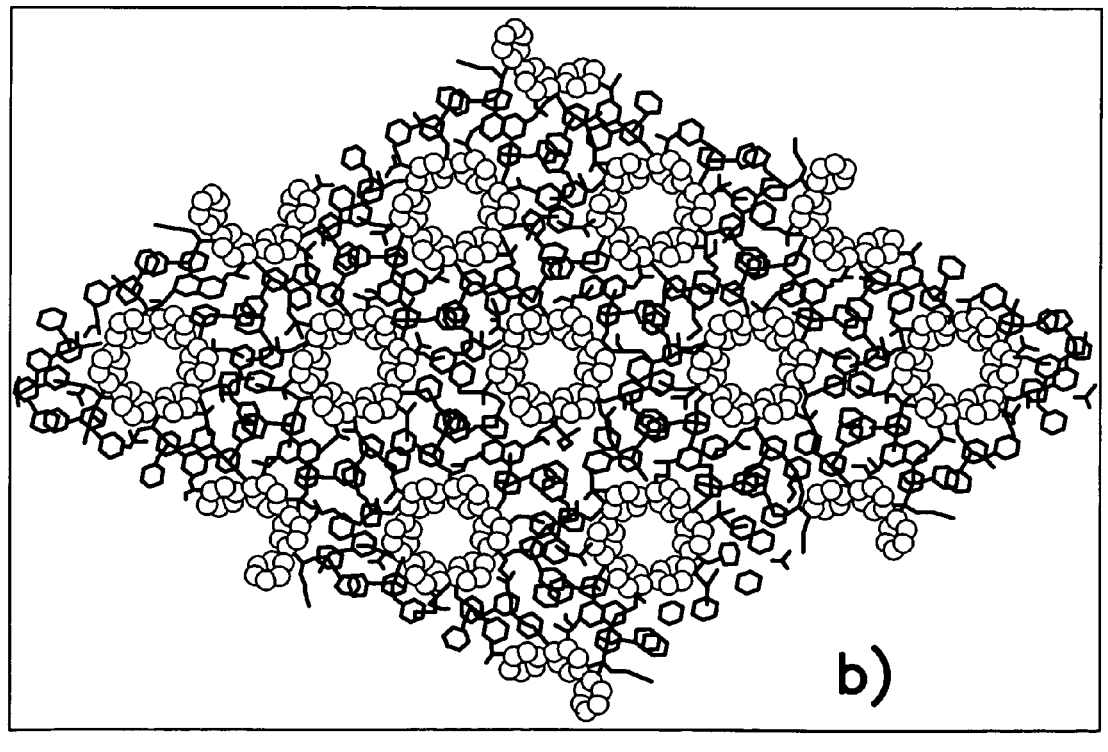

Single crystals of $14^+BF_4^-$ and $14^+ClO_4^-$ were grown by layering a methylene chloride solution with diethyl ether. These two salts have virtually identical structures, which feature the intriguing $C_3$-helical hydrogen bonded network shown in FIG. 7d. Structural details for $14^+ClO_4^-$ are shown in FIG. 13. The hydrogen bonding distances in $14^+BF_4^-$ are F••••O=2.47, 2.60 Å and those in $14^+ClO_4^-$ are O••••O=2.41, 2.91 Å. In each compound, six $C_3$ helices assemble to generate the hexagonal channels or pores illustrated in FIG. 14. The structure belongs to the centrosymmetric space group R-3 and the direction of rotation of the helices alternates around the channels. The channels themselves located at the core of the six helices consist of hydrophobic phosphite phenyl groups (FIG. 14). Two of the three phenyl groups from each P(OPh)$_3$ ligand contribute to the channels, which have a diameter of ca. 10.5 Å and are separated by ca. 23 Å.

The ease of formation of the pore structure shown in FIG. 14b for $14^+ClO_4^-$ and $14^+BF_4$ was investigated by comparing the XRPD pattern of slowly grown macrocrystals with that found for microcrystals obtained by rapid precipitation. The addition of diethyl ether to a methylene chloride solution of $14^+ClO_4^-$ led to rapid precipitation of a powder that appeared under a microscope to consist of good quality microcrystals. XRPD patterns showed that microcrystalline $1^+ClO_4^-$ formed by simple rapid precipitation is (i) indeed crystalline and (ii) has the same porous structure possessed by slowly grown single crystals (FIG. 14). We come to the significant conclusion that the dynamic processes occurring in the assembly of organometallic building block $14^+ClO_4^-$ into an intricate 3-D supramolecular architecture with hexagonal channels operate on a fast preparative time scale. Thus, the synthesis of crystalline porous materials such as 14+ClO$_4$— can be accomplished within seconds (precipitation) rather than requiring days (slow single crystal growth). See also: Son UK Seung, Reingold Jeffrey A., Carpenter Gene B., Czech Paul T., Sweigart Dwight A., *Organometallics* 2006. Analogous conclusions obtain for the $14^+BF_4^-$ analogue.

Experiments were done to probe the possible interaction of appropriate aromatic molecules with the hydrophobic channels present in $14^+ClO_4^-$ (FIG. 14). The XRPD pattern of solid $14^+ClO_4^-$ changes significantly after exposure to toluene for five days and then reverts to the original pattern after drying under vacuum. It may be concluded that toluene interacts reversibly with the host channels in 14+C104—.

Figure 15:
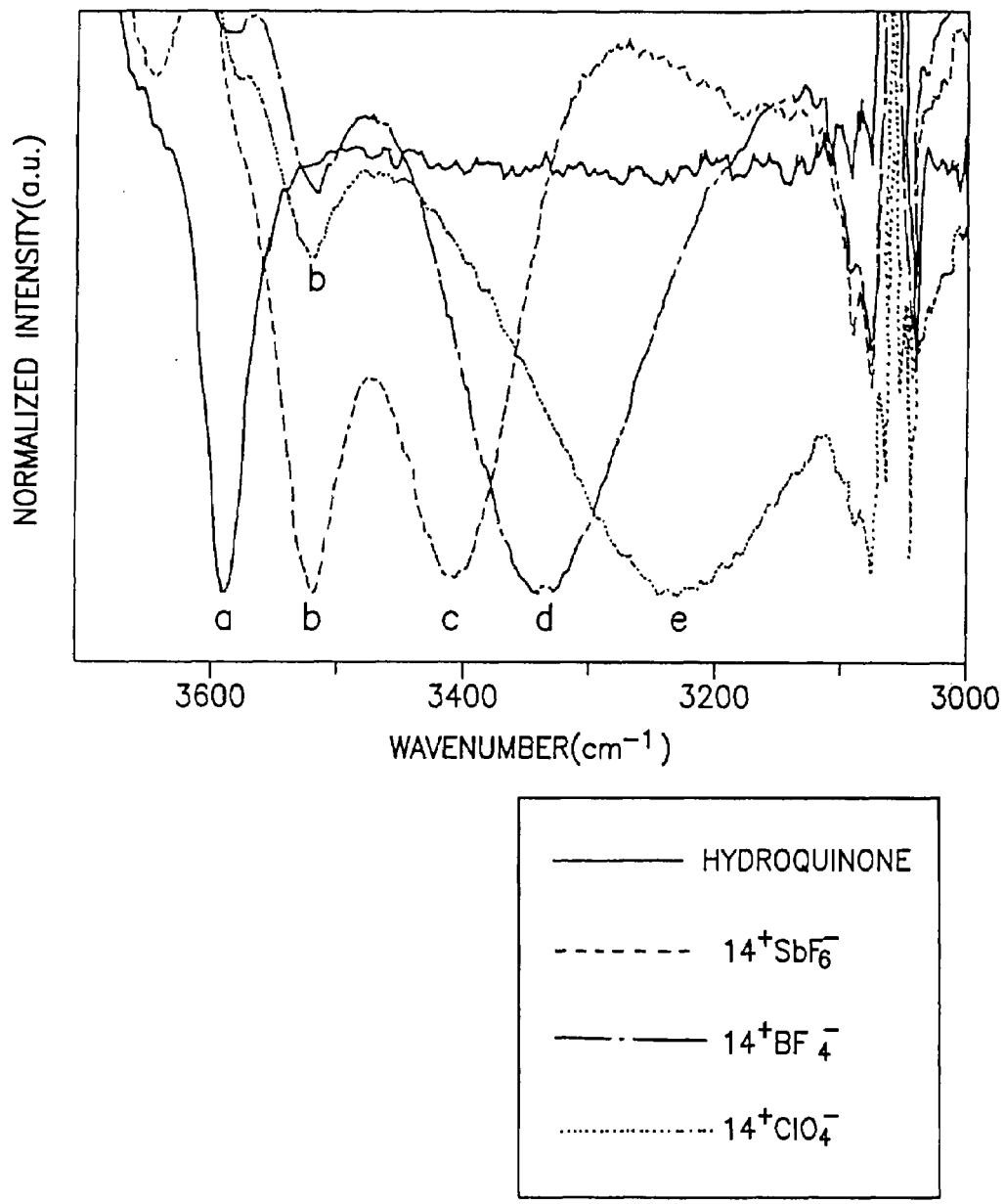
FIG. 15 shows IR spectra in the VOH region (11 mM, CH$_2$Cl$_2$ solvent) for (a) free 1,4-hydroquinone; (b) 14$^+$X$^-$ without hydrogen bonding between 14$^+$ and X$^-$; (c-e) 14$^+$X$^-$ with hydrogen bonding between 14$^-$ and the X$^-$.

The hydrogen bonding interactions between the organometallic cations and the counter anions shown in FIG. 6 were studied in methylene chloride solution via FT-IR. The results are summarized in FIG. 15 and in Table 8. As shown in FIG. 15, $v_{OH}$ in $14^+$ is red-shifted by hydrogen bonding to the anion. With $14^+SbF_6^-$, two IR peaks are seen at 3517 and 3405 cm$^{-1}$ (labeled b and c). The peak at 3517 cm$^{-1}$ is assigned to "free" $14^+$, i.e., the complex not hydrogen bonded to the counter anion. In support of this assertion, peak "b" also appears at the same frequency with counterions $BF_4^-$ and $Cl_4^-$. The much greater intensity of this peak in the case of $SbF_6^-$ reflects the relatively poor ability of $SbF_6^-$ to function as a hydrogen bond acceptor, a fact also indicated by the X-ray structures.

Peaks c-e in FIG. 15 are assigned to hydrogen bonded —OH groups. The shift of these $v_{OH}$ bands from the "free" position (peak b) can be used to estimate the strength of the H-bonding between the hydroquinone —OH groups and the counterion by application of Iogansen's equation. It is noted that the Iogansen equation related to hydrogen bonding enthalpy is $\Delta Ho=-1.28(\Delta v)\frac{1}{2}$. See also S. G. Kazarian, P. A. Hamley and M. Poliakoff, *J. Am. Chem. Soc.*, 1993, 115, 9069; A. V. Iogansen, G. A. Kurkchi, V. M. Furman, V. P. Glazunov and S. E. Odinokov, *Zh. Prikl. Spektrosk.*, 1980, 33, 460. The results, presented in Table 8, indicate that H-bonding between $14^+$ or $15^+$ and the counter anion is greater for O-based acceptors than for F-based acceptors. The hydrogen bonding strength spans the range 14-27 kJ/mol and follows the order $SbF_6^-<BF_4^-<ClO_4^-\leq OTf<OPf^-$, $OTs^-$.

TABLE 8

Summary of IR Study of Hydrogen Bonding[a]

| Compound | Free $v_{OH}$ (cm$^{-1}$) | H-bonded $v_{OH}$ (cm$^{-1}$) | Shift in $v_{OH}$ (cm$^{-1}$) | $-\Delta H^b$ (kJ/mol) |
|---|---|---|---|---|
| hydroquinone | 3585[c] | | | |
| Resorcinol | 3580 | | | |
| 4,4'-biphenol | 3598 | | | |
| $1^+ClO_4^-$ | 3517[d] | 3231 | 286 | 21.6 |
| $1^+OTf^-$ | 3517[d] | 3170 | 347 | 23.8 |
| $1^+OPf^-$ | 3517[d] | 3078 | 439 | 26.8 |
| $1^+OTs^-$ | 3517[d] | 3058 | 459 | 27.4 |
| $1^+BF_4^-$ | 3517[d] | 3330 | 187 | 17.5 |
| $1^+SbF_6^-$ | 3517[d] | 3405 | 112 | 13.5 |
| $2^+BF_4^-$ | 3505[d] | 3321 | 184 | 17.4 |
| $3^+BF_4^-$ | 3573[e] | 3296 | | |

The $v_{OH}$ bands in the IR spectra of free hydroquinone, resorcinol and 4,4'-biphenol were found to be invariant over the concentration range utilized (3-11 mM), indicating the absence of intermolecular hydrogen bonding at these concentrations. In contrast, FIG. 15 clearly shows that hydrogen bonding in $14^+X^-$ can be extensive at 11 mM. The enhanced hydrogen bonding in $14^+X^-$ can be attributed to (1) the positive charge on the cation brought about by the electrophilic rhodium fragment and (2) the obligatory anionic counterion that can act as a hydrogen bond acceptor. Charge pairing of the species in $14^+X^-$ undoubtedly complements the hydrogen bonding. In order to probe the "charge assisted" nature of the hydrogen bonding, IR spectra of $CH_2Cl_2$ solutions of 1,4-hydroquinone (11 mM) containing varying amounts of $Bu_4ClO_4$ were recorded. One equivalent of $Bu_4NClO_4$ has little effect on the IR spectrum and even with ten equivalents of $Bu_4NClO_4$ present, a significant amount of free hydroquinone remains. It is concluded that the hydrogen bonding observed with $(14^+-16^+)$, $X^-$ has as important components both ionic charge pairing and electrophilic activation imparted by coordination to the transition metal.

Next, molecular orbital calculations were performed using Spartan to assign atomic charges to the key terminal atoms for the range of counterions. Atomic charges are notoriously difficult to define which led us to include the results from three differing approaches. See Spartan '04, Version 1.0.3; Wavefunction, Inc., Irvine, Calif. 2004 and Hehre, W. J. *A Guide to Molecular Mechanics and Quantum Chemical Calculations*, Chapter 16, Wavefunction, Inc., Irvine Calif. 2003. Regardless of the charge partitioning scheme used, the oxygen atoms are calculated to be more electron-rich than the fluorine atoms. These results are in agreement with the observed preference for charge-assisted hydrogen-bonding to oxygen over fluorine in $OTf^-$ and $OPf^-$, as well as the trends observed in the IR spectra.

In crystal engineering, it is common for slight modification in ligand geometry and/or reaction conditions to result in supramolecular isomerization. This is typically the reason it is difficult to rationally design or predict supramolecular structures. In the case of 14$^+$BF$_4^-$ and 15$^+$BF$_4^-$ it is interesting that two iso-structures can be obtained from the self-assembly of geometrically different building blocks. This suggests that the bulky triphenyl phosphite groups, which are common to 14$^+$BF$_4^-$, 14$^+$ClO$_4^-$ and 15$^+$BF$_4^-$, play a major role in the supramolecular construction. This hypothesis is strengthened by an examination of the chemical composition of the channels.

Figure 16:
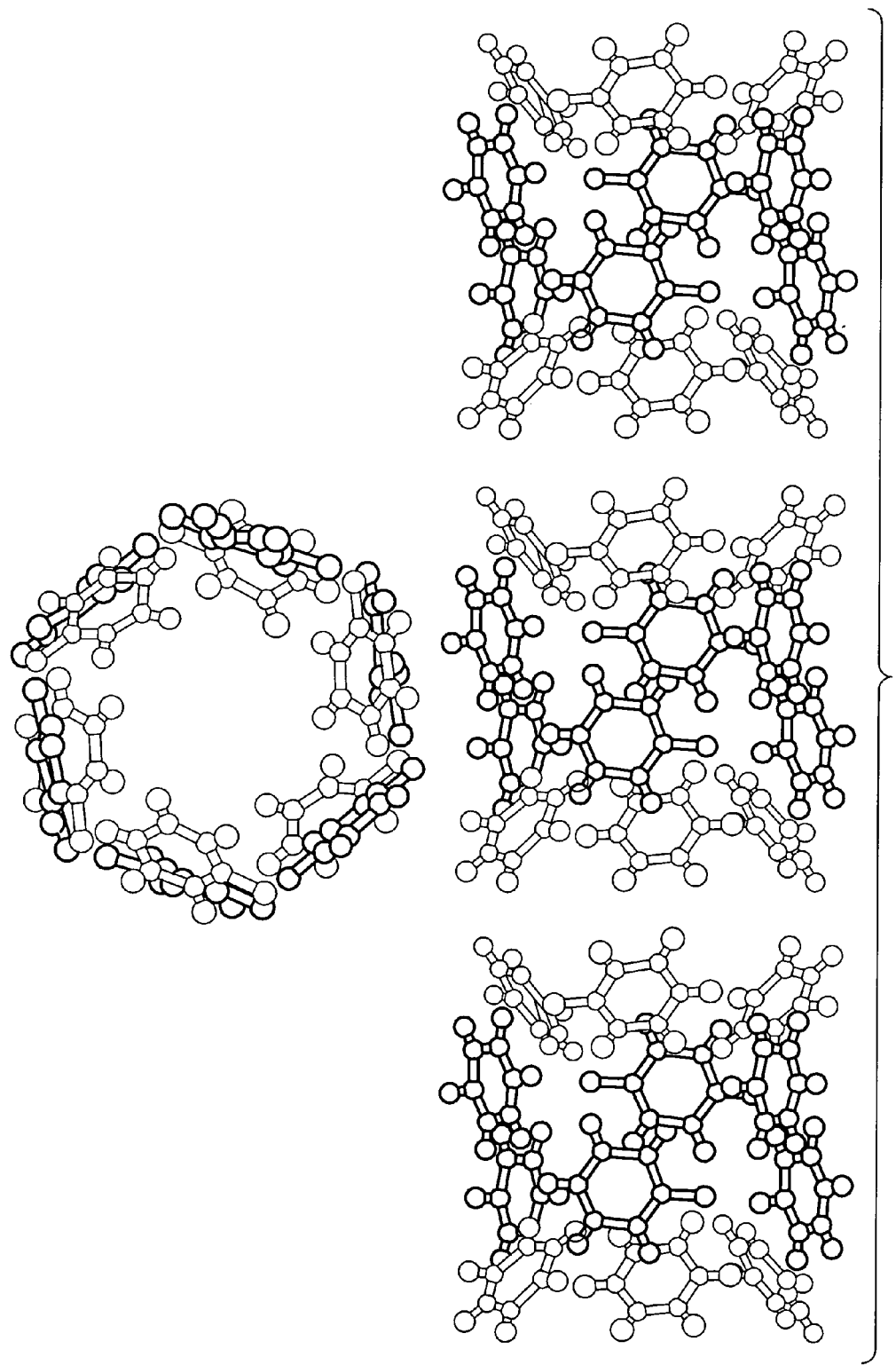
FIG. 16 shows views perpendicular and parallel to the channel axis in 14$^+$BF$_4^-$; two types of phenyl groups are shown.

The channels or pores located at the core of the six helices in 14$^+$BF$_4^-$ and in 14$^+$ClO$_4^-$ include hydrophobic phosphite phenyl groups (FIG. 14). Two of the three phenyl groups from each P(OPh)$_3$ ligand contribute to the channels. FIG. 16 illustrates the view perpendicular and parallel to the channel axis. There are two types of phenyl groups present: half are situated parallel to the channel axis and define a pore diameter of ca. 10.5 Å; the other half are inclined by ca. 45° to the axis, reducing the effective pore diameter to ca. 6 Å. These two subgroups together form interesting sphere like units linked by linear units. In 15$^+$BF$_4^-$ completely analogous channels exist with the difference that the phenyl groups are more inclined (ca. 75°), with the result that the channels are much more blocked in comparison to the situation in 14$^+$BF$_4^-$ and 14$^+$ClO$_4^-$.

The micropores in 14$^+$BF$_4^-$ are likely to be robust because the hydrogen bonding is "charge-assisted" by coulombic interactions. Complementing this is the relatively small pore size and the large distance of ca. 23 Å between successive pore centers. See: B. Moulton and M. J. Zaworotko, *Curr. Opin. Sol. State Mat. Sci.*, 2002, 6, 117. Metal-organic networks with pores in the size range reported herein have recently been found to be excellent hosts for suitably small guest molecules (e.g., acetylene). Aside from size the important factor influencing adsorption is the chemical environment of the pore interior. In the case of 14$^+$BF$_4^-$ and 14$^+$ClO$_4^-$, the channels or pores consist of aromatic rings, which may make the material a particularly useful model for hydrogen adsorption. See: B. Kesanli, Y. Cui, M. R. Smith, E. W. Bittner, B. C. Bockrath and W. Lin, *Angew. Chem. Int. Ed.*, 2005, 44, 72.

In summary, the complexes [(1,4- and 1,3-hydroquinone)Rh(P(OPh)$_3$)$_2$]BF$_4$ (14$^+$BF$_4^-$, 15$^+$BF$_4^-$) were found to exhibit charge assisted hydrogen bonding between the —OH groups and the BF$_4^-$ or ClO$_4^-$ counterion. In the solid state, this hydrogen bonding interaction gives rise to iso-structural supramolecular networks containing hydrophobic channels that consist of phenyl groups from the triphenyl phosphite ligands. Applications of these materials to guest-host chemistry are being examined.

Additionally, porous media for gas storage has potential applications in the development of hydrogen storage systems. Rhodium quinones are not believed to have been used before for this purpose. The rhodium hydroquinone cationic complex [(hydroquinone)RhL$_2$]$^+$X$^-$ has a solid state structure that is dominated by charge assisted hydrogen bonding and pi-pi stacking of the aromatic rings. With anions such as tetrafluoroborate and perchlorate, the solid material possesses hydrophobic channels that are lined with aromatic rings and that may provide an excellent environment for modeling the storage of hydrogen gas for application in storage and transport for energy applications.

It is further noted that additional crystallographic (CIF) data have been deposited with the Cambridge Crystallographic Data Center as registry numbers CCDC 285472, 285473 and 299584-299590. See Table 8 for crystal data.

Additional data are as follows: for 14$^+$BF$_4^-$: C$_{42}$H$_{36}$O$_8$P$_2$B$_1$F$_4$Rh$_1$, M=920.37, rhombohedral, space group R-3, a=38.46(1), b=38.46(1), c=14.93(1) Å, α=90, β=90, γ=120°, V=19125(2) Å$^3$, Z=18, F(000)=8424, gof=0.855, final R1=0.0743; Crystal Data for 15$^+$BF$_4^-$: C$_{42}$H$_{36}$O$_8$P$_2$B$_1$F$_4$Rh$_1$, M=920.37, rhombohedral, space group R-3, a=38.72(1), b=38.72(1), c=14.66(1) Å, α=90, β=90, γ=120°, V=19037(4) Å$^3$, Z=18, F(000)=8424, gof=1.098, final R1=0.0895

Synthetic Procedures and Characterization

General Considerations All reactions were carried out under N$_2$ in flame-dried glassware. HPLC grade methylene chloride and diethyl ether solvents were used as received without further purification. [Rh(COD)Cl]$_2$ was provided by Strem Chemicals. The $^1$H NMR spectra were recorded on Bruker (300 MHz) spectrometers. Elementary analyses were performed by Quantitative Technologies Inc. (QTI, New Jersey). Thermogravimetric analyses (TGA, Q500 from Texas Instruments) and differential scanning calorimetry (DSC, DuPont DSC 2910) were performed at a scan rate of 5° C./min and 10° C./min using N$_2$, respectively. X-ray powder diffraction (XRPD) data were recorded on a Bruker D8 ADVANCE at 40 kV and 40 mA with Cu Kα radiation (λ=1.54050 Å) and a scan speed of 0.3°/sec and a step size of 0.1° in 2θ.

(η$^6$-1,4-Hydroquinone)Rh[bis(triphenylphosphite)]BF$_4$ (14$^+$BF$_4^-$). After flame drying the glassware, [Rh(P(OPh)$_3$)$_2$Cl]$_2$ (0.36 g, 0.24 mmol) and AgBF$_4$ (0.11 g, 0.56 mmol) were mixed for 1 h at room temperature in methylene chloride (5 mL). While stirring, a white precipitate was formed on the bottom of the glassware. 1,4-hydroquinone (0.10 g, 0.91 mmol) was added to the reaction mixture. After stirring for 2 h at r.t., the solvent was removed using rotary evaporator. The residue was dissolved in methylene chloride (3 mL) and slowly dropped to ethereal solution trough the Celite pad. The formed yellow solid in ether was collected by filter and washed with diethyl ether (10 mL, three times). The isolated yield was 71% (0.31 g, 0.34 mmol). To get the crystals: η$^6$-1,4-hydroquinone Rh[bis(triphenylphosphite)]$^+$BF$_4^-$ (30 mg) was dissolved in methylene chloride (1.0 mL) in 5 mL-vial. Diethylether (3 mL) was carefully added to upper layer. After standing in a refrigerator for 3 days, reddish-yellow crystals formed on the wall of vial. $^1$H NMR (CD$_2$Cl$_2$): δ 7.36(t, J=7.8 Hz, OPh, 12H) 7.26 (t, J=7.6 Hz, OPh, 6H), 7.02 (d, J=8.0 Hz, OPh, 12H), 6.56 (brs, OH, 2H), 5.63 (s, hydroquinone ring, 4H) ppm. Elemental Anal. Calcd for C$_{42}$O$_8$H$_{36}$P$_2$Rh$_1$B$_1$F$_4$: C, 54.81; H, 3.94. Found: C, 54.66; H, 3.86.

(η$^6$-1,4-Hydroquinone)Rh[bis(triphenylphosphite)]ClO$_4$ (14$^+$ClO$_4^-$). The same procedure was followed using AgClO$_4$ instead of AgBF$_4$. The isolated yield was 79%. Crystals of 14$^+$ClO$_4^-$ were grown by layering a methylene chloride solution with hexane and cooling in a refrigerator for four days. $^1$H NMR (CD$_2$Cl$_2$): δ 7.37(t, J=7.9 Hz, OPh, 12H), 7.25 (t, J=7.8 Hz, OPh, 6H), 7.01 (d, J=7.8 Hz, OPh, 12H), 6.96 (br s, OH, 2H), 5.67 (s, hydroquinone ring, 4H). Elemental anal. Calcd (%) for C$_{42}$O$_{12}$H$_{36}$P$_2$Rh$_1$Cl$_1$: C, 54.07; H, 3.89. Found (%): C, 54.08; H, 4.01.

(η$^6$-1,4-Hydroquinone)Rh[bis(triphenylphosphite)]SbF$_6$ (14$^+$SbF$_6^-$). After flame drying the glassware, [Rh(P(OPh)$_3$)$_2$Cl]$_2$ (0.36 g, 0.24 mmol) and AgSbF$_6$ (0.19 g, 0.56 mmol) were mixed for 1 h at room temperature in methylene chloride (5 mL). While stirring, a white precipitate formed on the bottom of the glassware after which 1,4-hydroquinone (0.10 g, 0.91 mmol) was added to the reaction mixture. After stirring for 2 h at RT, the solvent was removed by rotary evaporation. The residue was dissolved in methylene chloride (3 mL) and slowly dropped into an ether solution through a Celite pad. A yellow solid formed in the ether solution and was collected by filtration (washed with diethyl ether, 10 mL, three times). The isolated yield was 83% (0.42 g, 0.39 mmol). Crystals were grown by dissolving 14$^+$SbF$_6^-$ (30 mg) in methylene chloride (1.0 mL) in a 5 mL-vial and layering with 3 mL of diethyl ether. The solution was placed in a refrigerator for 2 weeks, after which yellow crystals formed on the wall of the vial. $^1$H NMR (CD$_2$Cl$_2$): δ 7.37(t, J=7.8 Hz, OPh, 12H), 7.27 (t, J=7.6 Hz, OPh, 6H), 7.03 (d, J=7.8 Hz, OPh, 12H), 6.11 (br s, OH, 2H), 5.68 (s, hydroquinone ring, 4H). Elemental anal. calcd (%) for C$_{42}$O$_8$H$_{36}$P$_2$Rh$_1$Sb$_1$F$_6$: C, 47.18; H, 3.39. Found: C, 47.85; H, 3.48.

(η$^6$-1,4-Hydroquinone)Rh[bis(triphenylphosphite)]TfO (14$^+$ OTf). The same procedure as above was followed using AgOTf instead of AgSbF$_6$. The isolated yield was 91%. Crystals of 14$^+$OTf$^-$ were grown by layering a methylene chloride solution with hexane and cooling in a refrigerator for two days. Yellow crystals formed on the wall of vial. $^1$H NMR (CD$_2$Cl$_2$): δ 8.26 (br s, OH, 2H), 7.31 (t, J=8.0 Hz, OPh, 12H), 7.21 (t, J=7.9 Hz, OPh, 6H), 6.97 (d, J=8.0 Hz, OPh, 12H), 5.47 (s, hydroquinone ring, 4H). Elemental anal. calcd (%) for C$_{43}$O$_{11}$H$_{36}$P$_2$Rh$_1$S$_1$F$_3$: C, 52.56; H, 3.69. Found (%): C, 53.08; H, 3.63.

(η$^6$-1,4-Hydroquinone)Rh[bis(triphenylphosphite)] PF$_2$O$_2$ (14$^+$ OPf). The same procedure as above was followed using AgPF$_6$ instead of AgSbF$_6$. Before recrystallization, the complex had PF$_6^-$ as the counter anion. Elemental anal. calcd (%) for C$_{42}$O$_8$H$_{36}$P$_3$Rh$_1$F$_6$: C, 51.55; H, 3.71. Found (%): C, 52.04; H, 3.69. During recrystallization from methylene chloride, however, hydrolysis of the anion to PF$_2$O$_2^-$ (OPf$^-$) occurred to afford 14$^+$OPf$^-$ in a 66% isolated yield. $^1$H NMR (CD$_2$Cl$_2$): δ 9.59 (brs, OH, 2H), 7.37 (t, J=8.0 Hz, OPh, 12H), 7.20 (t, J=7.9 Hz, OPh, 6H), 6.98 (d, J=8.0 Hz, OPh, 12H), 5.50 (s, hydroquinone ring, 4H). Elemental anal. Calcd (%) for C$_{42}$O$_{10}$H$_{36}$P$_3$Rh$_1$F$_2$: C, 53.98; H, 3.88. Found (%): C, 53.50; H, 3.73.

(η$^6$-1,4-Hydroquinone)Rh[bis(triphenylphosphite)]OTs (14$^+$ OTs$^-$). The same procedure was followed using silver tosylate instead of AgSbF$_6$. The isolated yield was 95%. Crystals of 14$^+$OTs$^-$ were grown by layering a methylene chloride solution with hexane and cooling in a refrigerator for three days. $^1$H NMR (CD$_2$Cl$_2$): δ 7.38 (d, J=7.5 Hz, OTs, 2H), 7.27 (t, J=7.8 Hz, OPh, 12H), 7.25 (d, J=7.5 Hz, OTs, 2H), 7.15 (t, J=7.6 Hz, OPh, 6H), 6.95 (d, J=7.8 Hz, OPh, 12H), 6.69 (br s, OH, 2H), 5.55 (s, hydroquinone ring, 4H), 2.39 (s, OTs methyl, 3H). Elemental anal. Calcd (%) for C$_{50}$O$_{11}$H$_{43}$P$_2$Rh$_1$S$_1$: C, 54.81; H, 3.94. Found (%): C, 54.66; H, 3.86.

(η$^6$-Resorcinol)Rh[bis(triphenylphosphite)]BF$_4$ (14$^+$BF$_4^-$). The same procedure as above was followed but using resorcinol instead of hydroquinone. The isolated yield was 89%. To get the crystals: (η$^6$-resorcinol)Rh[bis(triphenylphosphite)]$^+$BF$_4^-$ (25 mg) was dissolved in methylene chloride (0.7 mL) in a 5 mL vial. Toluene (3 mL) was carefully added to upper layer. The solution stands in refrigerator for 3 days. The orange crystals were formed on the wall of vial. $^1$H NMR (CD$_2$Cl$_2$): δ 8.41 (brs, OH, 2H), 7.35 (t, J=7.8 Hz, protons in OPh, 12H), 7.25 (t, J=7.6 Hz, OPh, 6H), 7.02 (t, J=7.00, resorcinol, 1H), 7.00 (d, J=7.8 Hz, OPh, 12H), 6.31 (s, resorcinol, 1H), 4.88 (d, J=7.8 Hz, resorcinol, 2H) ppm. Elemental Anal. Calcd for C$_{42}$O$_8$H$_{36}$P$_2$Rh$_1$B$_1$F$_4$: C, 54.81; H, 3.94. Found: C, 54.55; H, 4.10.

(η$^6$-4,4-Biphenol)Rh[bis(triphenylphosphite)]BF$_4$ (16$^+$BF$_4^-$). The same procedure was as above was followed using 4,4-biphenol instead of hydroquinone. The isolated yield was 87%. Crystals of 16$^+$BF$_4^-$ were grown by layering a methylene chloride solution with hexane and cooling in a refrigerator for three days. Orange crystals formed on the wall of vial. $^1$H NMR (CD$_2$Cl$_2$): δ 8.39 (br s, OH, 1H), 7.26 (t, J=7.5 Hz, OPh, 12H), 7.22 (t, J=7.5 Hz, OPh, 6H), 6.90 (t, J=7.6 Hz, OPh, 6H), 6.83 (d, J=8.9 Hz, biphenol, 2H), 6.75 (d, J=6.75 Hz, biphenol, 2H), 6.00 (br s, OH, 1H), 5.92 (s, biphenol, 4H). Elemental anal. Calcd (%) for C$_{48}$O$_8$H$_{40}$P$_2$Rh$_1$B$_1$F$_4$: C, 57.86; H, 4.05. Found (%): C, 57.74; H, 3.91.

Single Crystal X-ray Structure. X-ray data collection was carried out using a Bruker single-crystal diffractometer equipped with an APEX CCD area detector and controlled by SMART version 5.0. Collection was done either at 100 K or 293K. Data reduction was performed by SAINT version 6.0. The structures were generally determined by direct methods and refined on F squared by use of programs in SHELXTL version 5.0. Most hydrogen atoms appeared in a difference map, or they were generally inserted in ideal positions, riding on the atoms to which they are attached.

In view of the foregoing, it can be seen that novel embodiments include, for example, the combination of rhodium and quinones for use in catalysis and use in generation of new organolithium reagents. Only a few rhodium quinones have been previously reported and none with the chemical formula or constitution set forth herein, and none that are believed to have been applied or are believed likely to be useful for any of the uses mentioned above. The rhodium and quinone components both play an integral role in the uses. In catalysis, the compounds function as multifunctional catalysts, which is also believed to be unique, in that, for example, the quinone part binds to a substrate while the rhodium center acts as a receptor site for a second substrate.

In conclusion, it should be noted that some of the features of the various non-limiting embodiments of this invention may be used to advantage without the corresponding use of other features. As such, the foregoing description should be considered as merely illustrative of the principles, teachings and exemplary embodiments of this invention, and not in limitation thereof. Also, the numerical values, such as temperature, weight percent, etc., may also be understood in approximate (about) values.

What is claimed is:

1. A method of making cyclic compound comprising combining in a reaction mixture an aryl boronic compound, a conjugate acceptor and a rhodium quinonoid catalyst under suitable reaction conditions, allowing the reaction to proceed to its end, and isolating the desired cyclic compound from the reaction mixture.

2. The method of claim 1 comprising using the rhodium quinonoid catalyst for conjugate addition of a boronic substrate of the boronic compound comprising transferring a carbon group from the boronic compound to the conjugate acceptor via the rhodium quinonoid catalyst; and forming a product of conjugate addition.

3. The method of claim 2 comprising:
    combining the boronic compound, rhodium quinonoid catalyst, conjugate acceptor and a solvent, wherein the boronic compound is an aryl boronic acid, the conjugate acceptor is enone and the solvent is dimethoxyethane;
    adding an aqueous solution of LiOH base followed by deoxygenated H$_2$O to obtain a mixture;
    stirring the mixture at about 50° C. for about 1 hour;
    then diluting the mixture with a solution of NH$_4$Cl, extracted with EtOAc/hexanes and dried Na$_2$SO$_4$; followed by filtering to obtain the desired compound.

4. The method of claim 2 wherein the carbon group is a sp2 carbon group.

5. The method of claim 2 wherein the catalyst comprises the formula (V)

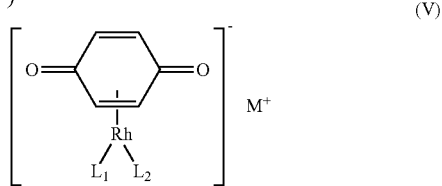
(V)

wherein $L_1$ and $L_2$ are each a ligand that donates electron density to rhodium to stabilize it;

wherein $M^+$ is a positively charged ion including any metal ion having an oxidation state at or higher than +1.

6. The method of claim 5 wherein $M^+$ is selected from the group consisting of cationic Li, K, Cs, Be, Sr, Ba, Al, Ti, Zr, B, Si, Cd, Ag, $Ph_3PNPPh_3$, Rb, $Mg^{2+}$, $Ca^{2+}$, Na, $R_4N^+$, $Zn^{2+}$, ammonium salts including tetraalkylammonium cations, tetraalkylarsonium cations, guanidinium salts, amidinium salts, and combinations thereof;

and $L_1$ and $L_2$ are identical or non-identical ligands that are either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof.

7. The method of claim 2 wherein the catalyst comprises an anionic rhodium $\eta^4$-quinonoid complex.

8. The method of claim 7 wherein the catalyst is a multifunctional catalyst for the arylation of aldehydes with arylboronic acids.

9. The method of claim 7 wherein the complex comprises $1^+BF_4^-$ or $2^+BF_4^-$.

10. The method of claim 7 wherein the rhodium complex comprises anionic rhodium $\eta^4$-quinonoid complex 3.K.

11. The method of claim 2 comprising about 0.1 to 1.0 mol % $Rh^1$ catalyst.

12. The method of claim 1 wherein the conjugate acceptor is is 2-cyclohexen-1-one.

13. The method of claim 2 comprising a reaction:

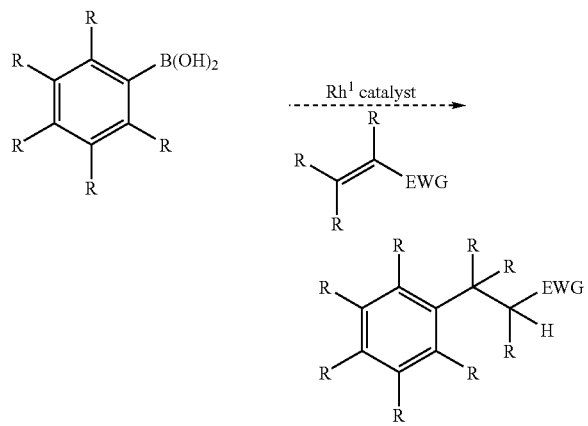

wherein the reaction comprises providing an active rhodium quinonoid catalyst, $Rh^1$, and reacting the catalyst with the boronic compound comprising a sp2 hybridized carbon-center bearing a boron to transfer the sp2 hybridized carbon to rhodium and subsequently to the conjugate acceptor, which is an electron deficient olefin, an olefin bearing one or more electron withdrawing groups (EWG), through carbo-metallation followed by proto-demetallation in a presence of a base;

wherein EWG is selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; and R is selected from the group consisting of hydrogen, carbon, halide, oxygen, sulfur, nitrogen, silicon, phosphorus, selenium, and combinations thereof.

14. The method of claim 2 comprising a reaction:

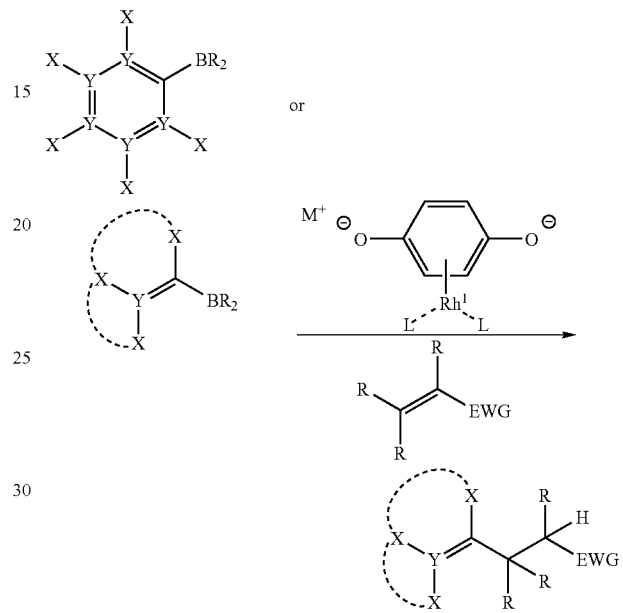

wherein the reaction comprises providing the boronic compound and the catalyst and reacting the compound and catalyst under conditions sufficient to cause the reaction, X is selected from the group consisting of hydrogen, carbon, halide, oxygen, sulfur, nitrogen, silicon, phosphorus, sulfur, selenium, and combinations thereof;

$M^+$ is a positively charged ion including any metal ion having an oxidation state at or higher than +1, and is selected from the group consisting of cationic Li, K, Cs, Be, Sr, Ba, Al, Ti, Zr, B, Si, Cd, Ag, $Ph_3PNPPh_3$, Rb, $Mg^{2+}$, $Ca^{2+}$, Na, $R_4N^+$, $Zn^{2+}$, ammonium salts including tetraalkylammonium cations, tetraalkylarsonium cations, guanidinium salts, amidinium salts, and combinations thereof;

Y is selected from the group consisting of hydrogen, carbon, halide, oxygen, sulfur, nitrogen, silicon, phosphorus, sulfur, selenium, and combinations thereof;

L is a ligand that donates electron density to the rhodium to stabilize it and each L is an identical or non-identical ligand that is either chiral or achiral and selected from the group consisting of alkenes, dialkenes, alkyene, phosphines, water, phosphites, sulfides, sulfoxides, sulfonates, sulfonamides, sulfones, ethers, amines, imines, amides, aldehydes, ketones, esters, nitriles, and combinations thereof;

wherein EWG is selected from the group consisting of a ketone, aldehyde, imide, amide, ester, thioester, acid anhydride, nitro, sulfone, nitrile, sulfoxide, phosphinate, electron deficient aromatic ring or other suitable electron withdrawing substituent that withdraws electron density either through inductive or resonance effects from olefins, and combinations thereof; R is selected from the group consisting of hydrogen, carbon, halide, oxygen, sulfur, nitrogen, silicon, phosphorus, selenium, and combinations thereof; and —BR$_2$ is any boronic containing species neutral or anionically charged where boron is bound to a transfer group.

15. The method of claim 2 comprising using the rhodium quinonoid catalyst for the conjugate addition of boronic acid comprising a reaction:

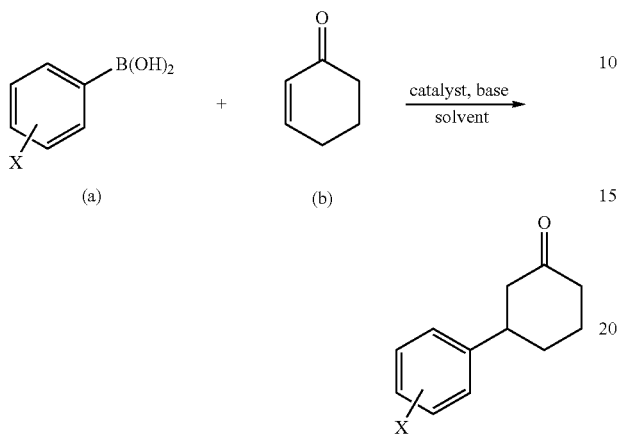

wherein the reaction comprises mixing reagents (a) and (b) and reacting the reagents and the rhodium quinonoid catalyst under conditions sufficient to cause the reaction in the presence of a base and a solvent, wherein:

X is selected from the group consisting of p-Me, m-NO$_2$, H, o-Me, 4NH-Boc, p-OMe, p-Cl, p-F, 3Cl,4F, m-NO$_2$, 3,4,5 triF, 2,3,4-triF;

the solvent is selected from the group consisting of DME/H$_2$O, H$_2$O and THF; and the base is LiOH or KOH.

16. The method of claim 15 comprising using the catalyst for the conjugate addition of aryl boronic acid to 2-cyclohexen-1-one comprising a reaction

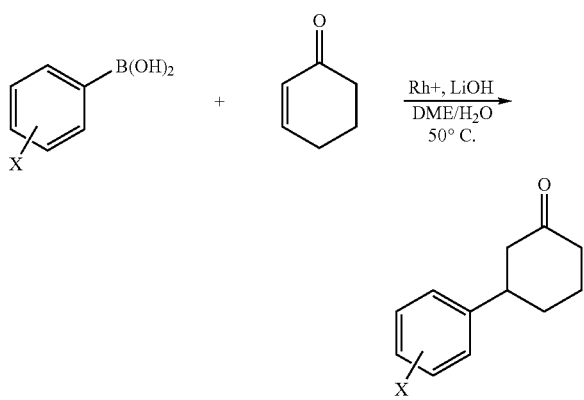

wherein:

Rh+ is the catalyst; and

X is selected from the group consisting of p-Me and m-NO$_2$.

17. A method comprising a reaction:

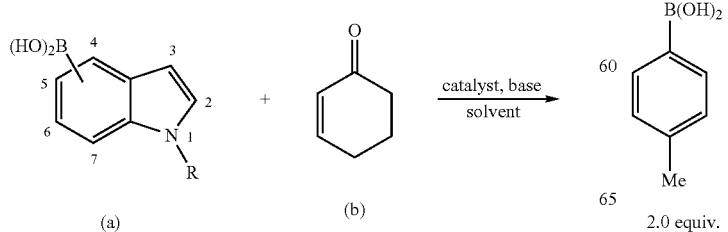

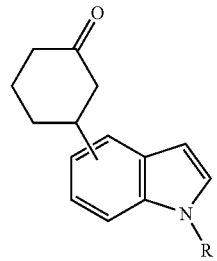

wherein the reaction comprises mixing reagents (a) and (b) and reacting the reagents with a catalyst in the presence of a base and a solvent under conditions sufficient to cause the reaction, wherein:

R is selected from the group consisting of H and Boc;

the catalyst is a rhodium quinone catalyst; the solvent is selected from the group consisting of DME/H$_2$O and THF; and the base is LiOH.

18. The method of claim 2 comprising a reaction

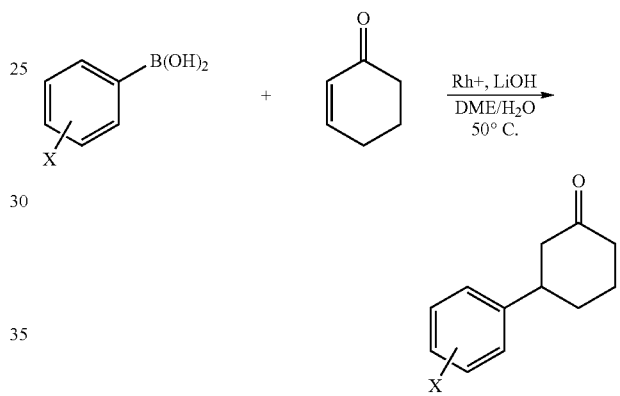

wherein:

Rh+ is a rhodium quinonoid catalyst; and

X is selected from the group consisting of: H, p-Me, o-Me, 4NH-Boc, p-OMe, p-Cl, p-F, 3Cl-4F, m-NO$_2$, 3,4,5 triF, 2,3,4-triF.

19. The method of claim 18 further comprising an additive, wherein the additive is selected from the group consisting of hydroquinone, LiBF$_4$, LiCl, pyridine, Cs$_2$CO$_3$ and Na$_2$CO$_3$.

20. A method of using a catalyst for the conjugate addition of aryl boronic substrates comprising the steps of:

a) providing a rhodium quinonoid catalyst;

b) transferring a sp2 hybridized carbon group from boron to a conjugate acceptor via the catalyst; and c) forming a product of conjugate addition.

21. The method of claim 2 comprising using the catalyst for the conjugate addition to tri-substituted olefins comprising at least one of the following reactions:

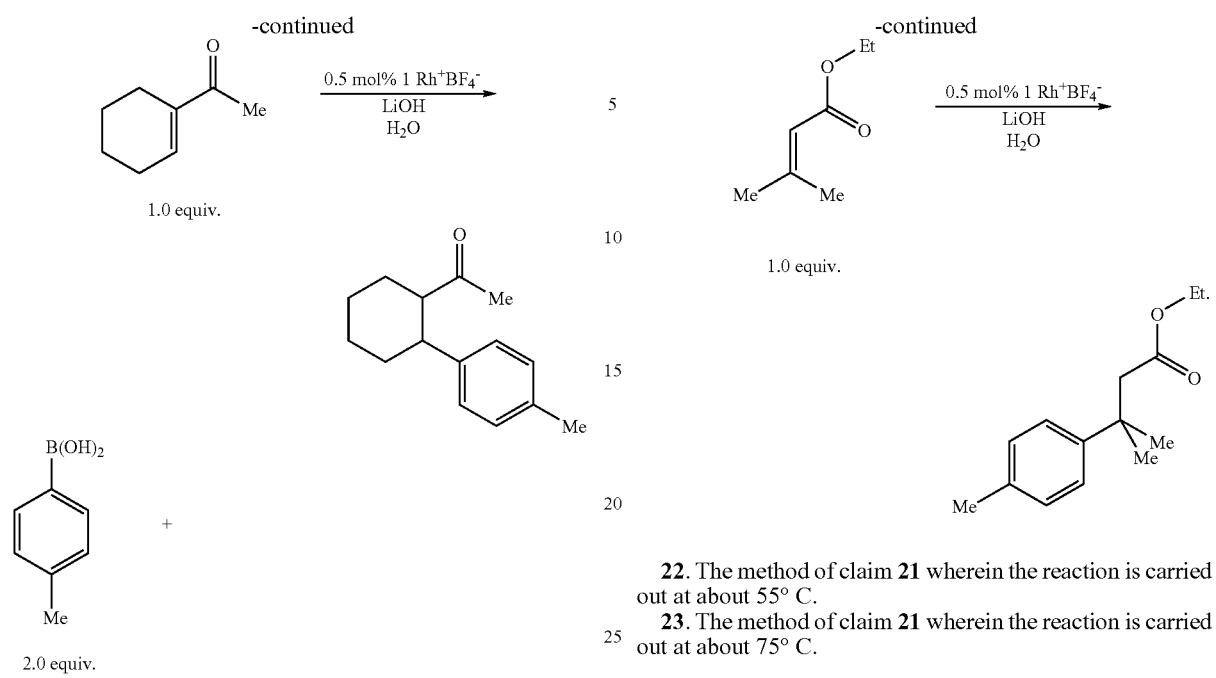
22. The method of claim 21 wherein the reaction is carried out at about 55° C.
23. The method of claim 21 wherein the reaction is carried out at about 75° C.
* * * * *